(12) United States Patent
Chiou et al.

(10) Patent No.: US 11,866,734 B2
(45) Date of Patent: Jan. 9, 2024

(54) SUPER ENHANCER FOR DRIVING PLURIPOTENCY NETWORK AND STEMNESS CIRCUITRY

(71) Applicant: Taipei Veterans General Hospital, Taipei (TW)

(72) Inventors: Shih-Hwa Chiou, Taipei (TW); Ping-Hsing Tsai, Taipei (TW); Yueh Chien, Taipei (TW)

(73) Assignee: TAIPEI VETERANS GENERAL HOSPITAL, Taipei (TW)

( * ) Notice: Subject to any disclaimer, the term of this patent is extended or adjusted under 35 U.S.C. 154(b) by 362 days.

(21) Appl. No.: 17/003,799

(22) Filed: Aug. 26, 2020

(65) Prior Publication Data
US 2021/0102174 A1   Apr. 8, 2021

Related U.S. Application Data

(60) Provisional application No. 62/891,538, filed on Aug. 26, 2019.

(51) Int. Cl.
*C12N 5/074* (2010.01)
*C12N 15/86* (2006.01)

(52) U.S. Cl.
CPC ......... *C12N 5/0696* (2013.01); *C12N 15/86* (2013.01); *C12N 2501/602* (2013.01); *C12N 2501/603* (2013.01); *C12N 2501/605* (2013.01)

(58) Field of Classification Search
None
See application file for complete search history.

(56) References Cited

U.S. PATENT DOCUMENTS 8,058,065 B2 * 11/2011 Yamanaka ........... C12N 5/0696
435/373

OTHER PUBLICATIONS

Takahashi et al. Induction of Pluripotent Stem Cells from Adult Human Fibroblasts by Defined Factors (2007), Cell, 131, pp. 861-872. (Year: 2007).*
Li et al. Disruption of OCT4 Ubiquitination Increases OCT4 Protein Stability and ASH2L-B-Mediated H3K4 Methylation Promoting Pluripotency Acquisition (2018), Stem Cell Reports, 11, pp. 973-987. (Year: 2018).*
Coulberson et al. G ene packaging with lipids, peptides and viruses inhibits transfection by electroporation in vitro (2003), Journal of Controlled Release, 86, pp. 361-370. (Year: 2003).*

* cited by examiner

*Primary Examiner* — Emily A Cordas
*Assistant Examiner* — Maytee Marie Contes De Jesus
(74) *Attorney, Agent, or Firm* — Birch, Stewart, Kolasch & Birch, LLP

(57) ABSTRACT

The preset invention relates to a novel super-enhancer-bound Ash2l/OSN complex that can drive enhance activation, govern pluripotency network and stemness circuitry, and a reprogramming system or method through the regulation of this super-enhancer, Ash2l, to modulate pluripotency and cell fates. Ash2l directly binds to super-enhancers of several stemness genes to regulate pluripotency and self-renewal in pluripotent stem cells. Ash2l recruits Oct4/Sox2/Nanog (OSN) to form Ash2l/OSN complex at the super-enhancers of Jarid2, Nanog, Sox2, and Oct4, and further drives enhancer activation, upregulation of stemness genes, and maintains the pluripotent circuitry. Ash2l knockdown abrogates the OSN recruitment to all super-enhancers and further hinders the enhancer activation. In addition, CRISPRi/dCas9-mediated blocking of Ash2l-binding motifs at these super-enhancers also prevents OSN recruitment and enhancer activation, validating that Ash2l directly binds to super-enhancers and initiates the pluripotency network. Transfection of Ash2l with W118A mutation to disrupt Ash2l-Oct4 interaction fails to rescue Ash2l-driven enhancer activation and pluripotent gene upregulation in Ash2l-depleted pluripotent stem cells.

12 Claims, 54 Drawing Sheets
(48 of 54 Drawing Sheet(s) Filed in Color)
Specification includes a Sequence Listing.

Distal II

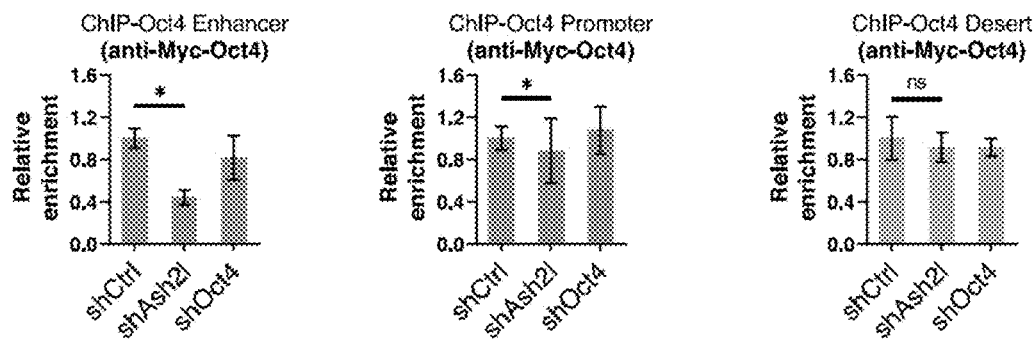
Figure.6C
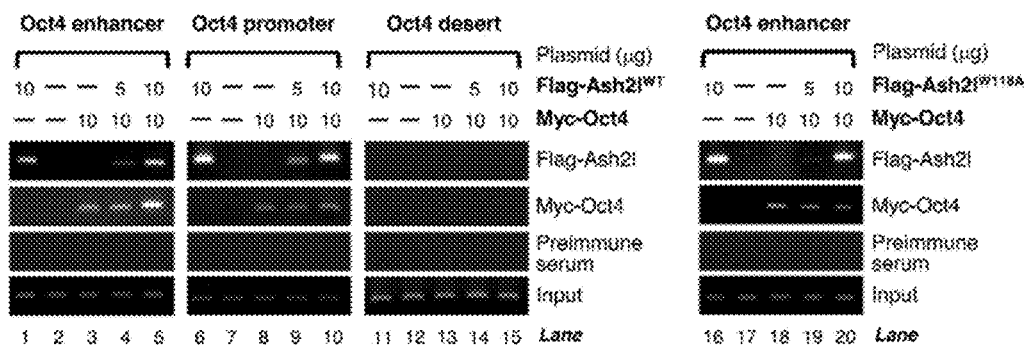
Figure.6D
Figure.6E

Wild-type Jarid2
5' TACATCCCTAGTAAACATCCAACTTCTTTTTATTC 3'
Deleted Jarid2
5' TACAT-----------------------TTTATTC 3'

Figure.12A

Wild-type Nanog
5' TTTTGACTGCTAACCACCAGAGGACCCACTTAAC 3'
Deleted Nanog
5' TTTT-------------------------CTTAAC 3'

Figure.12B

SEQUENCE LISTING

```
<160> NUMBER OF SEQ ID NOS: 56

<210> SEQ ID NO 1
<211> LENGTH: 25
<212> TYPE: DNA
<213> ORGANISM: Artificial Sequence
<220> FEATURE:
<223> OTHER INFORMATION: Synthetic: Ash2l

<400> SEQUENCE: 1
aaggaggagg ccaggacgag accaa                                          25

<210> SEQ ID NO 2
<211> LENGTH: 25
<212> TYPE: DNA
<213> ORGANISM: Artificial Sequence
<220> FEATURE:
<223> OTHER INFORMATION: Synthetic: Ash2l

<400> SEQUENCE: 2
agcccgcctg ggtatccatc acttc                                          25

<210> SEQ ID NO 3
<211> LENGTH: 22
<212> TYPE: DNA
<213> ORGANISM: Artificial Sequence
<220> FEATURE:
<223> OTHER INFORMATION: Synthetic: Oct4

<400> SEQUENCE: 3
catgcattca aactgaggca cc                                             22

<210> SEQ ID NO 4
<211> LENGTH: 22
<212> TYPE: DNA
<213> ORGANISM: Artificial Sequence
<220> FEATURE:
<223> OTHER INFORMATION: Synthetic: Oct4

<400> SEQUENCE: 4
aatgatgagt gacagacagg cc                                             22
```

```
<210> SEQ ID NO 5
<211> LENGTH: 20
<212> TYPE: DNA
<213> ORGANISM: Artificial Sequence
<220> FEATURE:
<223> OTHER INFORMATION: Synthetic: Sox2

<400> SEQUENCE: 5
ggtgcaaaaa gaggagagta                                               20

<210> SEQ ID NO 6
<211> LENGTH: 20
<212> TYPE: DNA
<213> ORGANISM: Artificial Sequence
<220> FEATURE:
<223> OTHER INFORMATION: Synthetic: Sox2

<400> SEQUENCE: 6
tttgcgttaa tttggatggg                                               20

<210> SEQ ID NO 7
<211> LENGTH: 24
<212> TYPE: DNA
<213> ORGANISM: Artificial Sequence
<220> FEATURE:
<223> OTHER INFORMATION: Synthetic: Nanog

<400> SEQUENCE: 7
aactcttctt tctatgatct ttcc                                          24

<210> SEQ ID NO 8
<211> LENGTH: 20
<212> TYPE: DNA
<213> ORGANISM: Artificial Sequence
<220> FEATURE:
<223> OTHER INFORMATION: Synthetic: Nanog

<400> SEQUENCE: 8
cttcctcaga actaggcaaa                                               20

<210> SEQ ID NO 9
<211> LENGTH: 24
<212> TYPE: DNA
<213> ORGANISM: Artificial Sequence
<220> FEATURE:
<223> OTHER INFORMATION: Synthetic: Wdr5

<400> SEQUENCE: 9
gaagggccac agtaactacg tctt                                          24

<210> SEQ ID NO 10
<211> LENGTH: 24
<212> TYPE: DNA
<213> ORGANISM: Artificial Sequence
<220> FEATURE:
<223> OTHER INFORMATION: Synthetic: Wdr5

<400> SEQUENCE: 10
gaggccatca tagctactgg aaac                                          24

<210> SEQ ID NO 11
<211> LENGTH: 20
<212> TYPE: DNA
<213> ORGANISM: Artificial Sequence
<220> FEATURE:
<223> OTHER INFORMATION: Synthetic: Gapdh
```

```
<400> SEQUENCE: 11
ctcatgacca cagtccatgc                                               20

<210> SEQ ID NO 12
<211> LENGTH: 20
<212> TYPE: DNA
<213> ORGANISM: Artificial Sequence
<220> FEATURE:
<223> OTHER INFORMATION: Synthetic: Gapdh

<400> SEQUENCE: 12
ttcagctctg ggatgacctt                                               20

<210> SEQ ID NO 13
<211> LENGTH: 20
<212> TYPE: DNA
<213> ORGANISM: Artificial Sequence
<220> FEATURE:
<223> OTHER INFORMATION: Synthetic: Jarid2

<400> SEQUENCE: 13
acaaacgtga cttccaacat                                               20

<210> SEQ ID NO 14
<211> LENGTH: 20
<212> TYPE: DNA
<213> ORGANISM: Artificial Sequence
<220> FEATURE:
<223> OTHER INFORMATION: Synthetic: Jarid2

<400> SEQUENCE: 14
aaaactacat cagcgaaacg                                               20

<210> SEQ ID NO 15
<211> LENGTH: 23
<212> TYPE: DNA
<213> ORGANISM: Artificial Sequence
<220> FEATURE:
<223> OTHER INFORMATION: Synthetic: Cdx2

<400> SEQUENCE: 15
acgtgagcta ccttctggac aag                                           23

<210> SEQ ID NO 16
<211> LENGTH: 23
<212> TYPE: DNA
<213> ORGANISM: Artificial Sequence
<220> FEATURE:
<223> OTHER INFORMATION: Synthetic: Cdx2

<400> SEQUENCE: 16
gtactgcgga ggactgacaa agt                                           23

<210> SEQ ID NO 17
<211> LENGTH: 20
<212> TYPE: DNA
<213> ORGANISM: Artificial Sequence
<220> FEATURE:
<223> OTHER INFORMATION: Synthetic: Fgf5

<400> SEQUENCE: 17 agggattgt aggaatacga                                                20

<210> SEQ ID NO 18
```

```
<211> LENGTH: 20
<212> TYPE: DNA
<213> ORGANISM: Artificial Sequence
<220> FEATURE:
<223> OTHER INFORMATION: Synthetic: Fgf5

<400> SEQUENCE: 18
cagtcatccg taaatttggc                                              20

<210> SEQ ID NO 19
<211> LENGTH: 24
<212> TYPE: DNA
<213> ORGANISM: Artificial Sequence
<220> FEATURE:
<223> OTHER INFORMATION: Synthetic: Nestin

<400> SEQUENCE: 19
acctcaagat gtcccttagt ctgg                                         24

<210> SEQ ID NO 20
<211> LENGTH: 24
<212> TYPE: DNA
<213> ORGANISM: Artificial Sequence
<220> FEATURE:
<223> OTHER INFORMATION: Synthetic: Nestin

<400> SEQUENCE: 20
ggagtctcaa gggtattagg caag                                         24

<210> SEQ ID NO 21
<211> LENGTH: 23
<212> TYPE: DNA
<213> ORGANISM: Artificial Sequence
<220> FEATURE:
<223> OTHER INFORMATION: Synthetic: Pax6

<400> SEQUENCE: 21
tctttcttgg ccagcaaaag tta                                          23

<210> SEQ ID NO 22
<211> LENGTH: 23
<212> TYPE: DNA
<213> ORGANISM: Artificial Sequence
<220> FEATURE:
<223> OTHER INFORMATION: Synthetic: Pax6

<400> SEQUENCE: 22
ttgtgaacaa ctgcaaaaca ctt                                          23

<210> SEQ ID NO 23
<211> LENGTH: 22
<212> TYPE: DNA
<213> ORGANISM: Artificial Sequence
<220> FEATURE:
<223> OTHER INFORMATION: Synthetic: dCas9

<400> SEQUENCE: 23
acaagaagta cagcatcggc ct                                           22

<210> SEQ ID NO 24
<211> LENGTH: 20
<212> TYPE: DNA
<213> ORGANISM: Artificial Sequence
<220> FEATURE:
<223> OTHER INFORMATION: Synthetic: dCas9

<400> SEQUENCE: 24
```

-continued atttcttgct gggcaccttg                                               20

<210> SEQ ID NO 25
<211> LENGTH: 22
<212> TYPE: DNA
<213> ORGANISM: Artificial Sequence
<220> FEATURE:
<223> OTHER INFORMATION: Synthetic: Nanog [-45k]

<400> SEQUENCE: 25
cctttcagtt gtctcccgaa ac                                            22

<210> SEQ ID NO 26
<211> LENGTH: 20
<212> TYPE: DNA
<213> ORGANISM: Artificial Sequence
<220> FEATURE:
<223> OTHER INFORMATION: Synthetic: Nanog [-45k]

<400> SEQUENCE: 26
gggggacgtt tcacattcaa                                               20

<210> SEQ ID NO 27
<211> LENGTH: 24
<212> TYPE: DNA
<213> ORGANISM: Artificial Sequence
<220> FEATURE:
<223> OTHER INFORMATION: Synthetic: Oct4 [-15k]

<400> SEQUENCE: 27
tctacttgca gttctgctga gtcc                                          24

<210> SEQ ID NO 28
<211> LENGTH: 20
<212> TYPE: DNA
<213> ORGANISM: Artificial Sequence
<220> FEATURE:
<223> OTHER INFORMATION: Synthetic: Oct4 [-15k]

<400> SEQUENCE: 28
tgtgaatggg gaccaatggt                                               20

<210> SEQ ID NO 29
<211> LENGTH: 22
<212> TYPE: DNA
<213> ORGANISM: Artificial Sequence
<220> FEATURE:
<223> OTHER INFORMATION: Synthetic: Jarid [-26k]

<400> SEQUENCE: 29
aataggctgg cctcaaactc ag                                            22

<210> SEQ ID NO 30
<211> LENGTH: 22
<212> TYPE: DNA
<213> ORGANISM: Artificial Sequence
<220> FEATURE:
<223> OTHER INFORMATION: Synthetic: Jarid [-26k]

<400> SEQUENCE: 30
ccagtccaca gcactgaaaa ga                                            22

<210> SEQ ID NO 31
<211> LENGTH: 43
<212> TYPE: DNA

<213> ORGANISM: Artificial Sequence
<220> FEATURE:
<223> OTHER INFORMATION: Synthetic: DNA probe

<400> SEQUENCE: 31
cggagaacaa tgcccttccc tattctgcag cctttataca gcc        43

<210> SEQ ID NO 32
<211> LENGTH: 43
<212> TYPE: DNA
<213> ORGANISM: Artificial Sequence
<220> FEATURE:
<223> OTHER INFORMATION: Synthetic: DNA probe

<400> SEQUENCE: 32
caccgtccga tcgctaagtg tggggcaccg tccgatcgct aag        43

<210> SEQ ID NO 33
<211> LENGTH: 35
<212> TYPE: DNA
<213> ORGANISM: Artificial Sequence
<220> FEATURE:
<223> OTHER INFORMATION: Synthetic: Wild-type Jarid2

<400> SEQUENCE: 33
tacatcccta gtaaacatcc aacttctttt tattc        35

<210> SEQ ID NO 34
<211> LENGTH: 12
<212> TYPE: DNA
<213> ORGANISM: Artificial Sequence
<220> FEATURE:
<223> OTHER INFORMATION: Synthetic: Deleted Jarid2

<400> SEQUENCE: 34
tacattttat tc        12

<210> SEQ ID NO 35
<211> LENGTH: 35
<212> TYPE: DNA
<213> ORGANISM: Artificial Sequence
<220> FEATURE:
<223> OTHER INFORMATION: Synthetic: Wild-type Nanog

<400> SEQUENCE: 35
ttttgactgc taaccaccca gaggacccac ttaac        35

<210> SEQ ID NO 36
<211> LENGTH: 10
<212> TYPE: DNA
<213> ORGANISM: Artificial Sequence
<220> FEATURE:
<223> OTHER INFORMATION: Synthetic: Deleted Nanog

<400> SEQUENCE: 36
ttttcttaac        10

<210> SEQ ID NO 37
<211> LENGTH: 126
<212> TYPE: DNA
<213> ORGANISM: Artificial Sequence
<220> FEATURE:
<223> OTHER INFORMATION: Synthetic: Jarid2 upstream 5'

<400> SEQUENCE: 37
ttacatccct agtaaacatc aacttctttt ttattcaagg aatcgttgac aatggaaaca        60

```
caaagaagtt gtaaatgaat aatctatgga gtttagacac agagtcacca ccaaggttgg      120
agtctt                                                                126

<210> SEQ ID NO 38
<211> LENGTH: 126
<212> TYPE: DNA
<213> ORGANISM: Artificial Sequence
<220> FEATURE:
<223> OTHER INFORMATION: Synthetic: Jarid2 upstream 3 reverse complement

<400> SEQUENCE: 38
aagactccaa ccttggtggt gactctgtgt ctaaactcca tagattattc atttacaact      60
tctttgtgtt tccattgtca acgattcctt gaataaaaag aagttggatg tttactaggg     120
atgtaa                                                                126

<210> SEQ ID NO 39
<211> LENGTH: 127
<212> TYPE: DNA
<213> ORGANISM: Artificial Sequence
<220> FEATURE:
<223> OTHER INFORMATION: Synthetic: Nanog upstream 5

<400> SEQUENCE: 39
gactccaagg ctagcgattc acacccctcc cccacctgtc cctagtcccc gctccttttc      60
agcactaacc atacaagttc atcttttact cttgttttga ctgctaacca cccagaggac     120
ccactta                                                               127

<210> SEQ ID NO 40
<211> LENGTH: 127
<212> TYPE: DNA
<213> ORGANISM: Artificial Sequence
<220> FEATURE:
<223> OTHER INFORMATION: Synthetic: Nanog upstream 3 reverse complement

<400> SEQUENCE: 40
taagtgggtc ctctgggtgg ttagcagtca aacaagagt aaaagatgaa cttgtatggt       60
tagtgctgaa aaggagcggg gactagggac aggtggggga ggggtgtgaa tcgctagcct     120
tggagtc                                                               127

<210> SEQ ID NO 41
<211> LENGTH: 130
<212> TYPE: DNA
<213> ORGANISM: Artificial Sequence
<220> FEATURE:
<223> OTHER INFORMATION: Synthetic: Oct4 upstream 5

<400> SEQUENCE: 41
gcagacggca gatgcataac aaaggtgcat gatagctctg ccctgggggc agagaagatg      60
gttggggagg ggtccctctc gtcctagccc ttccttaatc tgctattgag gaagctttgt     120
gaacttggcg                                                            130

<210> SEQ ID NO 42
<211> LENGTH: 130
<212> TYPE: DNA
<213> ORGANISM: Artificial Sequence
<220> FEATURE:
<223> OTHER INFORMATION: Synthetic: Oct4 upstream 3 reverse complement

<400> SEQUENCE: 42
```

```
cgccaagttc acaaagcttc ctcaatagca gattaaggaa gggctaggac gagagggacc    60
cctccccaac catcttctct gcccccaggg cagagctatc atgcaccttt gttatgcatc   120
tgccgtctgc                                                          130
```

<210> SEQ ID NO 43
<211> LENGTH: 23
<212> TYPE: DNA
<213> ORGANISM: Artificial Sequence
<220> FEATURE:
<223> OTHER INFORMATION: Synthetic: Jarid2 A(-)

<400> SEQUENCE: 43

```
attcaaggaa tcgttgacaa tgg                                            23
```

<210> SEQ ID NO 44
<211> LENGTH: 23
<212> TYPE: DNA
<213> ORGANISM: Artificial Sequence
<220> FEATURE:
<223> OTHER INFORMATION: Synthetic: Jarid2 B(-)

<400> SEQUENCE: 44

```
cacagagtga ccaccaaggt tgg                                            23
```

<210> SEQ ID NO 45
<211> LENGTH: 23
<212> TYPE: DNA
<213> ORGANISM: Artificial Sequence
<220> FEATURE:
<223> OTHER INFORMATION: Synthetic: Jarid2 C(+)

<400> SEQUENCE: 45

```
aagaagttgg atgtttacta ggg                                            23
```

<210> SEQ ID NO 46
<211> LENGTH: 23
<212> TYPE: DNA
<213> ORGANISM: Artificial Sequence
<220> FEATURE:
<223> OTHER INFORMATION: Synthetic: Nanog D(-)

<400> SEQUENCE: 46

```
tttgactgct aaccacccag agg                                            23
```

<210> SEQ ID NO 47
<211> LENGTH: 23
<212> TYPE: DNA
<213> ORGANISM: Artificial Sequence
<220> FEATURE:
<223> OTHER INFORMATION: Synthetic: Nanog E(+)

<400> SEQUENCE: 47

```
gttagtgctg aaaaggagcg ggg                                            23
```

<210> SEQ ID NO 48
<211> LENGTH: 23
<212> TYPE: DNA
<213> ORGANISM: Artificial Sequence
<220> FEATURE:
<223> OTHER INFORMATION: Synthetic: Nanog F(+)

<400> SEQUENCE: 48

```
ggggtgtgaa tcgctagcct tgg                                            23
```

<210> SEQ ID NO 49
<211> LENGTH: 23
<212> TYPE: DNA
<213> ORGANISM: Artificial Sequence
<220> FEATURE:
<223> OTHER INFORMATION: Synthetic: Oct4 G(+)

<400> SEQUENCE: 49
aaggaagggc taggacgaga ggg                                            23

<210> SEQ ID NO 50
<211> LENGTH: 23
<212> TYPE: DNA
<213> ORGANISM: Artificial Sequence
<220> FEATURE:
<223> OTHER INFORMATION: Synthetic: Oct4 H(-)

<400> SEQUENCE: 50
agacggcaga tgcataacaa agg                                            23

<210> SEQ ID NO 51
<211> LENGTH: 23
<212> TYPE: DNA
<213> ORGANISM: Artificial Sequence
<220> FEATURE:
<223> OTHER INFORMATION: Synthetic: Oct4 I(-)

<400> SEQUENCE: 51
aggaagcttt gtgaacttgg cgg                                            23

<210> SEQ ID NO 52
<211> LENGTH: 23
<212> TYPE: DNA
<213> ORGANISM: Artificial Sequence
<220> FEATURE:
<223> OTHER INFORMATION: Synthetic: Ctrl

<400> SEQUENCE: 52
caccgtccga tcgctaagtg tgg                                            23

<210> SEQ ID NO 53
<211> LENGTH: 23
<212> TYPE: DNA
<213> ORGANISM: Artificial Sequence
<220> FEATURE:
<223> OTHER INFORMATION: Synthetic: Ctrl

<400> SEQUENCE: 53 aaaccccac acttagcgat cgg                                             23

<210> SEQ ID NO 54
<211> LENGTH: 19
<212> TYPE: DNA
<213> ORGANISM: Artificial Sequence
<220> FEATURE:
<223> OTHER INFORMATION: Synthetic: shAsh2l-1

<400> SEQUENCE: 54
aaggagcagc gatggcggc                                                 19

<210> SEQ ID NO 55
<211> LENGTH: 21
<212> TYPE: DNA
<213> ORGANISM: Artificial Sequence
<220> FEATURE:
<223> OTHER INFORMATION: Synthetic: shAsh2l-2

```
<400> SEQUENCE: 55
aaaaggagca gcgatggcgg c                                           21

<210> SEQ ID NO 56
<211> LENGTH: 19
<212> TYPE: DNA
<213> ORGANISM: Artificial Sequence
<220> FEATURE:
<223> OTHER INFORMATION: Synthetic: shOct4

<400> SEQUENCE: 56
gaaggatgtg gttcgagta                                              19
```

SUPER ENHANCER FOR DRIVING PLURIPOTENCY NETWORK AND STEMNESS CIRCUITRY

CROSS REFERENCE

This Non-provisional application claims the priority under 35 U.S.C. § 119(a) on U.S. Patent Provisional Application No. 62/891,538 filed on Aug. 26, 2019, the entire contents of which are hereby incorporated by reference.

FIELD OF THE INVENTION

The present invention relates to a new super enhancer for driving pluripotency network and stemness circuitry.

BACKGROUND OF THE INVENTION

Cellular reprogramming and maintenance of pluripotency require a complicated and interactive regulatory network of transcription factors, including Oct4, Sox2, Nanog, and Esrrb (1-5). By participating in various regulatory interactions, these transcription factors increase the expression of themselves as well as other pluripotency-related genes, and suppress the expression of genes that contribute to differentiation (6). However, the interactions and regulatory circuit among these transcription factor networks are poorly understood. A super-enhancer in the mammalian genome is a region of multiple putative enhancers bound by substantial number of mediators to drive transcription and control cell identity (7). In pluripotent stem cells such as embryonic stem cells (ESCs), super-enhancers are enriched for Oct4, Sox2, and Nanog (OSN), which form the OSN complex (8). Super-enhancers, normally away and upstream from promoters, form an enhancer-promoter loop structure and recruit p300/CBP and CHD7 to catalyze H3K27 acetylation, and Mediator (MED1) to facilitate Pol II activity through the OSN complex (8-10). A previous report showed that epigenetic modifications at super-enhancers by Tex10 regulate super-enhancer activity, leading to enhanced pluripotency and reprogramming (10). The activity of Oct4 distal enhancer was also implicated in the regulation of pluripotent status (11). Moreover, the chromatin remodeling of Oct4 gene has been demonstrated to be a crucial step for a successful reprogramming (12). However, the transcription factor network orchestrating super-enhancer activity in cell reprogramming and pluripotency maintenance remains mostly uncertain.

Pluripotent stem cells exhibit a relatively open chromatin structure and unique epigenetic features. Methylation of histone H3K4 correlates with open chromatin structure and active transcription. A highly conserved mixed lineage leukemia (MLL) protein complex harbors methyl-transferase activity, which depends on its core components (Wdr5, Ash2l, RbBP5, and Dpy30, termed WARD), and is responsible for catalyzing the mono-, di-, and tri-methylation of H3K4 (13). Among the members of WARD, biochemical studies suggested that Wdr5 is the central component of the MLL complex and that Ash2l is required for H3K4 trimethylation (14, 15). Wdr5 interacts with Oct4 and shares gene regulatory functions with Oct4 (16), and is essential for the reprogramming of somatic cells as well as ESC self-renewal (16). Genome-wide mapping showed that Wdr5 along with Oct4 and Rbbp5 localizes to the proximal region around promoters to regulate pluripotency (16). In addition, Ash2l plays important roles in regulating pluripotency and maintaining open chromatin structure (17). Without the involvement of Ash2l, Wdr5 and other MLL components still form a complex which have distinct structures and functions from the complex containing Ash2l, suggesting a unique role of Ash2l (18). However, the detailed mechanisms and signaling networks of the Ash2l-mediated regulation of pluripotency remain unclear.

The proximal and distal enhancers of Oct4 coordinately regulate Oct4 expression during embryonic and germ cell development, highlighting the significance of the Oct4 enhancer in stemness regulation (11). Although Wdr5 was reported to interact with Oct4 and binds to the Oct4 promoter to regulate pluripotency (16), the involvement of MLL members in the regulation of super-enhancer activity in stem cells is not known.

It is still desirable to develop a new method for cell reprogramming and enhancing the pluripotency network.

SUMMARY OF THE INVENTION

It is unexpectedly found in the present invention that Ash2l-a interacts with Oct4-stemness circuitry to promote super-enhancer-driven pluripotency network.

In one aspect, the invention provides a method for preparing induced pluripotent stem cells (iPSCs) from somatic cells, comprising:
(a) transfecting or transducing the transcription factor Ash2l-a into isolated somatic cells, or contacting or exposing isolated somatic cells with/to the transcription factor Ash2l-a, which the isolated somatic cells can express transcription factor; and
(b) culturing the isolated somatic cells as obtained in step (a) under appropriate conditions, thereby converting the somatic cells into iPSCs and maintaining pluripotency and self-renewal ability.

In one embodiment of the invention, the transcription factor comprises Ash2l-a binding to super-enhancers of Jarid2, Nanog, Sox2, and Oct4.

In one embodiment of the invention, the isolated somatic cells are transfected or transduced with one or more plasmid or vector comprising the transcription factor operably linked to a promoter.

In one example of the invention, the vector is a viral vector.

In one example of the invention, the isolated somatic cells are transfected by electroporation.

According to the invention, the isolated somatic cells are fibroblasts, nerve cells, amniotic fluid cells, bone marrow cells, blood cells, myocardial cells, dermal or epidermal cells, connective tissue cells, chondrocytes, rod and cone cells, retinal pigment epithelia, or pancreatic cells.

In one example of the invention, the fibroblast is dermal fibroblast.

In one example of the invention, the blood cell is peripheral blood mononuclear cell.

According to the invention, the iPSCs can differentiate to nervous system, teeth, hair, exocrine glands, epithelium, or mesenchyme from ectoderm.

According to the invention, the iPSCs can differentiate to the muscle of smooth, cardiac and skeletal, the muscles of the tongue, the pharyngeal arches muscle, connective tissue, dermis and subcutaneous layer of the skin, bone and cartilage, dura mater, endothelium of blood vessels, red blood cells, white blood cells, microglia and Kupffer cells, the kidneys and the adrenal cortex cartilage, gonads, or keratinocytes from mesoderm.

According to the invention, the iPSCs can differentiate to lung cells, thyroid cells, pancreatic cells, liver cells, retinal pigment epithelium, or eyes from endoderm.

In another aspect, the present invention provides an iPSC(s) obtained by the method of the invention.

In a further aspect, the invention provides a use of Ash2l-a for driving an enhancer activation, upregulation of a stemness gene, and maintaining the pluripotent circuitry to regulate pluripotency and self-renewal in pluripotent stem cells.

In one embodiment of the invention, the stemness gene is selected from the group consisting of Jarid2, Nanog, Sox2, Oct4 and any combination thereof.

According to the invention, Ash2l-a directly binds to the super-enhancers of the stemness genes to regulate pluripotency and self-renewal in pluripotent stem cells.

In one example of the invention, Ash2l-a recruits Oct4, Sox2, and Nanog (OSN) to form an Ash2l-a/OSN complex at the super-enhancers of Jarid2, Nanog, Sox2, and Oct4, and further drives enhancer activation, upregulation of stemness genes, and maintains the pluripotent circuitry.

In a yet aspect, the invention provides an enhancer-bound Ash2l-a/OSN complex for driving enhancer activation, governing pluripotency network and stemness circuitry in pluripotent stem cells.

BRIEF DESCRIPTION OF THE SEVERAL VIEWS OF THE DRAWINGS

The patent or application file contains at least one color drawing. Copies of this patent or patent application publication with color drawing will be provided by the USPTO upon request and payment of the necessary fee.

The foregoing summary, as well as the following detailed description of the invention, will be better understood when read in conjunction with the appended drawings. For the purpose of illustrating the invention, there are shown in the drawings embodiment which is presently preferred. It should be understood, however, that the invention is not limited to this embodiment.

In the drawings:

Figure 1A:
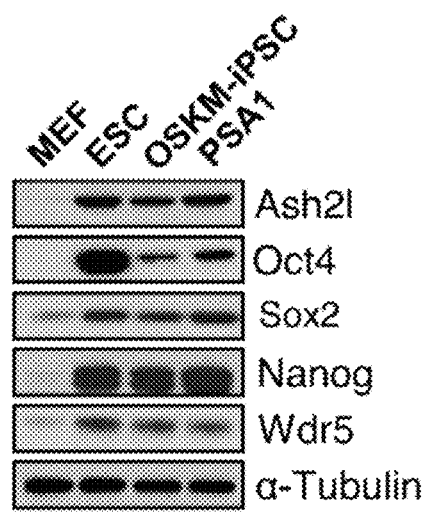

FIGS. 1A-1M show that Ash2l expression is essential for iPSC generation. (A) Western blot shows the protein expression of Ash2l-a, Oct4, Sox2, Nanog, and Wdr5 in mouse fibroblasts (MEFs), mouse embryonic stem cells (ESCs), induced pluripotent stem cells (iPSCs) and embryonal carcinoma cell line PSA1. α-Tubulin was used as loading control. (B) Time-course Western blot shows the changes in the protein content of Ash2l-a, Oct4, Sox2, Wdr5, and Klf4 during the reprogramming process of MEFs. The reprogramming was induced by infecting conventional reprogramming factors Oct4, Sox2, Klf4 and c-Myc (OSKM) in MEFs. Non-infected MEFs and ESCs were used as negative and positive controls, respectively. α-Tubulin was used as loading control. (C) A time-course qPCR shows the changes in the mRNA expression of Ash2l-a, Oct4, Sox2, Nanog, Nr5a2, and Wdr5 during reprogramming. (D) Alkaline phosphatase (AP) staining shows the reprogramming colony size of control or Ash2l-a knockdown MEFs at day 12 post-reprogramming. Control (shCtrl) and Ash2l-a knockdown (shAsh2l) MEFs were subjected to the reprogramming process using OSKM factors. Twelve days after reprogramming, the efficiency of Ash2l-a knockdown was confirmed by Western blot (upper), and MEFs were then subjected to AP staining (lower). (E) Reprogramming efficiency of MEFs with or without Ash2l-a knockdown. MEFs were reprogrammed by OSKM with or without Ash2l-a knockdown. Reprogrammed MEFs were stained with AP 24 days after reprogramming (left), and the numbers of AP-positive colonies (right) in each plate were calculated. (F) Measurements of the colony numbers of OSKM-reprogrammed MEFs with or without Ash2l-a knockdown at all given colony size at day 24 post-reprogramming. Data are presented as mean±SD. *p<0.01. (G) qPCR analysis of pluripotency genes (Oct4, Sox2, and Nanog) in ESCs with or without Ash2l-a knockdown. (H) Immunofluorescence staining showing the Oct4 protein expression in ESCs with or without Ash2l-a-knockdown. DAPI was used for staining the nucleus. Scale bar=100 µm. (I) qPCR analysis of development-related genes (ectoderm: Cdx2, Fgf5, Nestin, Pax6; mesoderm endoderm: T, Msx1, Sox17; endoderm: Gata6, Afp, HNF4α) in ESCs with or without Ash2l-a knockdown. (J) Western blot shows the expression of endogenous Ash2l-a, Oct4, and Nanog protein in OSK-reprogrammed MEFs with or without Ash2l-a overexpression. α-Tubulin was used as loading control. (K) Reprogramming efficiency of MEFs infected with OSKM (left) or OSK (right), with or without Ash2l-a overexpression. Reprogrammed MEFs were subjected to AP staining 24 days after infection, and the numbers of AP-positive colonies in each plate were calculated. Data are presented as mean±SD. *p<0.01 (L) Ex vivo biopsies and histological analysis reveal the teratoma formation in the grafts of OSK- and Ash2l-a-reprogrammed iPSCs in the dorsal flanks of nude mice. Sections of the teratoma tissues were subjected to hematoxylin and eosin staining for the examination of the formation of three germ layers. Ectoderm: neuronal epithelium; Mesoderm: cartilage and keratinocytes; Endoderm: columnar epithelium. (M) Competence of OSK/Ash2l-a-reprogrammed iPSCs to generate chimeric mice is confirmed by coat color. Western blot in panels A, B, D, and J are representatives of three separate experiments using independent cell preparations. The quantification of alkaline phosphatase staining shown in panels E and K are the mean±SD of six independent experiments. Data are normalized to Gapdh and are presented as mean±SD. *p<0.01. See also FIG. 8.

FIGS. 2A-2J show that Ash2l-a forms complexes with Oct4, Sox2, and Nanog in the absence of Wdr5. (A) The ESC nuclear extracts were separated into seven fractions by gel filtration assay based on the molecular weight of filtrated nuclear extracts. Based on the filtration order of the fraction, these fractions were defined as fraction 1 to 7. Migration of molecular markers is indicated above the panels. (B) Western blot shows the protein expression pattern among the seven fractions of ESC nuclear extracts. Note that Oct4, Sox2, and Nanog are enriched in fractions 1 to 3 and Wdr5, Rbbp5, and Dpy30 are enriched in fractions 2 to 4. Oct4, Sox2, Nanog, Wdr5, Rbbp5, and Dpy30 are all enriched in fraction 3. (C) Immunoprecipitation of fraction 1 shows the interaction of Ash2l-a with Oct4, Sox2, and Nanog (left). In the fraction 3 filtrated from the ESC nuclear extracts, immunoprecipitation shows that Ash2l-a still interacts with Oct4, Sox2, and Nanog in the ESC extracts with or without Wdr5 knockdown (right). To examine whether Wdr5 is involved in the interaction of Ash2l-a and other assayed proteins, the nuclear extracts from ESCs with or without Wdr5 knockdown were subjected to gel filtration and fractionation experiments. The fraction 3 from ESCs with or without Wdr5 knockdown was subjected to immunoprecipitation assay. Ash2l-a were immunoprecipitated, and the amount of co-precipitated proteins were analyzed by Western blot. (D) Scheme depicting the design of different constructs of Flag-tagged Ash2l-a with truncation (Ash2l-N terminus: 1-172, the PHD domain; Ash2l-C terminus: 387-

623, the SPRY domain) or full-length Ash2l-a (Ash2l-Full length: 1-623). (E) Immunoprecipitation assay indicates that N terminus of Ash2l-a interacts with Oct4, Sox2, and Nanog. ESCs were transfected with full-length or truncated Flag-tagged Ash2l-a and subjected to the immunoprecipitation assay. Truncated or full-length Flag-tagged Ash2l-a were immunoprecipitated, and the protein amount of co-precipitated Oct4, Sox2, and Nanog were analyzed by Western blot. Rbbp5 was used as the control protein that recognizes the C terminus of Ash2l-a. (F) GST Pull-down assay indicates the direct interaction among Ash2l-a and various recombinant GST-fusion proteins. Recombinant GST-fusion proteins of Oct4, Sox2, Nanog, and p300 (Taz) were subjected to a GST pull-down assay and individually incubated with Flag-tagged Ash2l-a full-length and truncated forms of Ash2l-a. Western blot of the immunoprecipitants confirmed the direct binding of Oct4, Sox2, and Nanog to the full-length and N terminus of Ash2l-a. (G) In vitro pull-down assay with full-length or truncated Ash2l-a for evaluating the functional domain(s) of Ash2l-a for the interaction between Ash2l-a and other proteins. Recombinant GST-fusion proteins of Oct4, Sox2, Nanog, and Rbbp5 were subjected to a Flag pull-down assay and individually incubated with Flag-tagged Ash2l-Full length, Ash2l-N terminus, and Ash2l-C terminus. The co-precipitated complexes were separated on SDS-PAGE and stained with Coomassie blue. (H) Simulation of the molecular docking of Oct4 and Ash2l-a using the ZDOCK software. Several residues at the N terminus of Ash2l-a, including K117, W118, E180A, K190A, N217A, and K220A, were predicted as the crucial position for the Ash2l-a-Oct4 interaction. (I) Validating the crucial residue of Ash2l-a for Ash2l-a-Oct4 interaction in ESCs using immunoprecipitation. ESCs were transfected with full-length or truncated Flag-tagged Ash2l-a and the cell lysates were purified. Flag-tagged Ash2l-a with distinct mutated residues (K117A, W118A, E180A, K190A, N217A, and K220A) were immunoprecipitated with Myc-tagged Oct4. W118A point mutation of Ash2l-a significantly reduced 79.2% of Ash2l-a interaction with Oct4. (J) In vitro pull-down assay with wild-type or W118A-mutated Ash2l-a for evaluating the interaction of Ash2l-a variants with indicated GST-tagged proteins. Recombinant GST-fusion proteins of Oct4, Sox2, Nanog, Rbbp5, and Wdr5 were subjected to a Flag pull-down assay and individually incubated with Flag-tagged wild-type Ash2l-a or Ash2l-a W118A mutant. The co-precipitated complexes were separated on SDS-PAGE and stained with Coomassie blue.

FIGS. 3A-3G show that Ash2l-a, Oct4, Sox2, and Nanog colocalized to distal cis-elements of stemness genes. (A) Heatmap analysis shows the genome-wide chromatin immunoprecipitation-sequencing (ChIP-seq) binding profiles of Oct4, Sox2, Nanog, Ash2l-a, Wdr5, Rbbp5, Dpy30, p300, H3K27ac, H3K4me1, and H3K4me3 from existing ChIP-seq data of the ENCODE consortium and previously reported studies. Near, 0 to 2 k bp; Distal I, 2 to 10 k bp; Distal II, 10 to 100 k bp; other, >100 k bp. (B) Cumulative probability of the distance to the closest TSS reveals that the binding loci for Oct4, Ash2l-a, and OA predominantly localize farther from the TSS, while the binding loci for Wdr5-related peaks (i.e. W, OW, AW, and OAW) were relatively closer to the TSS. OA: Oct4-Ash2l-a; OW: Oct4-Wdr5; AW: Ash2l-a-Wdr5; OAW: Oct4-Ash2l-a-Wdr5. (C) A similarity matrix calculated based on the ChIP-seq data shows that the binding patterns for Ash2l-a and OA are similar, while the patterns of Wdr5, OAW, and OW were similar. (D) A stacked bar plot shows that the binding loci for Oct4, Ash2l-a, and OA are predominantly localized to distal elements (i.e. Distal I and Distal II), while Wdr5-related binding loci (i.e., Wdr5, OW, OAW, and AW) are generally localized to Near elements. (E) Venn diagrams show the corresponding numbers of binding loci for Ash2l-a, Oct4, and Wdr5 (upper) and the numbers of binding loci for the Ash2l-a-Oct4 overlap, Sox2, and Nanog (lower). (F) Aggregation profiles around all Oct4-Ash2l-a co-binding loci show the comparison of binding patterns among stemness-related factors (first panel from left); WARD components (second panel from left); enhancer-binding proteins (second panel from right); and histone marks (first panel from right). (G) Box plots of Ash2l-a, Oct4, Sox2, Nanog, Wdr5, Med1, and H3K27ac ChIP-seq density at Distal II elements in ESCs with or without Ash2l-a knockdown.

FIGS. 4A-4K show that Ash2l-a/Oct4/Sox2/Nanog complex locates on the super-enhancers to regulate enhancer activation. (A) A Venn diagram shows the corresponding numbers of Ash2l-a-bound genes at Distal II elements (4817 genes, obtained from ChIP-seq data), genes that were affected by Ash2l-a knockdown (9393 genes, obtained from microarray data; 7597 genes, obtained from RNA-seq data). Ash2l-a-bound genes at Distal II elements were detected by ChIP-seq, and the genes that were affected by Ash2l-a knockdown were analyzed by microarray and RNA-seq. A total of 805 genes in the intersection were identified as Ash2l-a-affected genes at Distal II element, including 107 upregulated genes and 698 downregulated genes. (B) A box plot showing the 805 super-enhancer-driven genes that are affected by Ash2l-a knockdown at Distal II elements. (C) Categorization of the 698 genes that bound by Ash2l-a at Distal II elements and down-regulated upon Ash2l-a knockdown into the binding targets of Ash2l-a-Oct4 (AO; 608 genes), Ash2l-a-Wdr5 (AW; 64 genes), and Ash2l-a-Oct4-Wdr5 (AOW; 46 genes). (D) A Venn diagram shows the numbers of binding loci for the Ash2l-a-Oct4 overlap, Sox2, Nanog at Distal II elements. (E) Gene Ontology analysis shows the downregulated genes in Ash2l-a knockdown ESCs and co-bound by Ash2l-a and Oct4 (AO), Ash2l-a and Wdr5 (AW), or Ash2l-a, Oct4 and Wdr5 (AOW) at Distal II elements. (F) Gene set enrichment analysis of the 608 AO co-bound genes at Distal II elements and down-regulated upon Ash2l-a knockdown. These genes include upregulated genes in ESCs (the first on the left) and downstream genes targeted by Oct4, Sox2, and Nanog, respectively (the second/third/fourth on the left). (G) Genome browser tracks showing the ChIP-seq results of Med1, H3K27ac, Oct4, Sox2, Nanog, Ash2l-a, and Wdr5 at Jarid2, Oct4, Sox2, and Nanog enhancers from the existing ChIP-seq database (Upper) RNA-seq results showing the production of enhancer RNA (eRNA) at Ash2l-a-bound super-enhancers (lower). (H) qPCR of the eRNA production levels at super-enhancers of Oct4, Jarid2, and Nanog in ESCs with or without Ash2l-a-knockdown. The eRNA expression at each super-enhancer in Ash2l-a-knockdown ESCs was shown as relative levels to that in ESCs with shCtrl. (I) ChIP-qPCR shows the enrichment of RNA polymerase II and H3K27ac at the super-enhancers of Oct4, Jarid2, and Nanog in ESCs with or without Ash2l-a knockdown. Data were normalized with IgG control and shown as relative enrichment to that in ESCs with shCtrl. (J) Re-ChIP-qPCR analysis revealed the binding relationship of Ash2l-a, Oct4, Sox2, and Nanog at Jarid2, Oct4, Sox2, and Nanog super-enhancer in ESCs with or without Ash2l-a knockdown. The first ChIP-qPCR with anti-Ash2l antibody revealed the direct binding of Ash2l-a at the super-enhancer of Oct4. The second ChIP-qPCR with indicated antibodies showed that Ash2l-a, Oct4, Sox2, and Nanog virtually co-bound to the gene loci at the super-enhancer of Jarid2, Oct4, Sox2, and Nanog. Data were shown as relative fold change to the IgG control. (K) Western blot reveals that Ash2l-a knockdown suppressed the protein levels of Oct4, Sox2, and Nanog, but not p300, Med1, and H3K27ac in ESCs with shAsh2l. Data are presented as mean±SD. *p<0.01.

FIGS. 5A-5F show that Ash2l-a binding motif is crucial for the recruitment of OSN to Jarid2, Oct4, and Nanog super-enhancers. (A) Schematic illustration of the design of sequence-specific sgRNA for blocking of Jarid2, Nanog, or Oct4 super-enhancers using monoallelic silencing (labeled as sgRNA$_{AB}$) or biallelic silencing (labeled as sgRNA$_{AC}$, sgRNA$_{DE}$, sgRNA$_{DF}$, sgRNA$_{GH}$, and sgRNA$_{GI}$). The dCas9 nuclease is targeted to super-enhancer of Jarid2, Nanog, or Oct4 by either set of sgRNA. Three amplicons for each enhancer (Jarid2: R1: enhancer; R2: promoter, R3: desert; Nanog: R4: enhancer; R5: promoter, R6: desert; Oct4: R7: enhancer; R8: promoter, R9: desert) were designed to evaluate protein enrichment in ChIP-qPCR assay. (B) ChIP-qPCR analysis showing the enrichment of indicated protein at Jarid2, Nanog, and Oct4 super-enhancers in ESCs with CRISPRi/dCas9-mediated interference of Ash2l-a binding. ChIP-qPCR analysis with indicated antibodies was conducted in CRISPRi/dCas9-modified ESCs, and the enrichment of each protein at R1-3 regions, R4-6 regions, or R7-R9 regions, was evaluated with specific primers. Data showed that CRISPRi/dCas9-mediated interference of Ash2l-a binding at Jarid2 enhancer (upper), Nanog enhancer (middle), and Oct4 enhancer (lower), specifically increased dCas9 binding and decreased the binding of Ash2l-a, Oct4, Sox2, Nanog, and H3K27ac, to R1, R4, and R7, but not R2, R3, R5, R6, R8, and R9. (C) qPCR results showing the effect of CRISPRi/dCas9-mediated interference of Ash2l-a binding on mRNA expression of Jarid2, Nanog, and Oct4. (D) Western blot showing the effect of CRISPRi/dCas9-mediated interference of Ash2l-a binding on the protein content of Jarid2, Nanog, and Oct4. (E) qPCR shows CRISPRi/dCas9-mediated interference of Ash2l-a binding at indicated enhancers abrogate the upregulation of Jarid2, Nanog, Oct4 transcripts induced by Ash2l-a overexpression. (F) Reporter assay shows that Flag-Ash2l-a and Myc-Oct4 induce a synergistic effect on enhancer activity in Jarid2, Nanog, and Oct4 super-enhancers. The Ash2l-a-mediated enhancement of Jarid2, Nanog, and Oct4 enhancer activation can be abrogated by specific sgRNA for indicated enhancer. Data are presented as mean±SD. *, p<0.01.

FIGS. 6A-6H show that Ash2l-a recruits OSN to Oct4 super-enhancer to modulate Oct4 expression. (A) Western blot shows the restoration of endogenous Oct4, Sox2, and Nanog protein by exogenous introduction of Myc-tagged Oct4, HA-tagged Sox2, and Flag-tagged Nanog in ESCs with Ash2l-a knockdown. To examine the effect of Ash2l-a knockdown on OSN recruitment without affecting cellular protein content of Oct4, Sox2, and Nanog, Myc-tagged Oct4, HA-tagged Sox2, and Flag-tagged Nanog were exogenously introduced into ESCs with or without Ash2l-a knockdown. (B) ChIP-qPCR shows that the binding affinity of exogenously introduced Oct4 (left), Sox2 (middle), and Nanog (right) to the Oct4 enhancer in ESCs with or without Ash2l-a knockdown. Data were normalized with IgG control and shown as relative levels to that in shCtrl-transfected ESCs. (C) ChIP-qPCR reveals that Ash2l-a knockdown decreases Oct4 enrichment to Oct4 enhancer. Gene knockdown in ESCs was conducted with indicated lentivirus-based shRNA, followed by ChIP-qPCR analysis with specific antibodies. ChIP-qPCR shows that knockdown of Ash2l-a hampered Oct4 binding to the enhancer. Data were normalized with IgG control and presented as relative fold changes to the enrichment at enhancer in control ESCs. Data are presented as mean±SD. *p<0.01. (D) (SEQ ID NOS: 31 and 32) ChIP-RT-PCR analysis validates the regulatory effect of Ash2l-a on Oct4 binding ability to Oct4 enhancer. Flag-tagged Ash2l-a variants (Flag-Ash2l$^{WT}$ and Flag-Ash2l$^{W118A}$) and Myc-tagged Oct4 were expressed in HEK293T cells. The amount of each transfected plasmid was indicated at the top. The nuclear extracts from the transfected HEK293T cells were purified and subjected to a ChIP-qPCR assay with indicated antibodies. The co-precipitated sequence of Oct4 enhancer and promoter were analyzed. Flag-Ash2l$^{WT}$ alone directly bound to Oct4 enhancer and promoter (lanes 1 and 6). Increasing amount of Flag-Ash2l$^{WT}$ enhanced Myc-Oct4 binding to Oct4 enhancer (lanes 4 and 5) but not to Oct4 promoter (lanes 9 and 10). Mutation of W118 position of Ash2l-a (Flag-Ash2l$^{W118A}$) abrogated the Ash2l-a effect on Oct4 binding to enhancer (lanes 18-20). The preimmune serum served as a negative control. (E) The design of DNA probes for Ash2l-a-binding site of Oct4 super-enhancer [−15 k] and random sequence. (F) Validating the binding relationship between Ash2l-a and Oct4 at Oct4 super-enhancer by a DNA Affinity pull-down (DAPA) assay. The oligonucleotide probe containing Oct4 super-enhancer sequence was incubated with recombinant Ash2l-a and Oct4 proteins in vitro. The probe was precipitated and the co-precipitated Flag-Ash2l-a and Myc-Oct4 proteins were analyzed by Western blot. Flag-Ash2l$^{WT}$ directly bound to Oct4 probe and enhanced the binding of recombinant Oct4 to Oct4 probe, whereas Flag-Ash2l$^{W118A}$ failed to exert the same effect. (G) A reporter plasmid containing the Oct4 enhancer sequence was transfected into HEK293T cells along with Oct4 and full-length (Ash2l-Full length), truncated (Ash2l-N terminus or Ash2l-C terminus), or mutated (Ash2l$^{W118A}$) Ash2l-a expression plasmids. The luciferase activity representing Oct4 enhancer activity was assayed and shown as relative fold change to that of the empty vector-transfected cells. The Ash2l-Full length and Ash2l-N terminus enhanced Oct4 enhancer activity while Ash2l-C terminus and Ash2l$^{W118A}$ failed to increase Oct4 enhancer activity. (H) Illustrative scheme for the Ash2l-a-mediated Oct4 recruitment to Oct4 super-enhancer. The Ash2l-a-mediated Oct4 recruitment could be abrogated by Ash2l-a knockdown or the point mutation of W118A at Ash2l-N terminus. Data are presented as mean±SD. * p<0.01.

FIGS. 7A-7E show that Ash2l-a-Oct4 interaction via W118 residue governs the overall Ash2l-a-mediated pluripotent network. (A) Illustrative scheme shows the procedure of scRNA-seq. (B) After analyzing transcriptomes from ESCs with Ash2l-a knockdown and simultaneous overexpression of Flag-Ash2l$^{WT}$ or Flag-Ash2l$^{W118A}$, t-distributed stochastic neighbor embedding (t-SNE) was used to reduce dimension for clustering and visualization. The transcriptome of indicated genes was shown. (C) Quantification of the gene transcripts (Ash2l-a, Oct4, Sox2, Nanog, and Jarid2) from ESCs with various Ash2l-a knockdown and simultaneous overexpression of Flag-Ash2l$^{WT}$ or Flag-Ash2l$^{W118A}$. (D) Examining the effect of point-mutation of Ash2l-a W118 residue on the reprogramming efficiency in MEFs. MEFs were reprogrammed with Oct4, Sox2, and Klf4 plus Flag-Ash2l$^{WT}$ or Flag-Ash2l$^{W118A}$. The reprogrammed colonies were stained with alkaline phosphatase, and the numbers of alkaline phosphatase-positive colonies were counted. Data are presented as mean±SD. *p<0.01. (E) Schematic presentation of the working model of Ash2l-a-dependent regulation of super-enhancer activity to modulate the expression of stemness-related genes and pluripotent state. Ash2l-a binds to its binding motifs at the super-enhancers of downstream genes, such as Oct4, Jarid2, and Nanog, and recruits a serial of stemness factors and enhancer-binding proteins to these super-enhancers. This complex creates an open chromatin structure by modifying histone marks, leading to enhanced transcription of the target genes. This enhanced gene expression further contributes to facilitate cell pluripotency and reprogramming.

FIGS. 8A-8D show that the knockdown of Ash2l-a abolished cell reprogramming and inhibited pluripotency. (A) The changes on Ash2l-a and Oct4 mRNA expression were similar upon the pro-differentiation stimulation. The total RNA of ESCs were collected at indicated time after the leukemia inhibitory factor (Lif) withdraw, retinoic acid (RA) addition and the induction of embryoid body (EB) formation. The mRNA expression levels of Ash2l-a and Oct4 in the ESCs were monitored with qRT-PCR. Data are presented as mean±SD. (B) ESCs transfected with shRNA control (shCtrl) or shRNA against Ash2l-a (shAsh2l) were analyzed by immunofluorescent staining to assess the protein expression levels of Rex1 and Oct4. DAPI was used for staining nucleus. Scale bar=100 µm. (C) Western blotting shows the transfection efficiency Oct4/Sox2/Klf4 with or without Ash2l-a on the protein expression of endogenous Ash2l-a, Oct4, and Nanog. α-Tubulin was used as loading control.

FIGS. 9A-9D show that the purified recombinant proteins used for in vitro pull-down assays. (A) Co-immunoprecipitation assay with anti-Ash2l antibody from the 4$^{th}$ fraction chromatography experiment. IgG was used as negative control. The assay demonstrated that Ash2l-a interacts with Wdr5, Rbbp5 and Dpy30. (B) Coomassie blue staining of the input of indicated recombinant proteins used for the in vitro anti-Flag pull-down assays.

Figure 10:
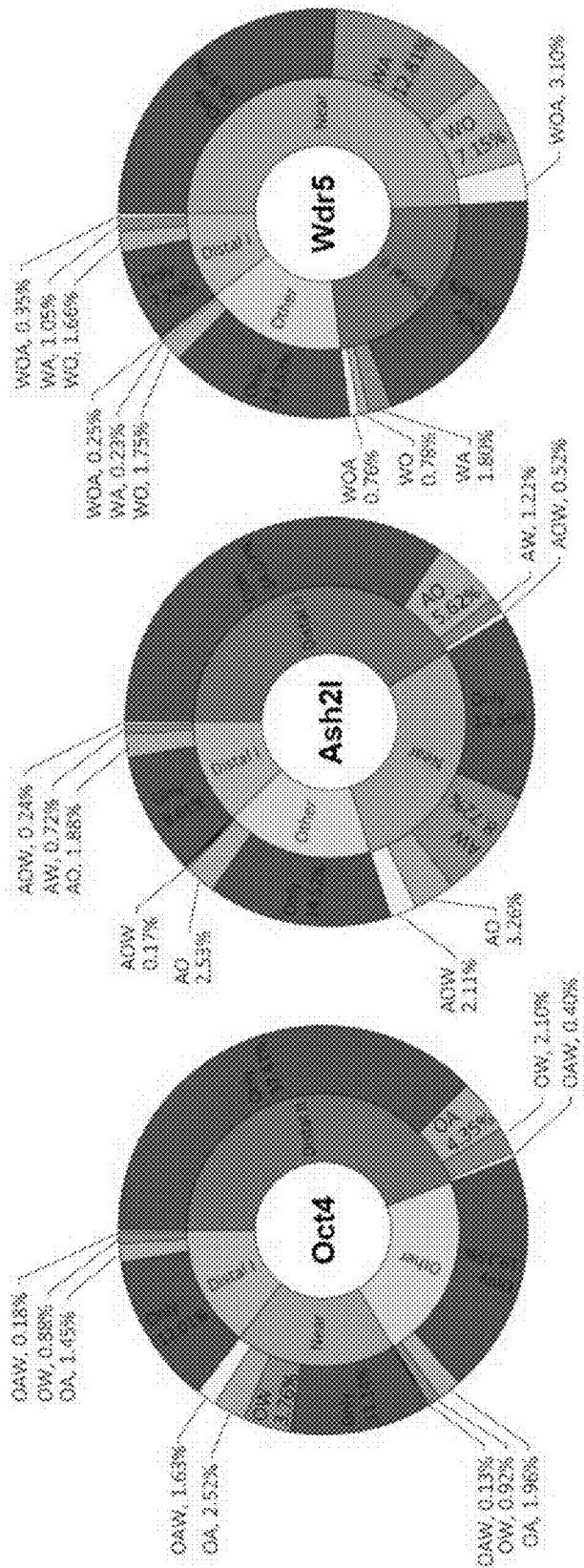

FIG. 10 shows that the comparison of pattern between Ash2l-a and Wdr5 around near and distal Oct4 binding loci. A Venn pie chart showing the percentage of binding for of Oct4, Ash2l-a and Wdr5 at indicated locations (Near, Distal I, Distal II, and Other). The binding patterns between the three proteins at each location were shown in the outer layer of the charts.

FIGS. 11A-11E show that Ash2l-a colocalized with Oct4, Sox2, Nanog, and H3K27ac histone mark at distal regions of downstream genes. (A) ChIP-qPCR analysis of Ash2l-a and H3K27ac bindings at the genomic regions of the pluripotency-related genes selected from the ChIP-seq analysis. The enrichment of indicated protein was normalized to that of IgG. Data are presented as mean±SD. (B) ChIP-qPCR analysis of Ash2l-a, Oct4, Sox2 and Nanog binding to genomic regions associated with the enhancer locus of Oct4 [−15 k], Jarid2 [−26 k], and Nanog [−45 k] in mouse ESCs. The IgG was used as negative control. Data are presented as means±SD. (*, p<0.01). (C) The mRNA expression levels of Oct4, Nanog, Jarid2, and Rbbp5 in ESCs with or without Ash2l-a knockdown. mRNA expression levels in shAsh2l-transfected cells were presented as relative levels to that in shCtrl-transfected cells. Data are presented as mean±SD.

FIGS. 12A-12I show that Ash2l-a binding motif is critical for the recruitment of OSN to Jarid2 and Nanog super-enhancers. (A)(SEQ ID NOS: 33 and 34) Schematic presentation of the reporter plasmid containing Jarid2 promoter and enhancer with or without Ash2l-a-binding motif deletion. (B) (SEQ ID NO: 35 and 36) Schematic presentation of the reporter plasmid containing Nanog promoter and enhancer with or without Ash2l-a-binding motif deletion. (C) Jarid2 reporter plasmid containing intact (upper) or deleted Ash2l-a-binding motif (lower) was co-transfected with Flag-Ash2l$^{WT}$ or Flag-Ash2lW118A with mutated Trp118 residue, and Myc-tagged Oct4 expression plasmid in HEK293T cells. Cells were subjected to a plasmid-ChIP assay with anti-Myc antibodies to precipitate Oct4. Flag-Ash2lWT enhanced the recruitment of Myc-Oct4 to Jarid2 enhancer sequence with intact Ash2l-a-binding motif, but not Flag-Ash2lW118, enhancer containing deleted binding motif or promoter. (D) Cell lysates were subjected to Luciferase activity assay to evaluate the transcription activity of Jarid2. Flag-Ash2lWT and Myc-Oct4 synergistically enhanced the luciferase activity of Jarid2 enhancer with intact Ash2l-a-binding motif (upper), but not that with deleted binding motif (lower). Flag-Ash2lW118A and Myc-Oct4 did not show a synergistic effect on the luciferase activity of Jarid2 enhancer with intact binding motif Data are presented as means±SD. (*, p<0.01). (E) Nanog reporter plasmid containing intact (upper) or deleted Ash2l-a-binding motif (lower) was co-transfected with Flag-Ash2l$^{WT}$ or Flag-Ash2lW118A with mutated Trp 118 residue, and Myc-tagged Oct4 expression plasmid in HEK293T cells. Cells were subjected to a plasmid-ChIP assay with anti-Myc antibodies to precipitate Oct4. Flag-Ash2lWT enhanced the recruitment of Myc-Oct4 to Nanog enhancer sequence with intact Ash2l-a-binding motif, but not Flag-Ash2lW118, enhancer containing deleted binding motif or promoter. (F) Cell lysates were subjected to Luciferase activity assay to evaluate the transcription activity of Nanog. Flag-Ash2lWT and Myc-Oct4 synergistically enhanced the luciferase activity of Nanog enhancer with intact Ash2l-a-binding motif (upper), but not that with deleted binding motif (lower). Flag-Ash2lW118A and Myc-Oct4 did not show a synergistic effect on the luciferase activity of Nanog enhancer with intact binding motif Data are presented as means±SD. (*, p<0.01). (G) (SEQ ID NOS: 37-53) Upper left: Schematic illustration of the design of three sequence-specific sgRNA for monoallelic (sgRNA$_{AC}$) and biallelic (sgRNA$_{AB}$) blocking of Jarid2 enhancer. The Ash2l-a binding sequence is underlined. The dCas9 nuclease is targeted to genomic DNA (chr13:44817812-44817962, distal enhancer of Jarid2) by either sets of sgRNA$_{AB}$ and sgRNA$_{AC}$. Three locations (R1: Jarid2 enhancer, R2: Jarid2 promoter, and R3: desert) were designed to evaluate protein enrichment in ChIP assay. Lower left: Schematic illustration of the design of three sequence-specific sgRNA for monoallelic (sgRNA$_{DF}$) and biallelic (sgRNA$_{DE}$) blocking of Nanog enhancer. The Ash2l-a binding sequence is underlined. The dCas9 nuclease is targeted to genomic DNA (chr6:122652519-122652659, distal enhancer of Nanog) by either sets of sgRNA$_{DE}$ and sgRNA$_{DF}$. Right: The design of sgRNA sequences for sgRNA$_{AB}$, sgRNA$_{AC}$ sgRNA$_{DE}$, and sgRNA$_{DF}$. (H) Quantitative RT-PCR was used to validate the effect of CRISPRi/dCas9-mediated blocking of the Ash2l-a binding motif at Jarid2 and Nanog enhancers. sgRNA$_{AC}$ and sgRNA$_{DE}$ were used for the blocking. The CRISPRi/dCas9-mediated blocking decreased the expression of Jarid2 and Nanog.

FIGS. 13A-13G show that Ash2l-a is crucial for the binding of Oct4, Sox2, and Nanog to the Jarid2 and Nanog enhancers. (A-B) ESCs were exogenously expressed Myc-tagged Oct4, HA-tagged Sox2 and Flag-tagged Nanog with or without shAsh2l as indicated, and subjected to ChIP-qPCR assays. Data were normalized by IgG control and shown as relative fold change of enrichment to that in control cells (first lane). ChIP-qPCR data show that the binding affinity of exogenously introduced Oct4 (left), Sox2 (middle), and Nanog (right) to the Jarid2 (A) and Nanog (B) enhancers in ESCs. (C) ESCs with or without Ash2l-a knockdown were subjected to a ChIP assay to evaluate the effect of Ash2l-a expression on the binding of p300 and Med1 on Jarid2, Nanog and Oct4 distal enhancers. ChIP-qPCR results showed that knockdown of Ash2l-a hampered the p300 and Med1 binding to Jarid2 enhancer. All data are presented as means±SD. (*, p<0.01).

DETAILED DESCRIPTION OF THE INVENTION

Unless defined otherwise, all technical and scientific terms used herein have the same meaning as commonly understood by a person skilled in the art to which this invention belongs.

As used herein, the singular forms "a", "an", and "the" include plural referents unless the context clearly dictates otherwise. Thus, for example, reference to "a sample" includes a plurality of such samples and equivalents thereof known to those skilled in the art.

The invention provides a method for preparing induced pluripotent stem cells (iPSCs) from somatic cells, comprising:
(a) transfecting or transducing the transcription factor Ash2l into isolated somatic cells, or contacting or exposing isolated somatic cells with/to the transcription factor Ash2l-a, which the isolated somatic cells can express transcription factor; and
(b) culturing the isolated somatic cells as obtained in step (a) under appropriate conditions, thereby converting the somatic cells into iPSCs and maintaining pluripotency and self-renewal ability.

The invention also provides a use of Ash 2l for driving an enhancer activation, upregulation of a stemness gene, and maintaining the pluripotent circuitry to regulate pluripotency and self-renewal in pluripotent stem cells.

In addition, the invention provides an enhancer-bound Ash2l-a/OSN complex for driving enhancer activation, governing pluripotency network and stemness circuitry in pluripotent stem cells.

It was confirmed in the present invention that Ash2l-a tends to co-localize with OSN at the distal regions of Jarid2, Oct4, Nanog, and Sox2 in ESCs. These regions are enriched with super-enhancer features such as the acetylation of H3K27 (H3K27ac), the enrichment of Med1, Chd7, and p300. Ash2l-a recruits OSN to super-enhancers to form the Ash2l-a/OSN complex that subsequently promotes the expression of pluripotency-related genes and cellular reprogramming. Blocking Ash2l-a binding to super enhancers using CRISPRi/dCas9 system abrogates OSN recruitment to the super-enhancers and hinders the enhancer activation of several pluripotency-related genes. In the Ash2l-a/OSN complex, Ash2l-a interacts with Oct4 through its W118 residue. The W118A point mutation of Ash2l-a specifically disrupts Ash2l-a-Oct4 interaction, and subsequently led to the reduction of OSN recruitment to super-enhancers and the activation of these super-enhancers. Moreover, based on single cell NGS analysis, W118 mutated Ash2l-a could not rescue the expression of OSN in Ash2l-a-depleted ESC cells. Taken together, our findings unravel a Wdr5-independent regulatory role of Ash2l-a in modulating pluripotency through recruiting OSN to super-enhancers, shedding lights on stem cell epigenetics and reprogramming circuitry.

The present invention will now be described more specifically with reference to the following examples, which are provided for the purpose of demonstration rather than limitation.

Examples

Experimental Procedures

Cell Culture

Mouse embryonic fibroblasts (MEFs) were isolated from 13.5 d.p.c. embryos and maintained in DMEM containing 10% FBS and penicillin/streptomycin. Mouse ES cell lines ESD3 and reprogrammed iPSC were routinely cultured and expanded on mitotically inactivated MEFs ($5 \times 10^4$ cells/cm$^2$) in 10 cm culture plate (BD) in the presence of 0.3% leukemia inhibitory factor in an iPSC medium, consisting of DMEM (Sigma Aldrich) supplemented with 15% FBS (Invitrogen), 100 mM MEM, nonessential amino acids (Sigma Aldrich), 0.55 mM 2-mercaptoethanol (Gibco), and antibiotics (Invitrogen). iPSCs and mouse pluripotent teratocarcinoma stem cell line SCC-PSA1 (purchased from Bioresource Collection and Research Center) were maintained on MEFs feeders in serum-containing media at 5% $CO_2$ and 37° C. A potent retrovirus packaging cell line Plat-E was used to produce retroviruses and maintained in DMEM containing 10% FBS and penicillin/streptomycin. All cell cultures were maintained at 37° C. with 5% $CO_2$.

shAsh2l Expression Constructs and Lentiviral Transduction

Stable depletion of Ash2l-a and Oct4 in ESCs was obtained using small hairpin RNA (shRNA) probe for the mouse gene Ash2l-a and Oct4. Control ESCs steadily expressed pLKO.1-shLuc (shCtrl). shRNA was co-transfected with lentivirus packaging plasmids (psPAX2, pCMV-VSVg) into Plat-E cells. Lentivirus was generated by transfecting Plat-E cells at $1 \times 10^6$ per 10 cm dish with Transfection Reagent TransIT-LT1® (Mirus). Supernatants were collected 48 hr after transfection and then were filtered. Subconfluent cells were infected with lentivirus in the presence of 8 μg/ml polybrene (Sigma Aldrich). Infected cells were selected with puromycin (2 μg/ml) until control uninfected cells were completely dead. Quantitative RT-PCR and immunoblotting were used to validate the knockdown efficiency by shRNAs. The information on vectors is listed in Table 1.

TABLE 1

| Sequences of shAsh2l-1, Ash2l-2 and shOct4 | |
|---|---|
| shRNA | Sequence (5' to 3') |
| shAsh2I-1 | AAGGAGCAGCGATGGCGGC (SEQ ID NO: 54) |
| shAsh2I-2 | AAAAGGAGCAGCGATGGCGGC (SEQ ID NO: 55) |
| shOct4 | GAAGGATGTGGTTCGAGTA (SEQ ID NO: 56) |

For Oct4 ChIP-qPCR in Oct4 knockdown ESCs and the Ash2l-a rescue experiments, shRNA-resistant plasmids were used to exogenously overexpress myc-tagged Oct4 and Flag-tagged Ash2l$^{WT}$ or Ash2l$^{W118A}$.

Ash2l-a mutation variants were created using the QUICK-CHANGE® site-directed mutagenesis kit (Agilent), according to manufacturer's instructions. With the two-step overlap extension PCR method on p3×Flag Ash2l-a plasmid, the 5' and 3' portions of wild-type Ash2l-a were amplified in separate reactions using external primers with internal mutagenic primers.

Cell Reprogramming

Mouse iPSCs were generated from MEFs derived from 13.5d old embryos of C57/B6 mice as described previously (19). The day before transduction, Plat-E cells were seeded in 100 mm dish. Next day, either pMXs-based retroviral vectors (pMXs-Oct4, Sox2, Klf4, and c-Myc), or pBabe-based retroviral vectors (pBabe-Ash2l), or pLKO-based lentivirus vectors (pLKO-shCtrl, and shAsh2l) were introduced into Plat-E cells using calcium phosphate transfection. 24 hours after the transfection, the medium was replaced with normal culture medium. MEFs were seeded 24 hours before virus infection. After 24 hours, virus-containing supernatants, derived from these Plat-E cultures, were filtered through a 0.45 mm cellulose acetate filter (Pall) and supplemented with 8 µg/ml polybrene (Sigma Aldrich). Target cells were incubated with the virus/polybrene-containing supernatants for 1 hour, 2250 rpm centrifugation. After infection, the supernatants were replaced with fresh medium. After 48 hours, the virus-containing supernatants were collected again after the second infection. Six days after the infection, the infected cells were transferred onto a 6-wells plate with mitomycin C-treated MEF feeders in the presence of 0.3% leukemia inhibitory factor in ESC medium. pMXs-Oct4, pMXs-Sox2, pMXs-Klf4, and pMXs-c-Myc, pBabe-control vectors were purchased from Addgene. pBabe-Ash2l were constructed in our lab. shCtrl, shAsh2l were from National RNAi Core Facility Platform.

Alkaline Phosphatase Staining

For detecting the alkaline phosphatase (AP) activity, cells were fixed with 80% alcohol and then stained using the Vector Blue Alkaline Phosphatase Substrate Kit III (Vector Laboratories) according to the manufacturer's instructions.

Chimera Mouse Production by Blastocyst Injection

The introduction of mouse OSKA-iPSCs (derived from C57BL 6J strain, black coat color) into mouse blastocysts, derived from the C57BL 6J-Tyrc2J strain (albino) was performed as previously described with some modifications (20). The adult chimeras were confirmed by coat color, demonstrating that OSKA-iPSCs were competent to produce adult chimeric mice. This study was assisted by Transgenic Mouse Model Core Facility, Academic *Sinica*, Taiwan.

Gel Filtration (Size Exclusion Chromatography)

Gel filtration was performed in AKTA prime plus System according to manufacturer's manual (GE Healthcare Life Sciences). Briefly, nuclear extracts (10-20 mg) were applied to an S400 (HIPREP™ 16/60 SEPHACRYL®) gel filtration column (Amersham Biosciences), fractions were collected, concentrated, and subjected to SDS-PAGE, followed by Western blotting and detection with the indicated antibodies. The S400 gel filtration column was calibrated using the protein standards purchased from GE Healthcare (cat #28-4038-41 LMW and cat #28-4038-42 HMW), and the relative sizes of the indicated complexes were marked above the corresponding fractions. Overall, seven fractions of ESC nuclear extracts were obtained. The fractionated samples were collected and assigned for immunoprecipitation and western blot to examine the protein content and interaction among interested proteins.

Molecular Docking

For identify the potential interacting residues mediating AO-interaction, we collected the protein structure of Ash2l-a (3RSN), Oct4 (3L 1P), Sox2 (1GT0) and Nanog (2VI6) as receptorligand complex. We individually subjected Oct4, Sox2 or Nanog with Ash2l-a protein into ZDOCK3.0.2. The docking results were plotted by using PyMOL 2.3 software.

In Vitro Protein Binding

For binding assays, 100 ng of GST-tagged proteins, including Oct4, Sox2, Nanog, and Rbbp5 were coupled to Glutathione SEPHAROSE™ 4B beads and incubated with recombinant Ash2l-a variants overnight at 4° C. in binding buffer (20 mM Tris-HCl [pH8.0], 150 mM NaCl, 0.1% Tween 20) supplemented with 0.5% BSA. After washing three times with reaction buffer, bound proteins were eluted and analyzed by immunoblotting.

CRISPRi Mediated Inhibition in Mouse ESCs

The plasmids were obtained from Academia Sinica. For transient transfection experiments, HEK293 cell line was transfected in 6-well plates using TransIT-LT1© transfection reagent (Mirus) according to the manufacturer's protocol. HEK293T cells were transfected with 1 µg expression plasmid (pX334-D10A, Addgene) that will stably drive the expression of dCas9 and the first sgRNA. Meanwhile, the same cells were simultaneously transfected with the expression plasmid to drive the expression of the second sgRNA. The supernatant of the culture from these transfected cells were collected and used for the infection of ESCs. pX334-D10A plasmid harbors a puromycin resistance gene, therefore we shifted the ESCs to the culture medium supplemented with 1 µg/ml puromycin and changed the medium every two days. After two weeks puromycin selection, we performed a quantitative RT-PCR to validate the expression of dCas9 and various sgRNAs, and used the ChIP-qPCR assay to examine the enrichment of dCas9 in the indicated gene loci. The information of sgRNA design is listed in Table 2.

TABLE 2

Primers for construction.

| Application | Name | Cutting site | Region |
|---|---|---|---|
| Reporter assay | Jarid2-Promoter | XhoI/HindIII | |
| | Jarid2-Enhancer | BamH1/SalI | |
| | Nanog-Promoter | XhoI/HindIII | |
| | Nanog-Enhancer | BamH1/SalI | |
| | Oct4-Promoter | XhoI/HindIII | |
| | Oct4-Enhancer | BamH1/SalI | |
| Pull down assay | Oct4-GST | | |
| | Sox2-GST | | |
| | Nanog-GST | | |
| | Rbbp5-GST | | |
| | Flag-Ash2l-N | | |
| | Flag-Ash2l-C | | |
| | Flag-Ash2l-F | | |

Luciferase Activity Assay

The enhancer regions of Jarid2 (chr13: 44817842-44817933) or Nanog (chr6: 122652519-122652659) were cloned by PCR amplification of genomic DNA from C57BL/6 mice and then inserted into the BamH1/Sal1 sites of the pGL4.19 vector to generate the plasmid pGL4.19-Jarid2 parental construct. The various enhancer fragments and mutated fragments were cloned by PCR amplification of mouse genomic DNA into the pGL4.19-promoter, containing the minimal Jarid2 promoter. HEK293T cells were grown in 12-wells tissue culture plate to 70% confluence and then cotransfected with 0.2 µg pMXs and pMXs-Ash2l or pMXs-Oct4 in the presence of 0.2 µg pGL4.19-Jarid2 promoter firefly luciferase or pGL4.19-Nanog enhancer firefly luciferase and 10 ng SV40 Renilla luciferase plasmids (Promega). Trans-LT1 transfection kit was used for transfection of ESCs or HEK293T cells. 24 h after transfection, cells were harvested in 100 µl of reporter lysis buffer and then subjected to a dual luciferase assay. Luciferase activity was detected using the DUAL-GLO®Luciferase Assay luciferase kit (Promega) according to manufacturer's instructions. Firefly luciferase activity was normalized to Renilla luciferase activity, and data are represented as the mean and standard deviation of three independent experiments, each performed in triplicate.

RNA Extraction and Real-Time Quantitative PCR Analysis

Total RNA was isolated from the pluripotent cells using the RNEASY® kit (Qiagen, Valencia, CA). 1 µg of total RNA was subjected to first-strand complementary DNA synthesis by using the SuperScript© III Reverse Transcriptase Kit (Invitrogen) as directed by the manufacturer. PCRs were performed using the SYBR® Green method in an ABI 7900 sequence detection system (Applied Biosystems) according to the manufacturer's guidelines. Primers (listed in Table 3) were designed using PRIMER EXPRESS™ 2.0 software (Applied Biosystems, Foster City, CA). All primer specificity was computer tested (BLAST, National Center for Biotechnology Information, Bethesda, MD) by homology search with the human genome and later confirmed by dissociation curve analysis. The expression level of each gene was normalized to the endogenous expression level of Gapdh and experimental control through $_{\Delta\Delta}$Ct methods.

TABLE 3

Primers for quantitative RT-PCR

| Gene symbol | Forward (5' to 3') | Reverse (5' to 3') |
|---|---|---|
| Ash21 | AAGGAGGAGGCCAGG ACGAGACCAA (SEQ ID NO: 1) | AGCCCGCCTGGGTAT CCATCACTTC (SEQ ID NO: 2) |
| Oct4 | CATGCATTCAAACTG AGGCACC (SEQ ID NO: 3) | AATGATGAGTGACAG ACAGGCC (SEQ ID NO: 4) |
| Sox2 | GGTGCAAAAAGAGGA GAGTA (SEQ ID NO: 5) | TTTGCGTTAATTTGG ATGGG (SEQ ID NO: 6) |
| Nanog | AACTCTTCTTTCTAT GATCTTTCC (SEQ ID NO: 7) | CTTCCTCAGAACTAG GCAAA (SEQ ID NO: 8) |
| Wdr5 | GAAGGGCCACAGTAA CTACGTCTT (SEQ ID NO: 9) | GAGGCCATCATAGCT ACTGGAAAC (SEQ ID NO: 10) |
| Gapdh | CTCATGACCACAGTC CATGC (SEQ ID NO: 11) | TTCAGCTCTGGGATG ACCTT (SEQ ID NO: 12) |
| Jarid2 | ACAAACGTGACTTCC AACAT (SEQ ID NO: 13) | AAAACTACATCAGCG AAACG (SEQ ID NO: 14) |
| Cdx2 | ACGTGAGCTACCTTC TGGACAAG (SEQ ID NO: 15) | GTACTGCGGAGGACT GACAAAGT (SEQ ID NO: 16) |
| Fgf5 | AGGGGATTGTAGGAA TACGA (SEQ ID NO: 17) | CAGTCATCCGTAAAT TTGGC (SEQ ID NO: 18) |
| Nestin | ACCTCAAGATGTCCC TTAGTCTGG (SEQ ID NO: 19) | GGAGTCTCAAGGGTA TTAGGCAAG (SEQ ID NO: 20) |
| Pax6 | TCTTTCTTGGCCAGC AAAAGTTA (SEQ ID NO: 21) | TTGTGAACAACTGCA AAACACTT (SEQ ID NO: 22) |
| dCas9 | ACAAGAAGTACAGCA TCGGCCT (SEQ ID NO: 23) | ATTTCTTGCTGGGCA CCTTG (SEQ ID NO: 24) |
| Nanog [-45 k] | CCTTTCAGTTGTCTC CCGAAAC (SEQ ID NO: 25) | GGGGGACGTTTCACA TTCAA (SEQ ID NO: 26) |
| Oct4 [-15 k] | TCTACTTGCAGTTCT GCTGAGTCC (SEQ ID NO: 27) | TGTGAATGGGGACCA ATGGT (SEQ ID NO: 28) |
| Jarid [-26 k] | AATAGGCTGGCCTCA AACTCAG (SEQ ID NO: 29) | CCAGTCCACAGCACT GAAAAGA (SEQ ID NO: 30) |

Transcriptome Analysis

For microarray analysis, Affymetrix Mouse Genome M430 2.0 microarrays (Affymetrix) were used. Total RNA extraction, array hybridization, and feature selection were performed as described (19). Heatmaps were created using dChip software. Classical multidimensional scaling was performed using the standard function of the R. The average-linkage distance was used to assess the similarity between 2 groups of gene expression profiles as described (19). The difference in distance between 2 groups of sample expression profiles to a third was assessed by the comparison of corresponding average linkage distances (the mean of all pairwise distances [linkages] between members of the 2 groups concerned). The error on such a comparison was estimated by combining the standard errors (the standard deviation of pairwise linkages divided by the square root of the number of linkages) of the average-linkage distances involved.

For NGS data, we firstly used PEAT to remove adapter contamination and then aligned the clean reads to the mm10 genome using RNAStar (version) to retain junction reads before sending into Cufflink (version) with gene annotation by GENCODE (version) for normalized expression level estimation (i.e., FPKM). We only considered lncRNAs and protein-coding mRNAs in this work. The $\mathrm{Log}_2$ fold change of the FPKM value of each gene between samples was used to identify up- or down-regulated genes over the control. The PCA analysis was applied to several samples with all the FPKM values as features and three top principal components were extracted and used as the new basis to further discover the similarity between samples.

Gene Ontology, Pathway, and Network Analysis

The filtered gene lists were subjected to gene ontology enrichment analysis using the AltAnalyze bundled module GO-Elite. GO-Elite implements an over-representation statistical inference that can identify significantly enriched GO categories with nuclear proteins. GO terms with a z-score >2, a permutation of p<0.01 and three or more regulated proteins for each GO term were reported as significant. Gene enrichment analysis by the DAVID 2008 Bioinformatics Resources.

ChIP-Seq Analysis

ChIP-seq datasets, if not generated by us, were downloaded from either the GEO or ENCODE portal. We processed and analyzed all the datasets from scratch if the raw FASTQ files were available. For some datasets, of which only the alignment results (in SAM or BED format) were available, we used the Liftover tool to convert the coordinates to mm10 genome assembly. The raw reads were aligned to mm9 genome using Bowtie, allowing at most one mismatch and only one alignment was randomly picked for multi mappers. The peaks were called using MACS 1.4 along with corresponding input background. Different shiftsize parameters were used according to the type of antibodies (shiftsize=100, for transcription factors; and shiftsize=150, for histone marks; other parameters were set as default). The peaks from replicates were first called with a relaxed p-value cutoff (0.001) and then pooled together; only those peaks that overlapped with peaks called from at least one other replicate were kept. The aggregation plots and heatmaps were generated similarly as described (21).

We used FIMO (22) to infer the binding sites in each peak of Oct4. These Oct4 binding sites that had other peaks of different transcription factors or histone modifications called from ChIP-seq data in the vicinity were deemed co-binding. Each binding site was assigned to the nearest protein-coding gene according to the distance from the midpoint of the binding site to the transcription start site. The binding site-gene pairs were categorized into four groups by the distance in between: near (<1 kb), distal I (between 1-2 kb), distal II (between 2-200 kb), and others (>200 kb). The GO term enrichment analysis was performed using Panther web service (23).

RNA-Seq and Microarray

Total RNA was prepared as described (19). Strand-specific libraries were generated from 500 ng total RNA using the TRUSEQ™ Stranded Total RNA Library Prep Kit (Illumina). cDNA libraries were pair-end sequenced (50 bp) on an Illumina HISEQ™ 2000. Reads were aligned to the mouse genome (NCBI37 mm9) with TopHat v1.3.3 and allowed one alignment with up to two mismatches per read. mRNA RPKM values were calculated using Seqmonk's mRNA quantitation pipeline. We selected the genes with the following criteria: the minimum RPKM higher than 10 units, fold change>1.5-fold or <0.85-fold from knockdown control sample, and the expression was significantly different from knockdown control sample (P<0.01).

For the measurement of enhancer RNA (eRNA) production, we used the nascent RNA sequencing analysis to assess eRNA production as previously described by Core and Hah, with brief modifications (24,25). Generally, the application scope of nascent RNA sequencing analysis ranged from enhancer identification to a thorough enhancer-centered analysis. Nascent RNA sequencing analysis includes a novel algorithm to prioritize enhancers by integrating RNA-seq data with the binding profiles of regulators to narrow down interesting enhancers for further experiments. The algorithm can simultaneously undergo the gene analysis of known genes and the enhancer-related analysis, including detecting, quantification and annotation of enhancers.

For microarray analysis, we selected the genes with the following criteria: the minimum log 2 intensity higher than 4, fold change >1.5-fold or <0.75-fold from knockdown control sample, and the expression was significantly different from knockdown control sample (P<0.01).

Chromatin Immunoprecipitation Coupled with Quantitative Real-Time PCR (ChIP-qPCR)

Sub-confluent cells were re-suspended in PBS at the density of $1 \times 10^7$ cell/ml and crosslinked at room temperature with 1% formaldehyde for 8 min, and then quenched by incubating in 125 mM glycine. ChIp-qPCR experiments were performed according to the manufacturer's instruction (Diagenode). Chromatin was sonicated using a BIORUPTOR® (Diagenode) according to the manufacturer's protocol and examined with electrophoresis assay. Sonicated chromatin was diluted to a final volume of 1000 μl in ChTP lysis buffer supplemented with protease inhibitors before pre-clearing with 30 μl protein A DYNABEADS® (Thermo Fisher Scientific) for 2 h at 4° C. Chromatin samples were incubated with antibody overnight at 4° C. Immunocomplexes were captured by incubating with 30 μl protein A DYNABEADS® for 4 h at 4° C. Sample was washed three times with CHiP lysis buffer, and eluted in elution buffer (50 mM Tris, PH 8, 10 mM EDTA, 1% SDS) at 65° C. for 15 min. For Re-ChIP-qPCR assay, the samples after de-crosslink were subjected to qPCR assay and remains were diluted with ChTP lysis buffer. Diluted remains were subjected to second round immunoprecipitation against the second protein. The DNA sample was incubated overnight at 65° C. to reverse crosslinks, diluted 2-fold in 50 mM Tris, PH 8, plus 10 mM EDTA, and then sequentially digested with RNase A for 2 h at 37° C. and proteinase K at 55° C. DNA sample was extracted with phenol/chloroform/isoamyl alcohol and ethanol precipitated. Then, DNA enrichment was quantified by real-time PCR (ABI 7900) using SYBR® Green Master Mix (Thermo Fisher Scientific). The antibodies and primers used in ChTP-qPCR assays are listed in supplementary tables s4 and s6. Occupancy was quantified using qPCR and normalized to input DNA. ChIP-Seq libraries were prepared using the Kapa LTP library preparation kit (Kapa Biosystems). Reads were aligned to the mouse genome (NCBI37/mm9) with Bowtie2. Homer was used for motif discovery in sequences+100 bp from the CHIP-seq peaks.

TABLE 4

Antibody List

| Gene symbol | Application | Host | Catalog no. | Company |
|---|---|---|---|---|
| Ash2l | IF, ChIP | Mouse | ab50699 | Abcam |
| Ash2l | IP | Mouse | sc81184 | Santa Cruz |
| Ash2l | WB | Rabbit | A300-489A | Bethyl Laboratories |
| Oct4 | ChIP | Goat | sc8628 | Santa Cruz |
| Oct4 | IF | Rabbit | 5677S | Cell signaling |
| Oct4 | IP, WB | Goat | sc8628 | Santa Cruz |
| Sox2 | WB | Mouse | 4900 | Cell signaling |
| Nanog | WB | Rabbit | 8822s | Cell signaling |
| Wdr5 | IF | Rabbit | 13105S | Cell signaling |
| Wdr5 | WB | Rabbit | ab22512 | Abcam |
| α-Tubulin | WB | Mouse | CP06-100UG | Merck Millipore |
| Klf4 | | | | |
| Rbbp5 | | | | |
| Dpy30 | IF | Rabbit | A304-296A | Bethyl Laboratories |
| Flag-tag | ChIP | Mouse | F1804 | Sigma |
| Flag-tag | WB | Mouse | F1804 | Sigma |
| H3K27ac | ChIP | Rabbit | ab4729 | Abcam |
| H3K27ac | WB | Rabbit | ab4729 | Abcam |
| myc-tag | ChIP | Mouse | 2276S | Cell signaling |
| myc-tag | WB | Mouse | 2276S | Cell signaling |
| HA-tag | ChIP | | | ChIP |
| Nanog | Flow | | | |
| p300 | ChIP | Rabbit | 4771 | Cell signaling |
| Med1 | ChIP | Rabbit | A300-793A | Bethyl Laboratories |
| RNA Pol II | ChIP | Mouse | 17-620 | Merck Millipore |

Alexa Fluor 568 conjugated anti-rabbit (1:300, Invitrogen) or FITC conjugated anti-rabbit (1:300, Invitrogen), lysates were incubated with isotype IgG (catalog no. sc-2027; Santa Cruz) or antibody specific for Oct4 (5677S, Cell Signaling), Sox2 (23064S, Cell Signaling), Nanog (8785S, Cell Signaling), Ash2l (A300 - 489A, Bethyl Laboratories), Wdr5 (13105S, Cell Signaling), H3K27ac (8173, Cell Signaling) and Myc-tag (2276S, Cell Signaling).

Immunofluorescence Staining

IF staining was performed as previously described (19). Briefly, cells were fixed with 4% paraformaldehyde, permeabilized in 1% TRITON™ X-100 and blocked with 5% FBS. Cells were stained with primary antibodies, and then incubated with ALEXA FLUOR® 568 conjugated anti-rabbit (1:300, Invitrogen) or FITC conjugated anti-rabbit (1:300, Invitrogen), and cell nuclei were counterstained with DAPI (Invitrogen). Details of antibodies can be found in Table 4. Cells were then washed with PBS and photographed under a fluorescence microscope (Olympus).

Western Blot and Immunoblotting

Western blot was performed as previously described (19). Immunoblotting was performed using the primary antibodies described in Table 4. Secondary antibodies used in this study were listed as following: bovine anti-rabbit IgG-HRP (catalog no. 7077S; Cell signaling) and chicken anti-mouse IgG-IRP (catalog no. 7076S; Cell signaling). Immunoblots were visualized by the chemiluminescence detection system.

For immunoprecipitation, cells were generally disrupted with lysis buffer (20 mM Tris-Cl buffer [pH 7.6], 1 mM EDTA, 120 mM NaCl, 10 mM β-glycerophosphate, 1 mM NaF, 1 mM $Na_3VO_4$ and 0.5% TRITON™ X-100) supplemented with protease inhibitors (250 mM PMSF, 5 µg ml pepstatin A, 10 µg ml leupeptin and 5 µg ml aprotinin). For samples from gel filtration, we used CENTRICON® (Millipore) to concentrate and desalt the fraction of elute. Cleared sample solution was obtained by centrifugation at 12 000 rpm for 30 min at 4° C., and 0.5-1.5 mg of the sample was used for immunoprecipitations. For identify interacting complex of Ash2l-a protein, sample was added into primary antibody for 2 h at 4° C. followed by 2 h of further incubation with protein—A/G-SEPHAROSE™ beads. After washing three times with the lysis buffer, immunoprecipitated proteins were eluted from the beads by boiling for 5 min in SDS-PAGE sample buffer and analyzed by immunoblotting.

DAPA Assay

The biotinylated DNA fragments were incubated with streptavidin beads (S-1638; Sigma, St Louis, MO, USA) at 4° C. overnight and washed three times with DAPA buffer (137 mM NaCl, 2.7 mM KCl, 7.7 mM $NaH_2PO_4$, 1.5 mM $KH_2PO_4$, 0.1% NP-40, 1 mM EDTA, 10% glycerol, 1 mM dithiothreitol). Subsequently, the DNA-conjugated beads were incubated with 2 mg of cell lysates and 10 µg of Poly dI-dC (Sigma; P4929) at 4° C. overnight. Following the incubation, 30 µl of streptavidin-agarose beads (Millipore) was added to the reaction and incubated at 4-C for 1 h. The beads were then collected by centrifugation and washed four times with DAPA buffer containing 0.5% NP-40. The pulled down complexes were then resolved by 15% SDS-PAGE and analyzed by Western blotting. The DNA probe sequences are listed in FIG. 6.

Single Cell RNA-Seq

ScRNA-seq libraries of shCtrl, shash2l, shAsh2l+WT and shAsh2l+W118A were generated using the 10× genomics Chromium Controller Instrument (10× Genomics) and Chromium™ Single Cell 30 Reagent Kits v2 according to manufacturer's instructions. RNA of every single cell was reverse transcribed and index using the C1000 Touch Thermal cycler with 96-Deep Well Reaction Module. One thousand cells were loaded on a Chromium controller single-cell instrument to first generate single-cell Gel Bead-In-Emulsions (gems). After the GEMS were breaking, cDNA of every single cell was barcoded, purified and amplified. After ligated with adaptors, the cDNA was converted into 3'RNA-seq libraries by using PCR amplification. The libraries were then sequenced using Illumina Sequencing.

In Vitro Pull-Down Assay

Full length Oct4, Sox2, Nanog, and Rbbp5 were cloned into the pGex-5X1 plasmids (Addgene). Ash2l-a variants (full-length, N-terminus and C-terminus) were cloned into the p3×Flag plasmids (Sigma Aldrich). The plasmids were transformed into BL21 *Escherichia coli*. The GST-tagged OSN recombinant proteins were expressed and purified with Glutathione (GSH)-SEPHAROSE™ beads (Amersham Biosciences, Piscataway, NJ). Flag-tagged recombinant Ash2l-a variants were expressed and purified with anti-Flag beads (A2220, Sigma-Aldrich). The purified recombinant Ash2l-a variants that were bound to anti-Flag beads were further incubated with GST-tagged recombinant OSN proteins for 2 hours at 4° C. ambient temperature. After the incubation, the pull-down mixture was washed twice by PBS buffer to remove unbound proteins. Five hundred µg/ml of 3× Flag peptide (F4799, Sigma-Aldrich) was used to elute the 3× Flag-tagged Ash2l-a variants and their interacting GST-tagged proteins. Subsequently, the eluted protein mixture was subjected to SDS-PAGE analysis. The SDS-PAGE gel was stained by Coomassie blue for identifying the interaction between Flag-tagged Ash2l-a variants and GST-tagged OSN proteins.

Flag-Peptide IP

Flag-tagged peptides were conjugated to Flag-beads for individual IP experiments. One mg of cell extract was dissolved in IP lysis buffer and incubated with anti-Flag antibody-conjugated beads (A2220, Sigma-Aldrich) for 2 hours at 4° C. Beads were then washed thrice by IP buffer and eluted by boiling in 30 µl SDS-containing protein loading buffer. Twenty µl of eluted sample was assigned for each Western blot with 5% input. Flag-tagged beads without peptide conjugation was used as a negative control.

Nuclear Extraction, Size Exclusion Chromatography, and CoIP

Nuclear extraction was performed according to the manual instruction. Biochemical fractionation of ESC extracts into seven fractions was performed as described previously (Ang et al., 2011). Briefly, ESCs were lysed with lysis buffer and applied onto S400 column (HIPREP™ 16/60 Sephycryl). Size exclusion chromatography in S400 column was performed using AKTA prime system according to the manufacturer's instruction (GE). The S400 column was calibrated using the protein standards purchased from GE Healthcare (cat #28-4038-41 LMW and cat #28-4038-42 HMW), and the relative sizes of the indicated complexes were marked above the corresponding fractions. The fractionated samples were collected and assigned for Western blot to examine the levels of various proteins, i.e. Ash2l-a, OSN, and WRD. The fractionated samples were then concentrated, dialyzed and re-suspended in IP buffer, and then subjected to immunoprecipitation to analyze the interaction between Ash2l-a and indicated protein(s).

Teratoma

All animal procedures were performed in accordance with the Taipei Veterans General Hospital Animal Committee, and the principles of Laboratory Animal Care. Teratoma assay was performed as described previously (19). Briefly, approximately $1 \times 10^6$ cells were injected subcutaneously into the right hind leg of immuno-compromised NOD-SCID mice (The Jackson Laboratory). Teratomas were excised 7 weeks post-injection, fixed overnight in formalin, embedded in paraffin, sectioned and stained with hematoxylin and eosin.

Statistical Analysis

Data were expressed as mean±SD. One-way ANOVA was used to detect significant difference. When a significance was detected, post hoc Tukey test was performed using SPSS (SPSS 12.0; SPSS, Chicago, IL). The criterion for significance was set as $p<0.01$. Data were plotted using GRAPHPAD PRISM® program (GRAPHPAD PRISM® 5.0; GraphPad, San Diego, CA).

Results

Ash2l-a is Crucial for Reprogramming and Pluripotency Maintenance.

Figure 1B:
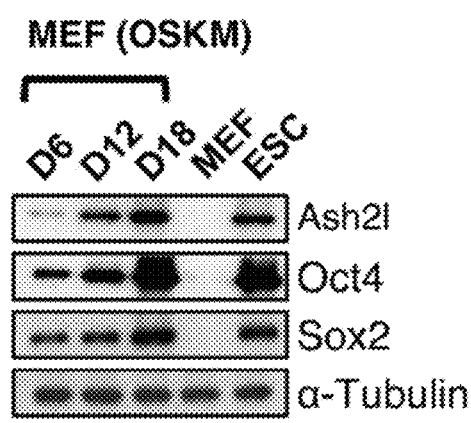
Figure 1C:
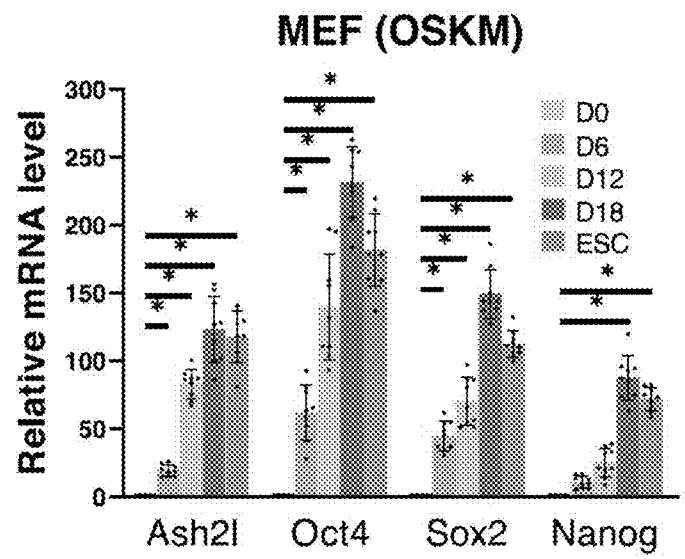
Figure 8A:
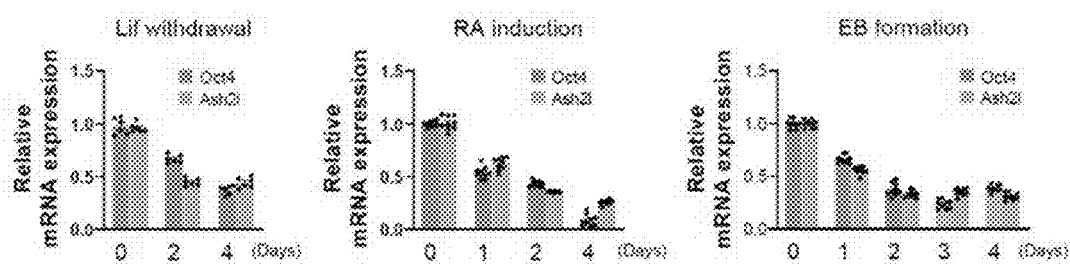

Master transcription factors such as Oct4, Sox2, and Nanog (OSN) orchestrate the epigenetic landscape to regulate pluripotency and cellular reprogramming (8). The expression of these master pluripotency factors is also tightly controlled by epigenetic regulation during differentiation and reprogramming. To elucidate the involvement of Ash2l-a in the regulation of the pluripotent state and reprogramming, we first analyzed the protein expression of Ash2l-a, Wdr5, and OSN stemness factors in pluripotent stem cells. OSN, Ash2l-a, and Wdr5 were all highly expressed in pluripotent stem cells including ESCs, induced pluripotent stem cells (iPSCs) and teratocarcinoma stem cells (PSA-1), but not in mouse embryonic fibroblasts (MEFs) (FIG. 1A). Differentiation stimuli, including retinoic acid (RA) treatment, LIF withdrawal, and induction of embryoid body formation, led to a decline of Oct4 and Ash2l-a mRNA expression levels in iPSCs (FIG. 8A). During the Oct4/Sox2/Klf4/c-Myc (OSKM)-induced reprogramming process, Ash2l-a and stemness factors including Oct4, Sox2, and Nanog, were all upregulated both at their protein and mRNA levels in a time-dependent manner (FIGS. 1B and 1C).

Figure 1D:
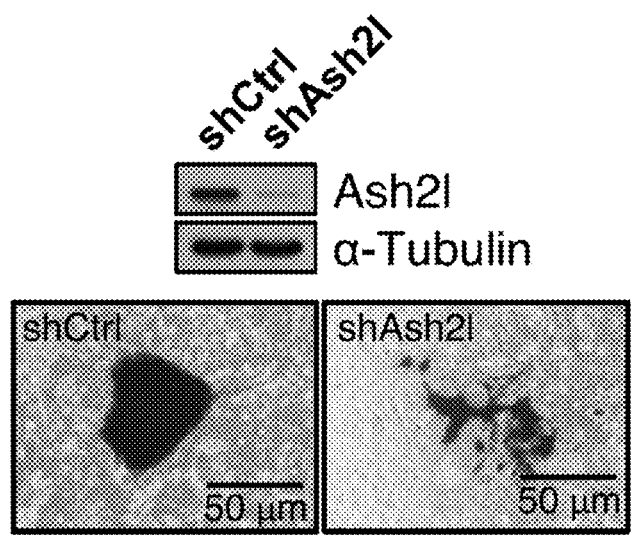
Figure 1E:
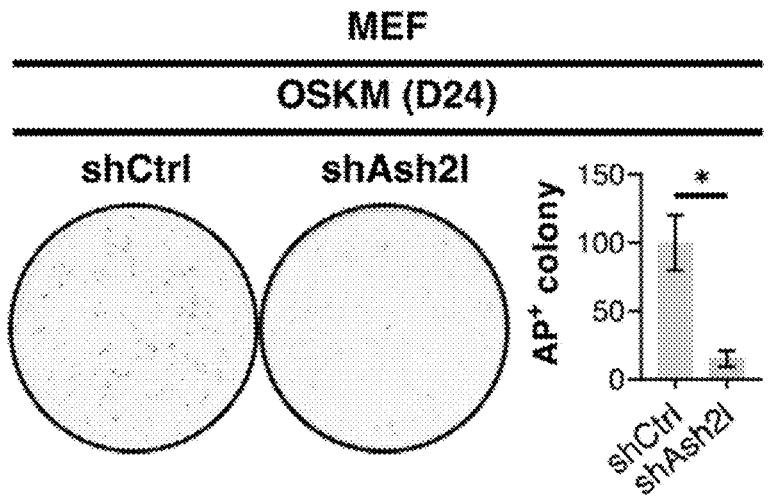
Figure 1F:
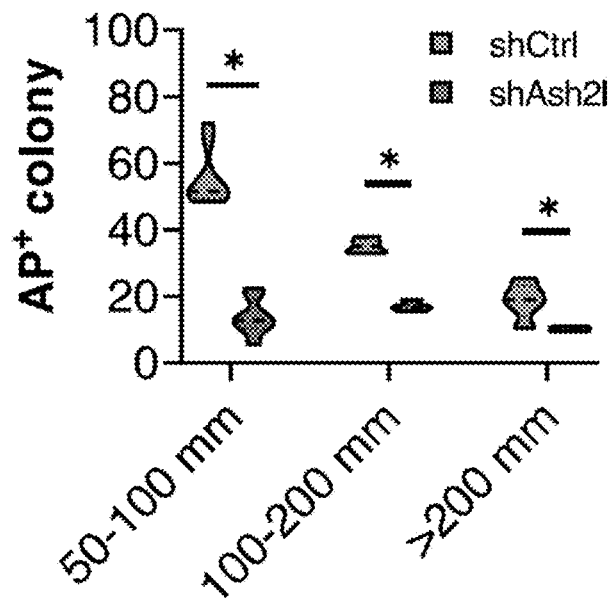
Figure 1G:
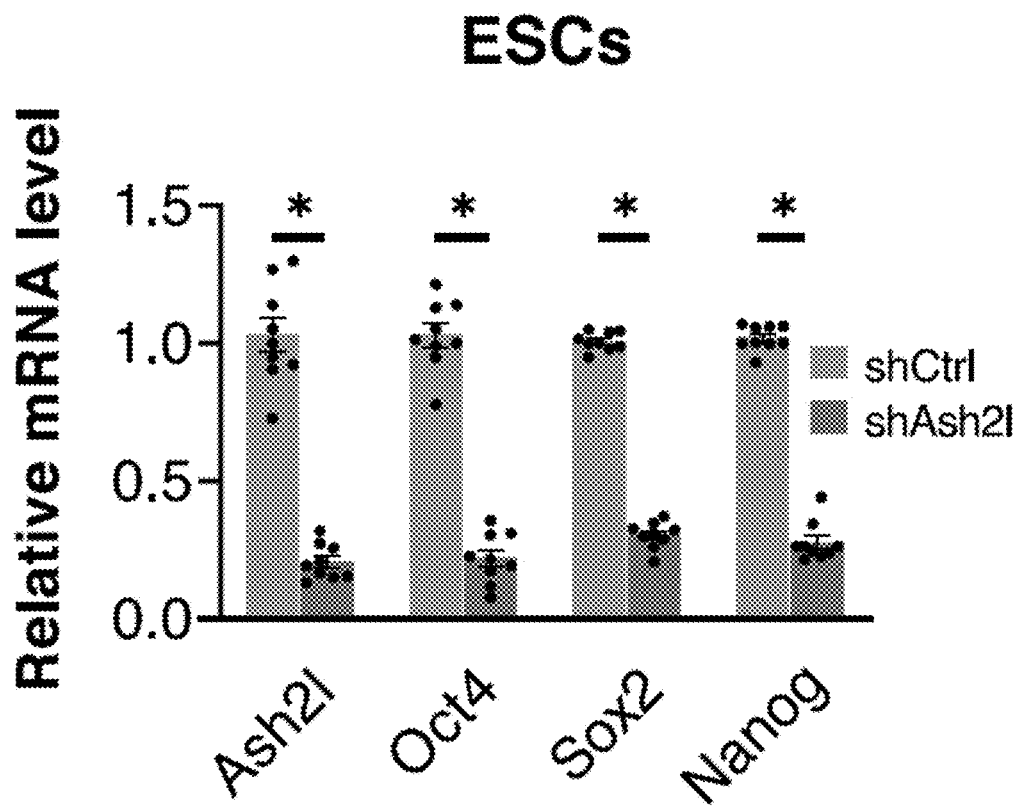
Figure 1H:
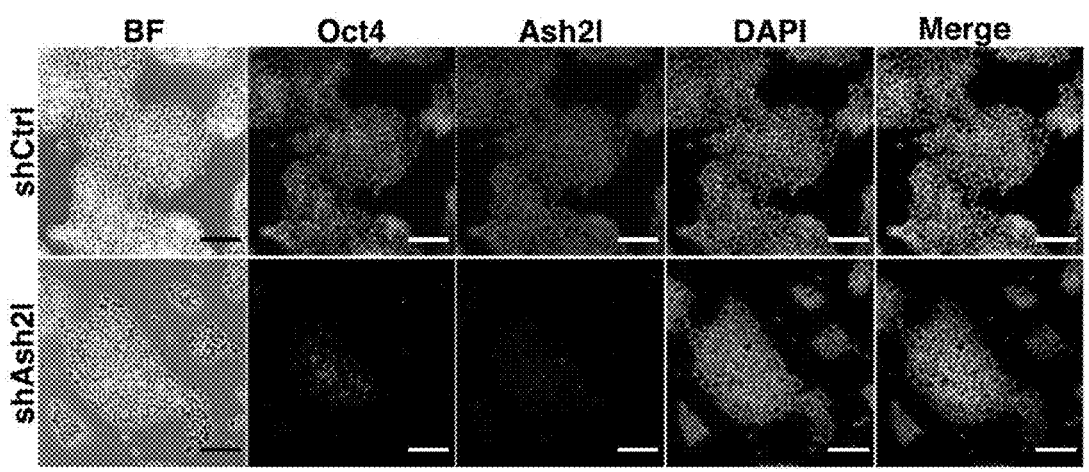
Figure 1I:
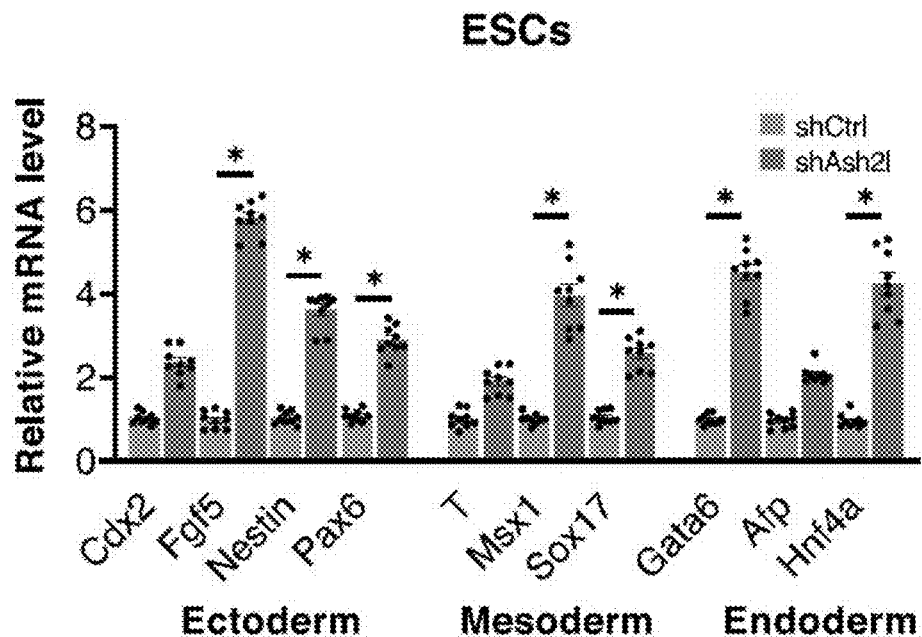
Figure 8B:
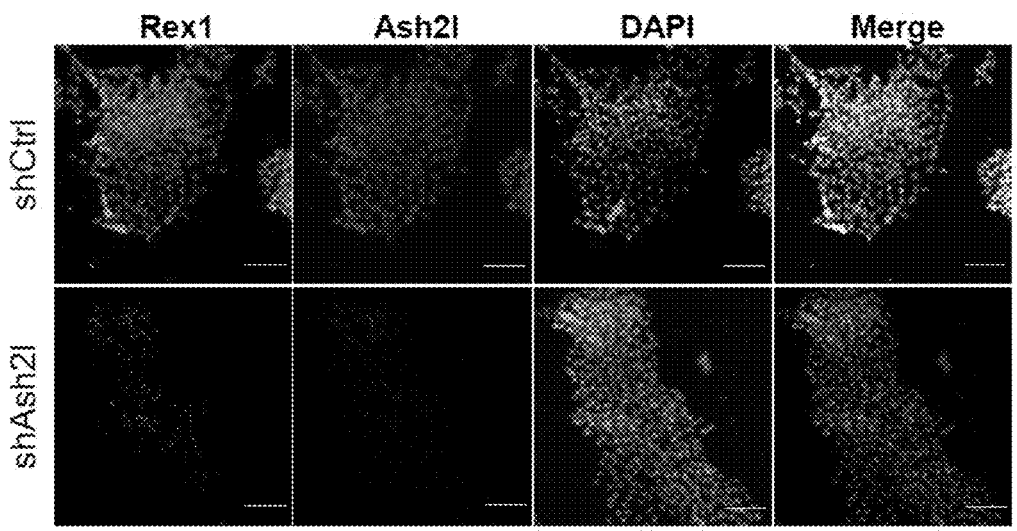
Figure 8C:
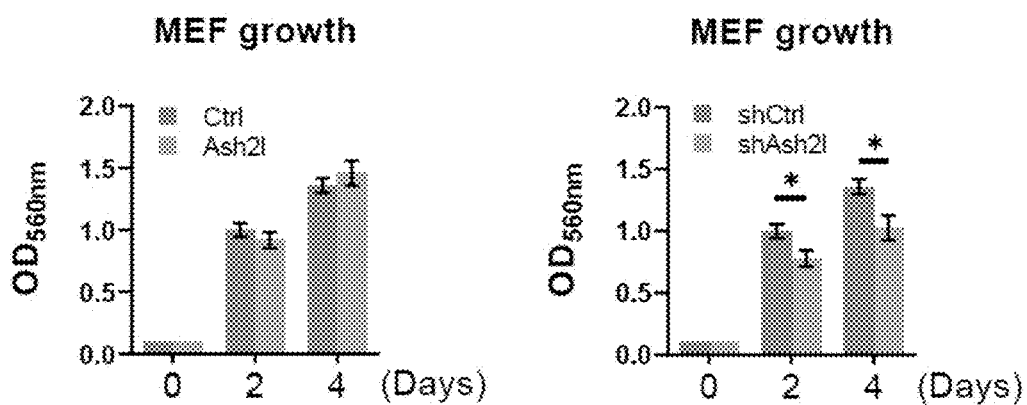
Figure 8D:
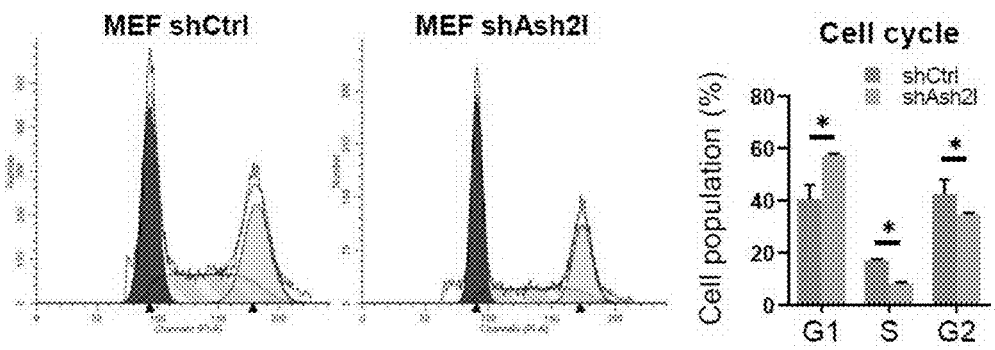

To examine the role of Ash2l-a in reprogramming, we first knocked down Ash2l-a expression in MEFs using a shRNA against its transcript and then subjected these MEFs to OSKM-mediated reprogramming (FIG. 1D). At Day 12 after the reprogramming, the Ash2l-a-knockdown MEFs formed smaller colonies and exhibited lower alkaline phosphatase (AP) activity, compared with scrambled shRNA-infected control cells (FIG. 1D, lower panel). At day 24 post-reprogramming, depletion of Ash2l-a significantly reduced the efficiency of iPSC generation in OSKM-infected MEFs (FIG. 1E). Meanwhile, Ash2l-a knockdown tended to reduce the colony numbers of OSKM-reprogrammed iPSCs at all given size (FIG. 1F). These effects induced by Ash2l-a knockdown on these reprogrammed MEFs suggested that Ash2l-a serves a role in the regulation of pluripotency. We further tested the effect of Ash2l-a knockdown in ESCs, another cell type that carries all pluripotent cell signatures. In ESCs, inhibition of Ash2l-a suppressed the mRNA expression levels of Oct4, Sox2, and Nanog (FIG. 1G). Immunofluorescence also revealed that ESCs infected with shAsh2l became flat, lost their ESC morphology, and largely reduced the numbers of Oct4-positive cells (FIG. 1H). The numbers of Rex1-positive cells were also decreased (FIG. 8B). Meanwhile, Ash2l-a knockdown simultaneously increased the levels of several differentiation-related genes that are closely associated with tridermal differentiation (FIG. 1I; ectoderm: Cdx2, Fgf5, Nestin, Pax6; mesoderm endoderm: T, Msx1, Sox17; endoderm: Gata6, Afp, HNF4α). Furthermore, in MEFs, Ash2l-a overexpression showed no obvious effect on MEF growth, while Ash2l-a knockdown led to an ~20% decrease in MEF growth (FIG. 8C), accompanied with a mild G1-phase cell cycle arrest (FIG. 8D). These data indicated that Ash2l-a serves a regulatory role in pluripotency.

Figure 1J:
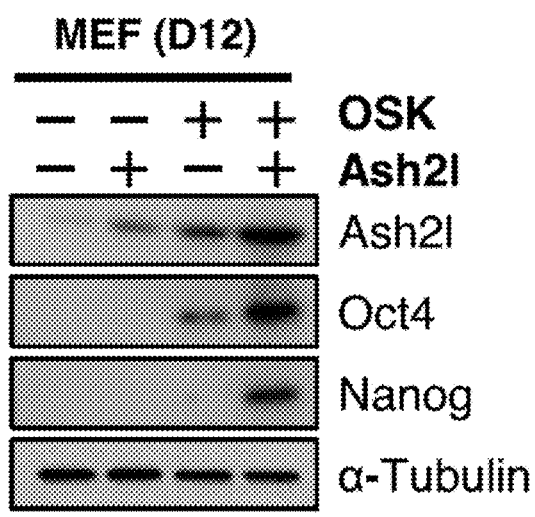
Figure 1K:
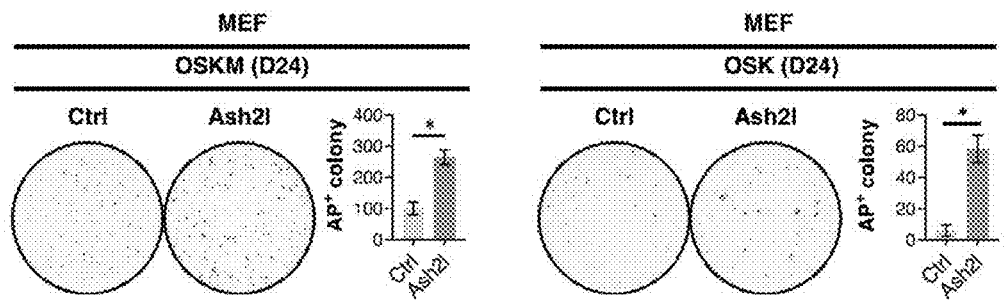
Figure 1L:
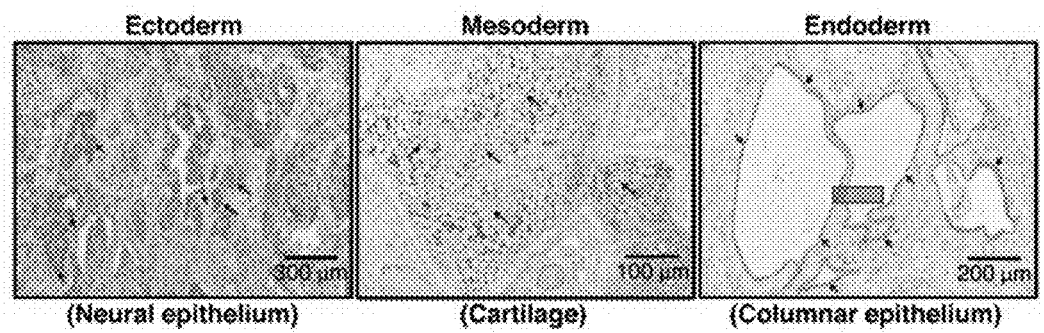
Figure 1M:
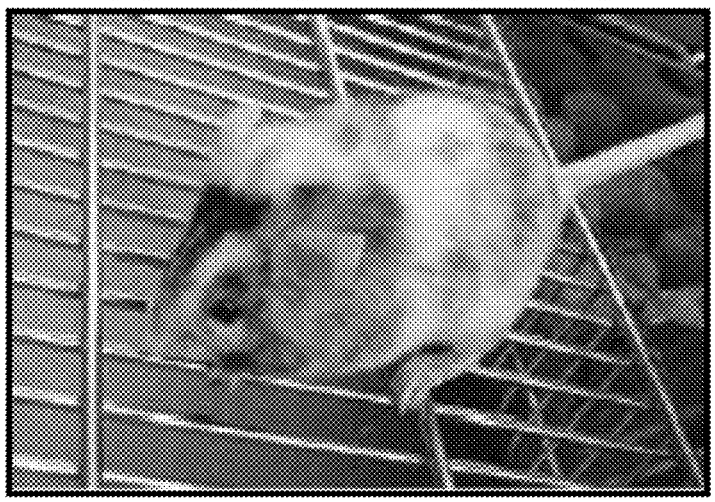

To validate the role of Ash2l-a in regulating pluripotency, we further manipulated Ash2l-a levels by overexpression in MEFs, and examined the effect of Ash2l-a overexpression on the expression of Oct4 and Nanog, and the efficiency of iPSC generation. Western blot analysis at day 12 post-reprogramming showed that, overexpression of Ash2l-a alone was not sufficient to increase the Oct4 and Nanog protein amount (FIG. 1J). However, in MEFs Ash2l-a co-infected with Oct4/Sox2/Klf4 was able to enhance the protein expression of Oct4 and Nanog (FIG. 1J). At day 24 post-reprogramming, Ash2l-a overexpression significantly increased the efficiency of iPSC generation in OSKM-infected MEFs (FIG. 1K, left). Moreover, even without c-Myc, Ash2l-a overexpression still enhanced the efficiency of iPSC generation from Oct4/Sox2/Klf4-infected MEFs, compared with MEFs infected with only Oct4/Sox2/Klf4 (FIG. 1K, right). To test pluripotency in vivo, iPSCs reprogrammed by transfection of Oct4/Sox2/Klf4 plus Ash2l-a (OSKA-iPSCs) were implanted into the subcutaneous space of immune-compromised mice. Six weeks after transplantation, ex vivo biopsies and hematoxylin and eosin staining revealed the teratoma formation in the neuronal epithelium (ectoderm), cartilage and keratinocytes (mesoderm), and smooth muscle (endoderm; FIG. 1L). Moreover, we injected the iPSCs induced by Oct4/Sox2/Klf4 plus Ash2l-a into blastocytes and then transferred these blastocytes to the uteri of pseudopregnant recipient mice. The coat color of the resultant mice indicated that OSKP-iPSCs were competent to produce chimeric mice (FIG. 1M). Collectively, these findings highlighted the crucial role of Ash2l-a in regulating the pluripotency and the establishment of stem cell identity in pluripotent stem cells.

Ash2l-a Forms a Complex with OSN in the Absence of Wdr5.

Figure 2A:
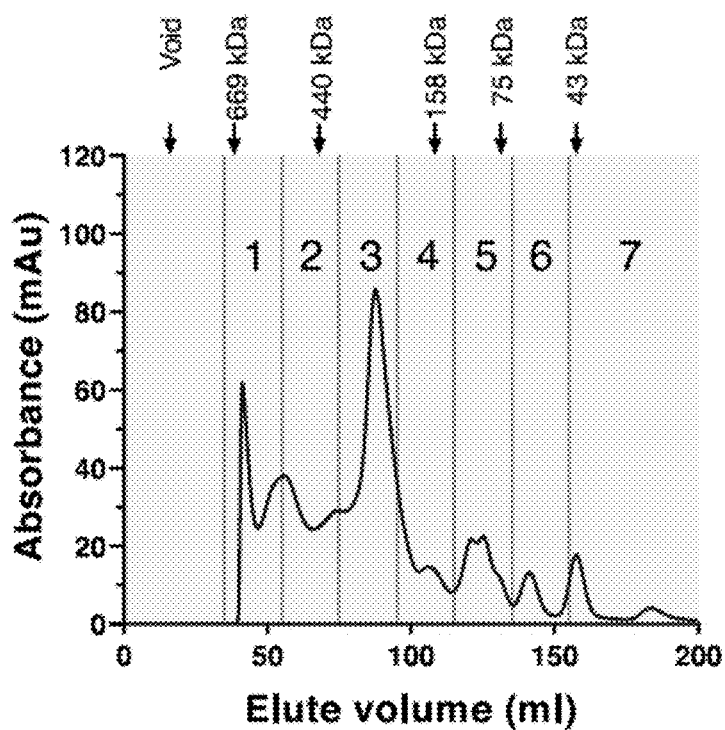
Figure 2B:
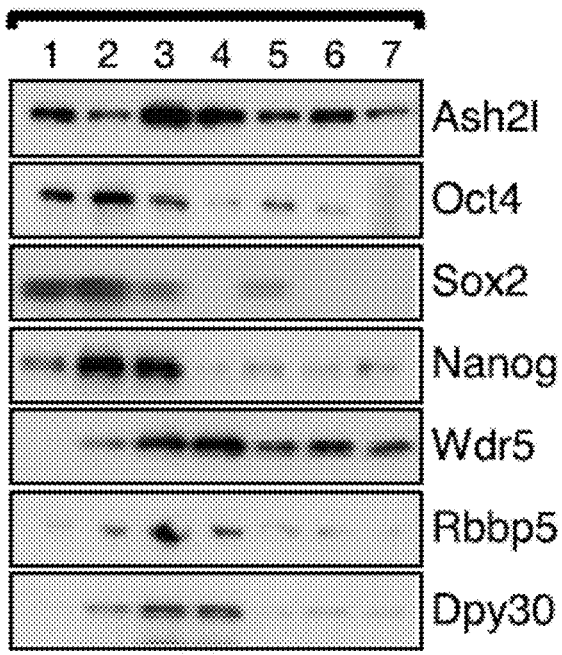
Figure 2C:
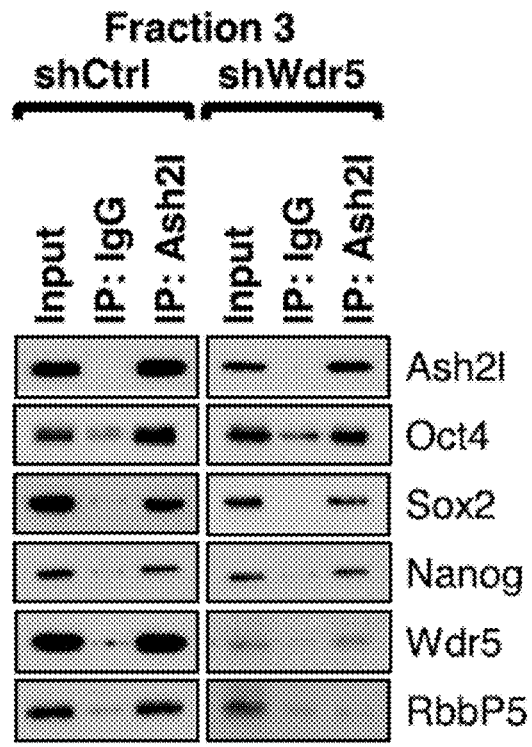
Figure 9A:
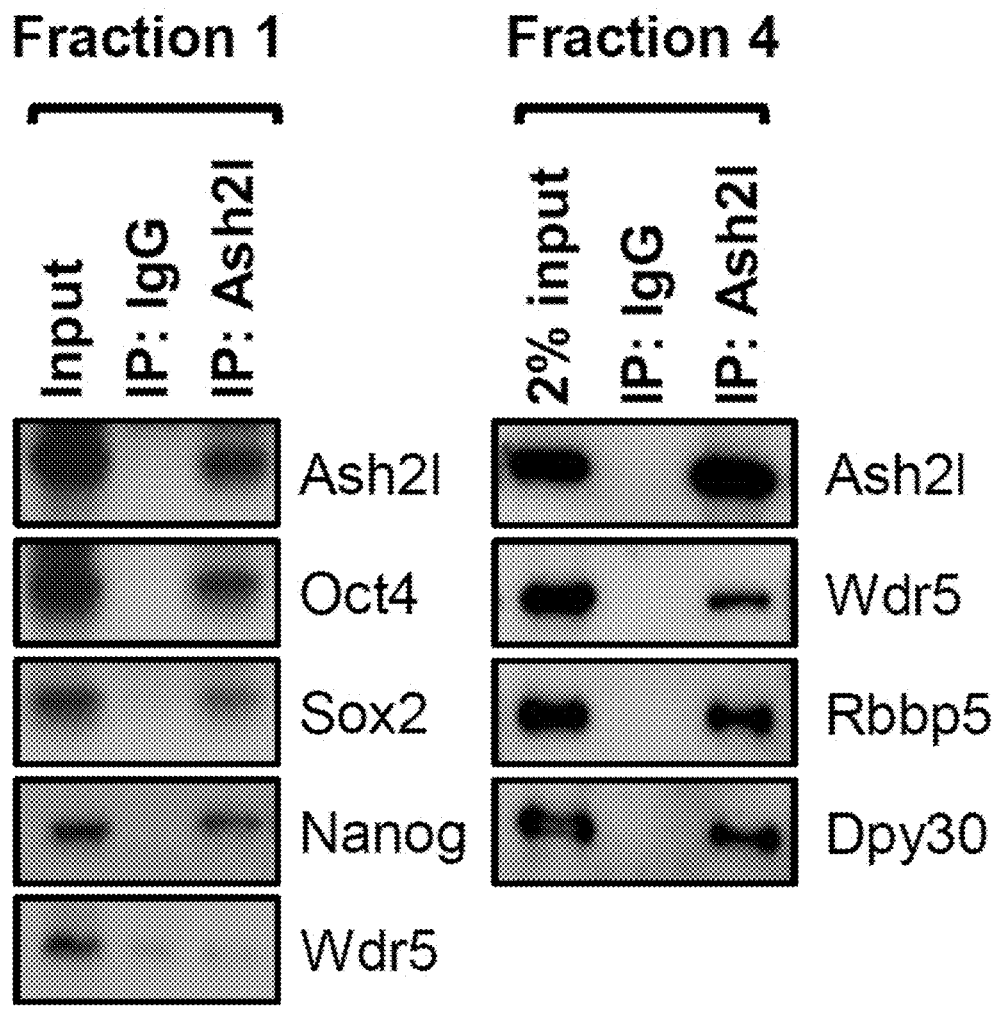
Figure 9B:
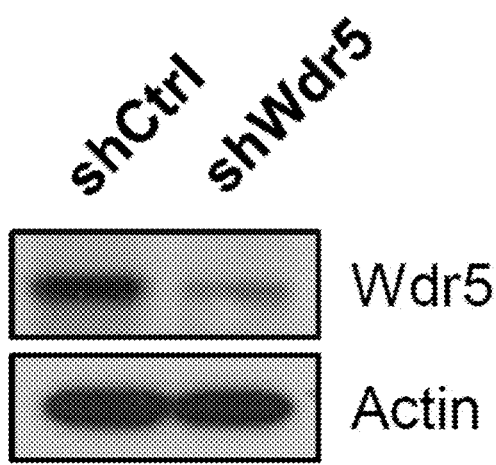

To further understand the role of Ash2l-a in stemness regulation, we used gel filtration analysis (FIG. 2A) followed by Western blot to investigate the profiles of molecular complexes in the nuclei of ESCs (FIG. 2B). We separated the ESC nuclear extracts into seven fractions based on the filtration order. OSN was abundant in fractions 1 to 3 (OSN-enriched fractions), whereas Wdr5, Rbbp5, and Dpy30 (WRD) were enriched in fractions 3 to 4 (WRD-enriched fractions) (FIG. 2B). Subsequently, we assessed these OSN-enriched (fraction 1), OSN/WRD-enriched (fraction 3), and WRD-enriched fractions (fraction 4) in an immunoprecipitation assay. In fraction 1 (an OSN-enriched fraction), we found an interaction between Ash2l-a and OSN (FIG. 2A and FIG. 9A). Note that the expression of Wdr5 was extremely low or barely undetectable in fraction 1 (FIG. 9A). In line with previous report (14,15), an interaction between Ash2l-a and WRD was observed in fraction 4 (FIG. 9A). To elucidate whether Wdr5 affects Ash2l-a-OSN interaction, we repeated the gel filtration and fractionation experiments in the nuclear extracts of ESCs with or without Wdr5 knockdown to examine the molecular complexes profiles (FIG. 2C). We compared the interaction between Ash2l-a and other interacted proteins in the OSN/WRD-enriched fraction (fraction 3) from ESCs infected with shCtrl or shWdr5 (FIG. 2C). Wdr5 knockdown efficiency was confirmed by Western blot (FIG. 9B). And in the absence of Wdr3, Ash2l-a still interacted with OSN (FIG. 2C), indicating the OSN/Ash2l-a complex occurred independently of Wdr5.

Figure 2D:
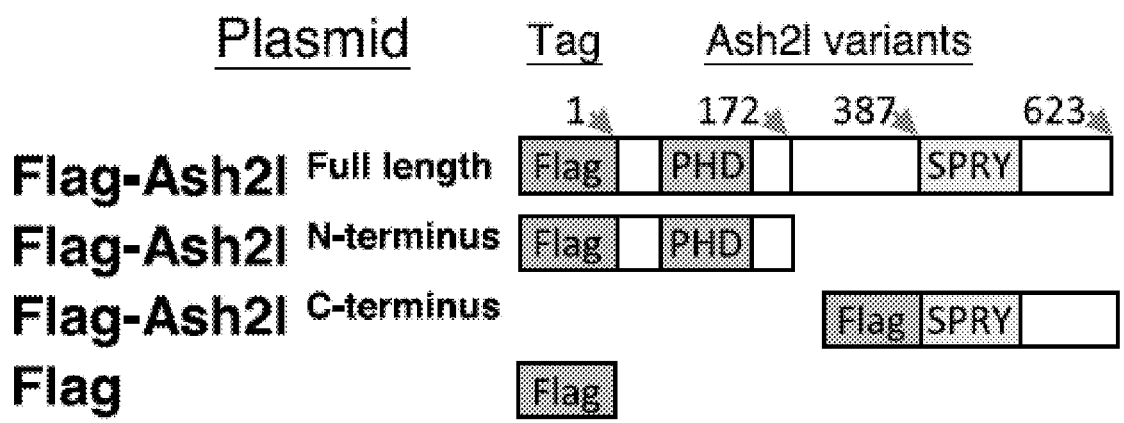
Figure 2E:
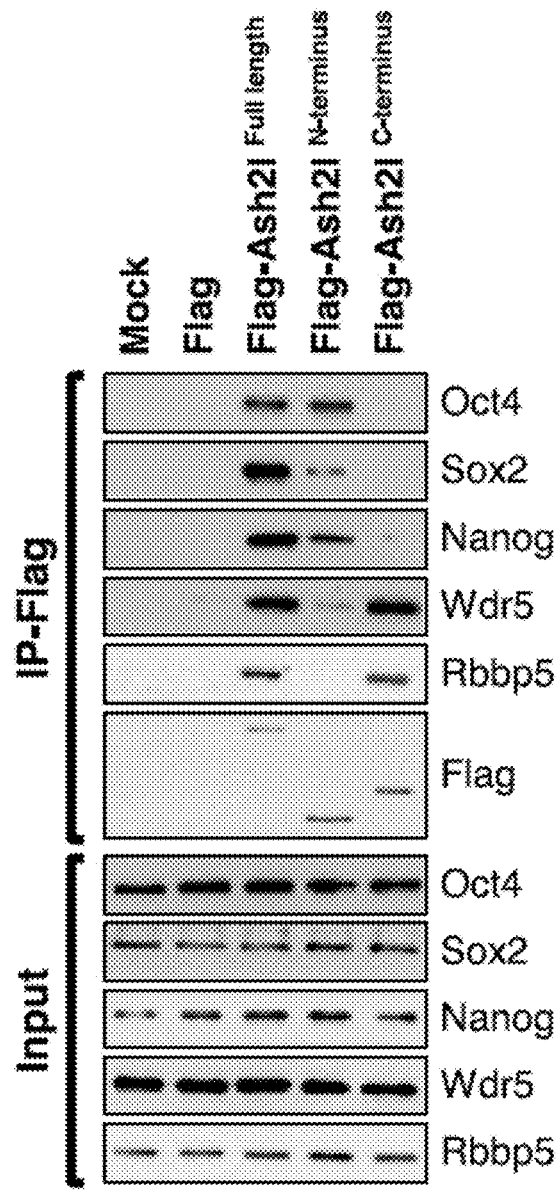
Figure 2F:
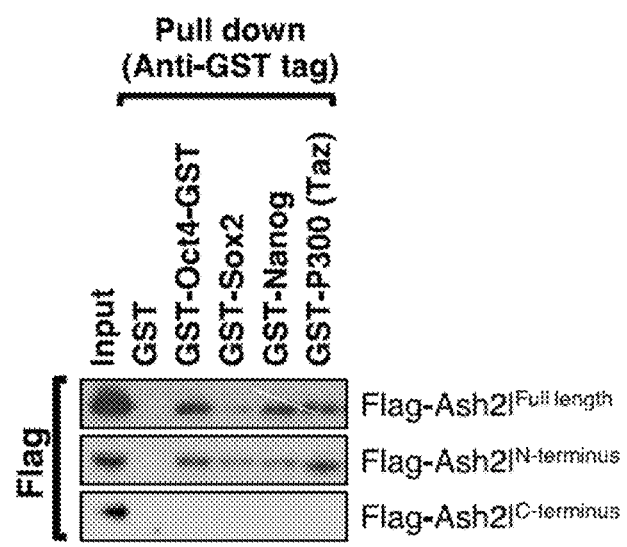
Figure 2G:
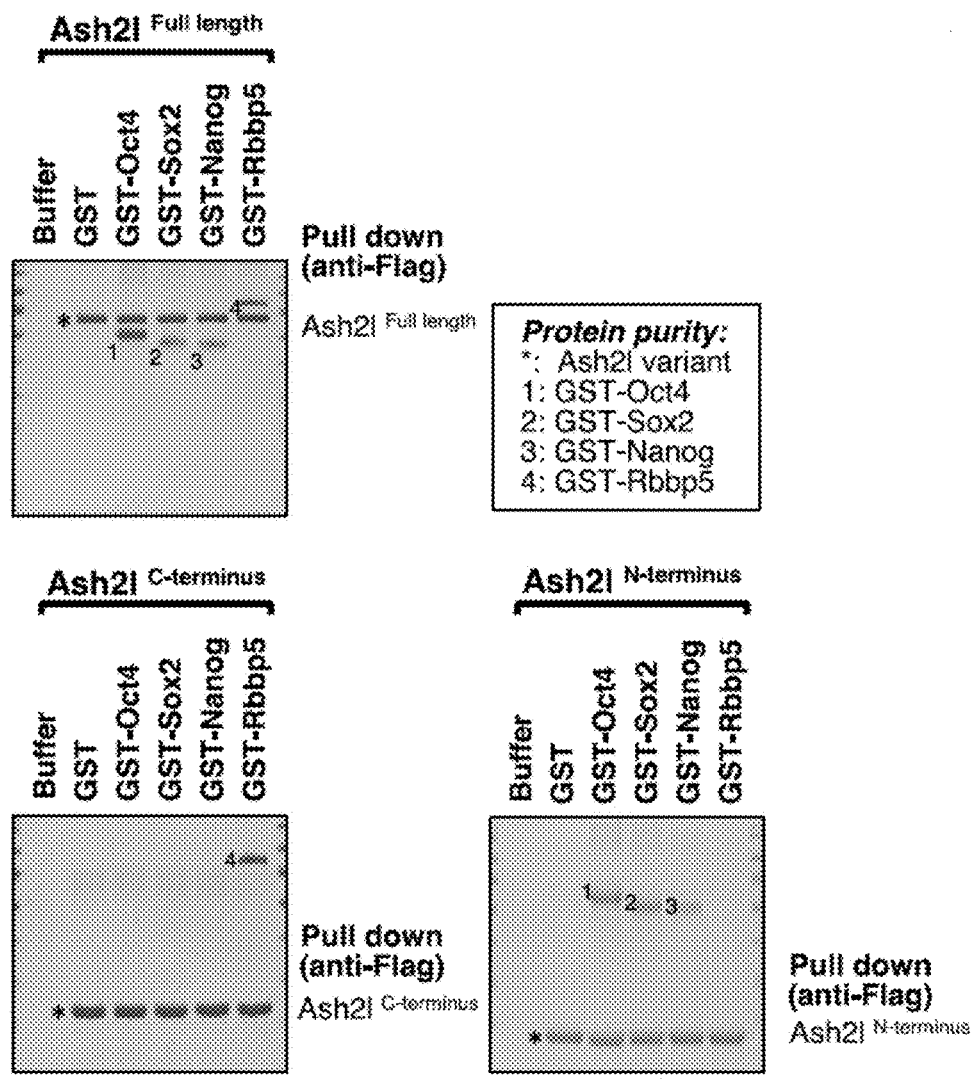
Figure 2H:
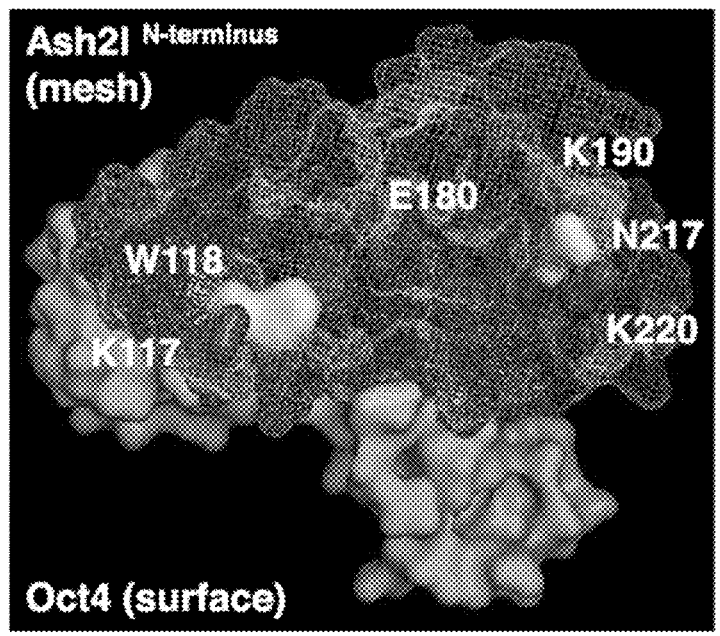
Figure 9C:
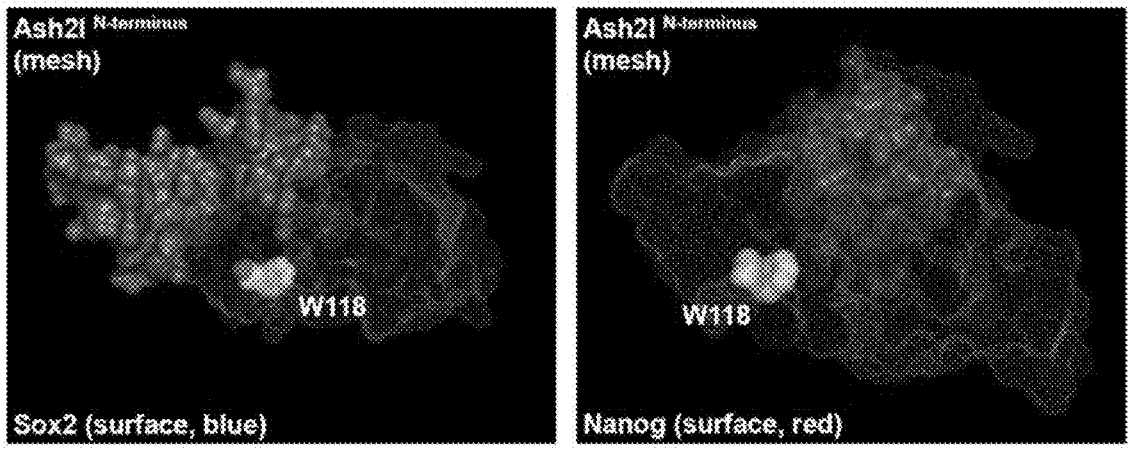

To identify the domain(s) of Ash2l-a responsible for this protein interaction, we constructed expression plasmids for Flag-tagged truncated Ash2l-a (Ash2l-N-terminus: 1-172, the PHD domain; and Ash2l-C-terminus: 387-623, the SPRY domain) and full-length Ash2l-a (Ash2l-full length: 1-623; FIG. 2D) for various experiments. First, we overexpressed truncated and full-length Ash2l-a proteins in HEK293T cells, and subjected the nuclear extracts to immunoprecipitation (FIG. 2E). Rbbp5 associated with full-length Ash2l-a and Ash2l-C, which is consistent with previous findings (26). Remarkably, Oct4, Sox2, and Nanog associated with full-length Ash2l-a and Ash2l-N terminus, but not Ash2l-C terminus (FIG. 2E). To further assess the direct protein-protein interaction, Ash2l-N, Ash2l-C, and full-length Ash2l-a recombinant proteins were purified from bacteria (FIG. 2G) and independently incubated with various recombinant proteins, including Oct4, Sox2 and Nanog, and the p300 (Taz domain) protein. As shown in the in vitro pull-down assays with further analysis using Western blot or Coomassie staining (FIGS. 2F and 2G), Ash2l-a directly interacted with the master stemness factors, Oct4, Sox2, and Nanog through its N terminus (1-172) (FIGS. 2F and 2G). We then used the ZDOCK software to simulate the molecular docking between Ash2l-a and Oct4 and further predicted that several residues at the N terminus of Ash2l-a, including K117, W118, E180, K190, N217, and K220, may be crucial for the recognition and interaction with Oct4 (FIG. 2H). To determine which residue(s) of Ash2l-a was important for its interaction with Oct4, we used immunoprecipitation to assess the binding abilities of different Flag-tagged Ash2l-a mutants (K117A, W118A, E180A, K190A, N217A, and K220A) to Myc-tagged Oct4. We found that among all Ash2l-a mutations, W118A point mutation significantly reduced by 79.2% of Ash2l-a interaction with Oct4 (FIG. 2I), indicating that the W118 residue of Ash2l-a was crucial for the Ash2l-a/Oct4 interaction. We further examined whether W118 residue of Ash2l-a is also crucial for Ash2l-a/Sox2 and Ash2l-a/Nanog interaction. Molecular docking simulation indicated that W118 residue was not predicted as candidate binding sites of Sox2 and Nanog (FIG. 9C). In vitro pull-down assay further confirmed that W118 mutation only interfered with Ash2l-a binding with Oct4 but not with Sox2, Nanog, Rbbp5, and Wdr5 (updated FIG. 2J). The purity of all recombinant proteins used in these in vitro pull-down assays was shown in FIG. 9D. Together, these findings demonstrated that besides the well-known Wdr5-Ash2l-a-Rbbp5-Dpy30 (WARD) complex, Ash2l-a physically interacts with Oct4, Sox2, and Nanog to form a novel Wdr5-independent Ash2l-a-Oct4-Sox2-Nanog (Ash2l-a/OSN) complex, in which the W118 residue of Ash2l-a is critical for the Ash2l-a-Oct4 interaction.

Figure 3A:
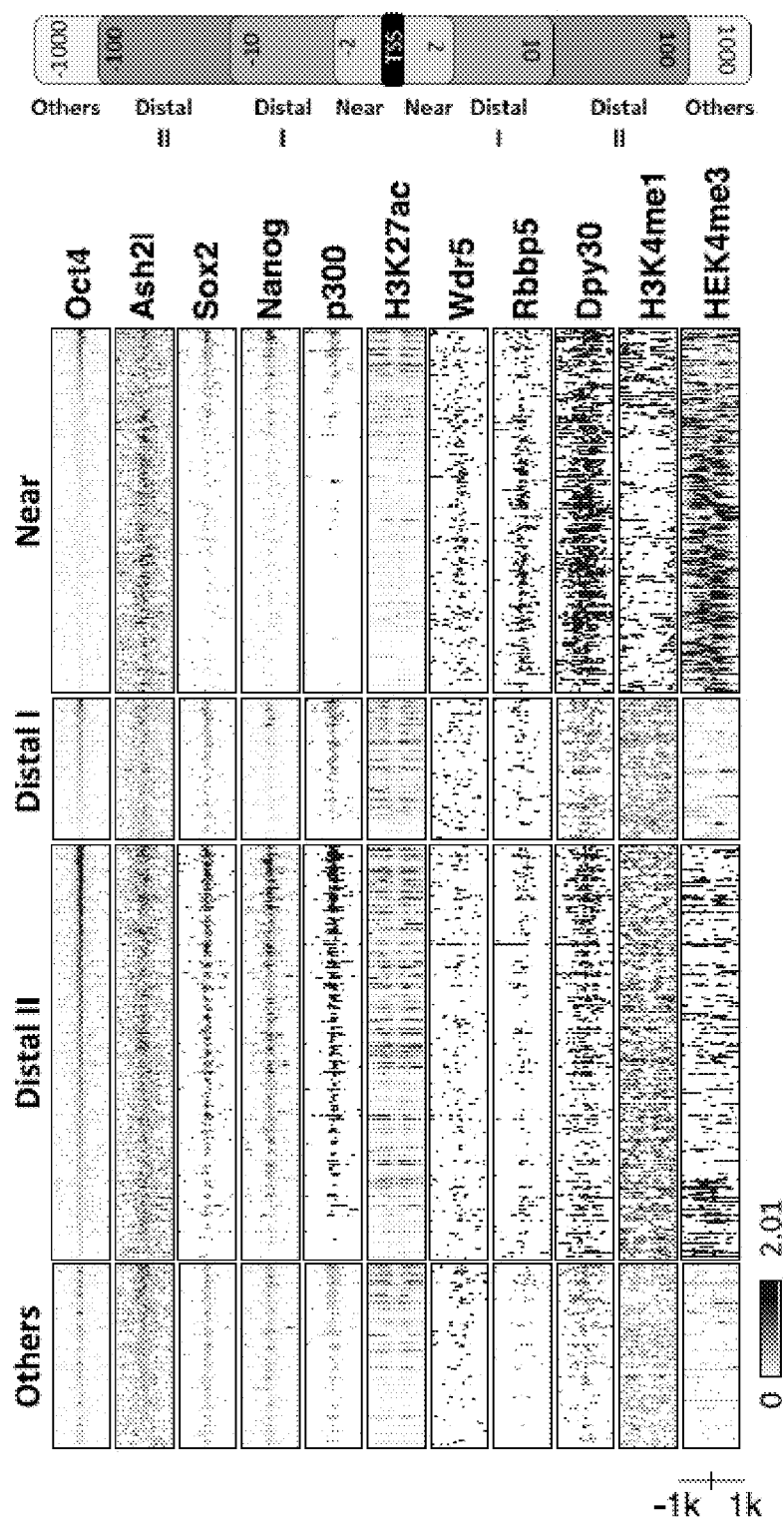
Figure 3B:
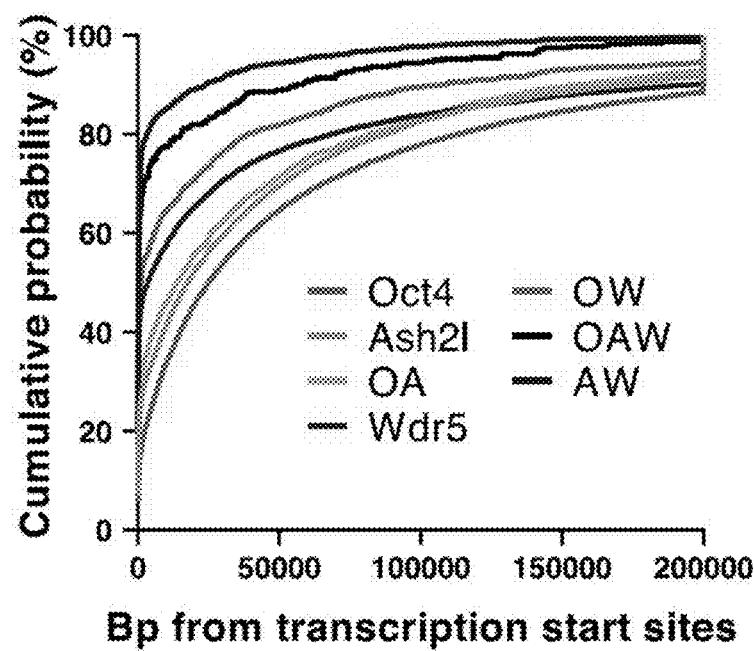
Figure 3C:
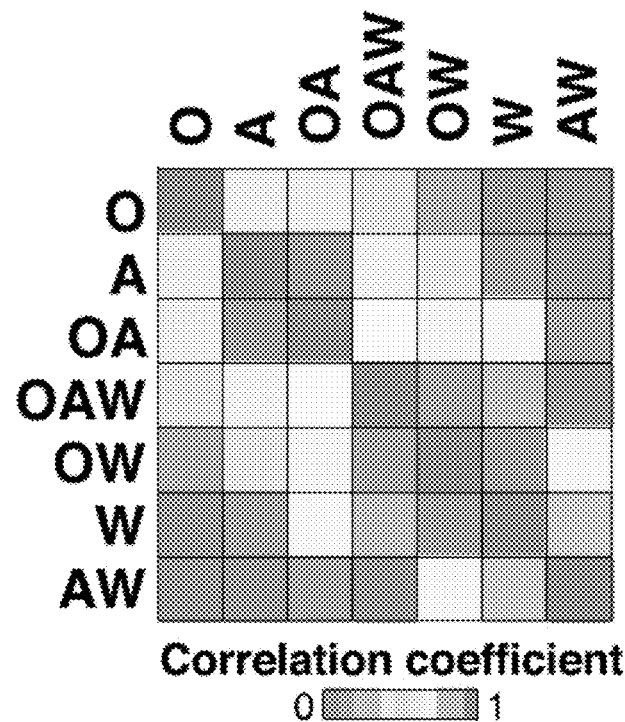
Figure 3D:
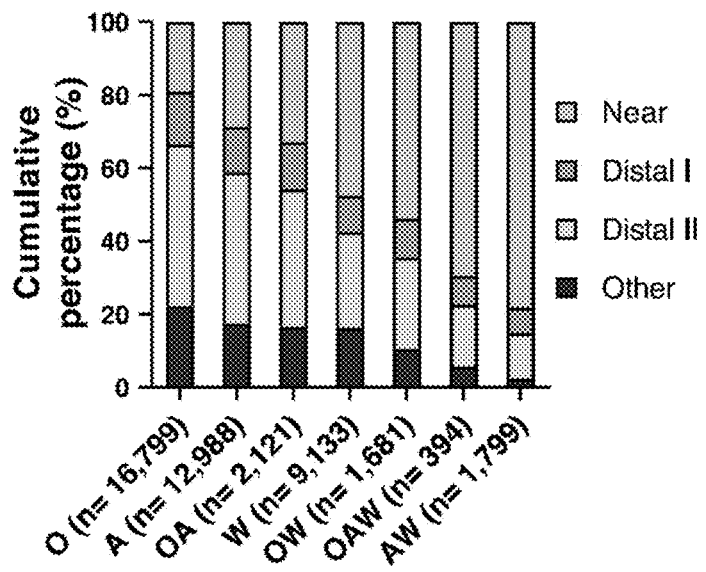
Figure 3E:
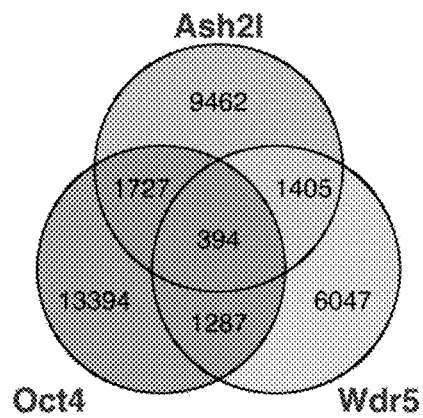
Figure 3E:
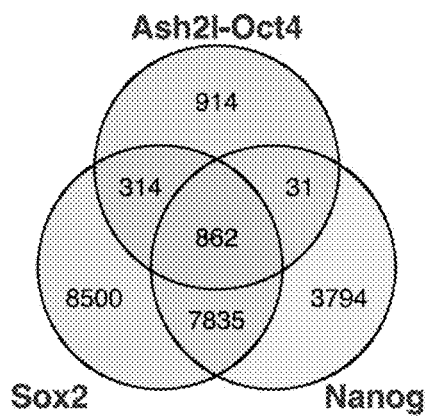

Co-Localization of Ash2l-a, Oct4, Sox2, and Nanog to Distal Cis-Elements in a Wdr5-Independent Manner Oct4 is the most pivotal transcription factor for the initiation of reprogramming and is crucial for the maintenance of pluripotency/self-renewal (27). Enhancers function as critical regulatory elements that integrate genomic information for cell fate transition (28). Oct4 can bind to enhancer elements and regulate distal genes (8-10). Following the identification of Ash2l-a/OSN complex, we investigated whether Ash2l-a could cooperate with Oct4 to regulate the distal elements of core pluripotent factors. We analyzed bioinformatics data on public domains to seek a potential interactive relationship between Ash2l-a and Oct4. We collected genome-wide chromatin immunoprecipitation (ChIP) binding profiles of OSN, Ash2l-a, and other members of the WARD complex (Wdr5, Rbbp5, and Dpy30) from previous reports (16,17) and from the ENCODE consortium to generate the sorted heatmap binding profile of OSN, Ash2l-a, and other members of the WARD complex (Wdr5, Rbbp5, and Dpy30), H3K27ac, H3K4me1, and H3K4me3 at different genomic regulatory elements (FIG. 3A). Using Oct4-Ash2l-a co-binding sites as the reference, we found that Oct4, Ash2l-a, Sox2, and Nanog were highly enriched at distal elements while Wdr5, Rbbp5, and Dpy30 were less enriched on Oct4-Ash2l-a co-binding gene loci (FIG. 3A). We further organized elements bound by Oct4-Ash2l-a (OA), Oct4-Wdr5 (OW), Ash2l-a-Wdr5 (AW) and Oct4-Ash2l-a-Wdr5 (OAW), and generated the cumulative probability of the distance to the closest TSS (FIG. 3B), the similarity matrix (FIG. 3C), the stacked bar plot (FIG. 3D) and the Venn diagram (FIG. 3E). The cumulative probability of the distance to the closest TSS revealed that elements bound by OA predominantly localized far from the TSS, while the W, OW, AW, and OAW bound elements were relatively close to the TSS (FIG. 3B). Similarity matrix showed that the binding patterns of A and OA categories were similar while the patterns of W-bound elements (W, OAW, and OW) were also relatively comparable but distinct from those of A and OA categories (FIG. 3C). The stacked bar plot showed that Oct4, Ash2l-a, and OA binding predominantly occurred at distal elements (i.e. Distal I and Distal II) rather than the TSS; while Wdr5-bound elements (i.e. W, OW, OAW, and AW) were generally localized at Near elements near the TSSs (FIG. 3D and FIG. 10). The corresponding numbers of binding/co-binding loci for the given genes are shown in a Venn diagram (FIG. 3E). Among the total 2,121 of OA co-binding loci, 862 gene loci were Ash2l-a/OSN co-binding loci (FIG. 3E). A Venn pie chart further showed that the binding of Oct4 or Ash2l-a predominantly localized at Distal II elements, and that their most comment binding pattern at Distal II elements was OA co-binding (FIG. 10, left and middle); by contrast, Wdr5 mainly localized at Near elements (FIG. 10, right). Taken together, these results showed that loci bound by Ash2l-a without the involvement of Wdr5 (i.e., OA and A) had high tendency to be located at distal regions, while Wdr5-bound loci (OW, AW, OAW) were TSS-adjacent.

Figure 3F:
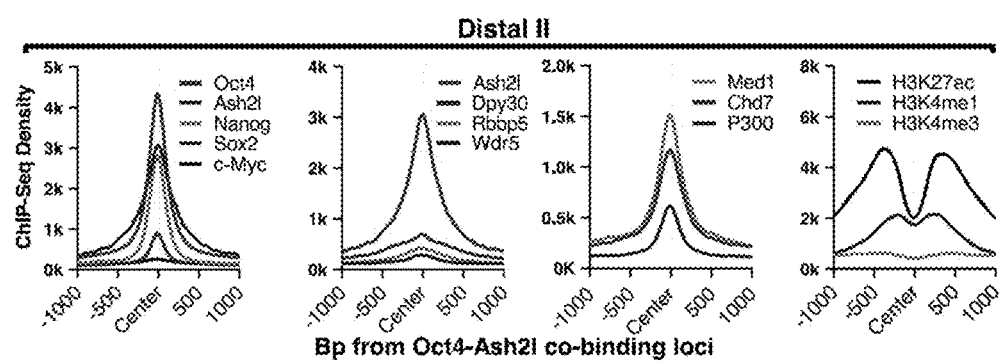
Figure 3G:
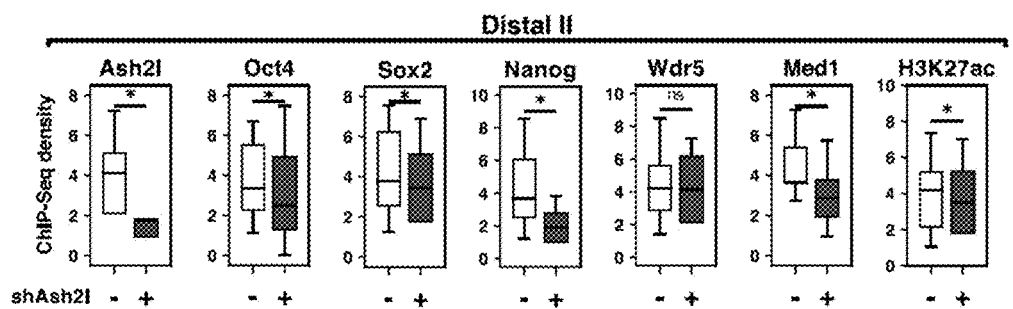

We further analyzed the binding proteins on the Oct4-Ash2l-a (OA) co-binding gene loci with a focus on master pluripotent genes, WARD components, enhancer-binding proteins, and histone marks (FIG. 3F). The aggregation profiles showed that, at Distal II elements, the OA co-binding gene loci were enriched for Oct4, Sox2, and Nanog (FIG. 3F, first panel from left), as well as several well-known enhancer-binding proteins, including Med1, p300, and Chd7 (FIG. 3F, second panel from right). For the components of WARD complex, only Ash2l-a but not Wdr5, Rbbp5 and Dpy30 was enriched in Distal II elements (FIG. 3F, second panel from left). Notably, a prominently strong H3K27ac mark and moderate H3K4me1were detected at the Distal II elements, whereas H3K4me3 marks were not detected (FIG. 3F, first panel from right), indicating an active and poised chromatin environment around the OA-co-binding gene loci at distal elements. Next, we performed ChIP-seq analysis to evaluate the binding of Oct4, Sox2, Nanog, Wdr5, Med1, and H3K27ac in both control and Ash2l-a knockdown ESCs. At Distal II elements, Ash2l-a knockdown reduced the enrichment of Oct4, Sox2, Nanog, Med1, and H3K27ac, whereas the enrichment of Wdr5 was not affected (FIG. 3G). The colocalization of Ash2l-a, Oct4, Sox2, and Nanog at Distal II elements was Wdr5-independent, distinct from the WARD complex prone to be near the TSS.

Figure 4A:
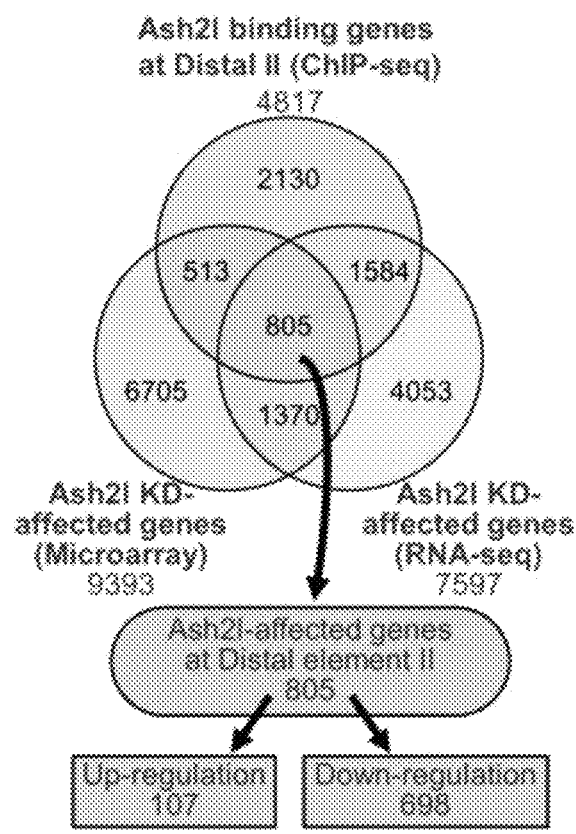
Figure 4B:
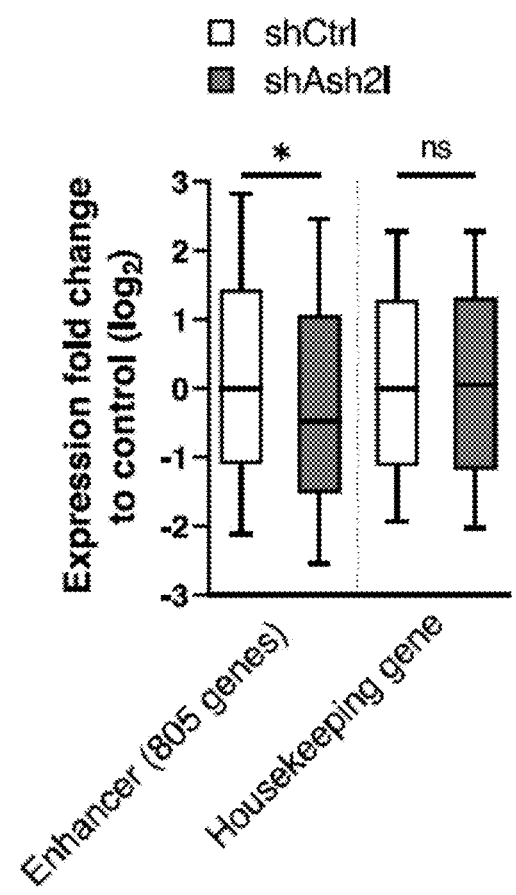
Figure 4C:
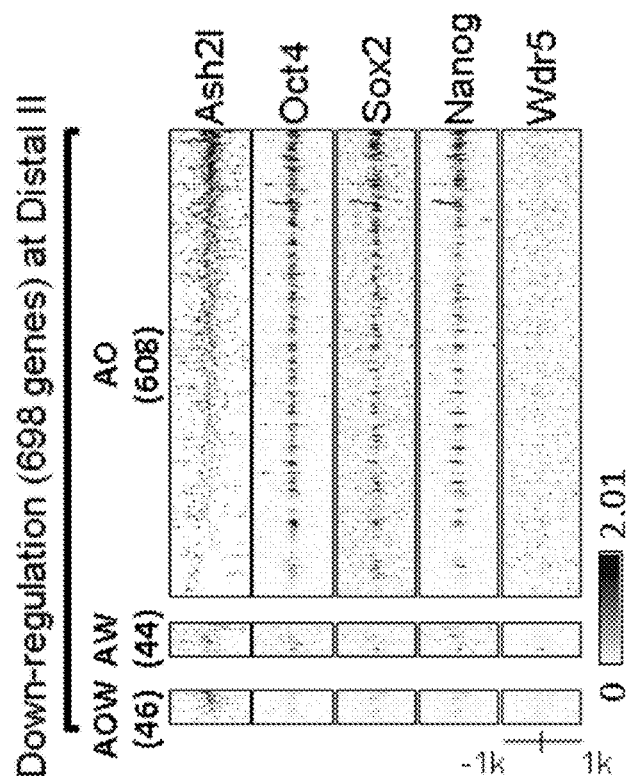
Figure 4D:
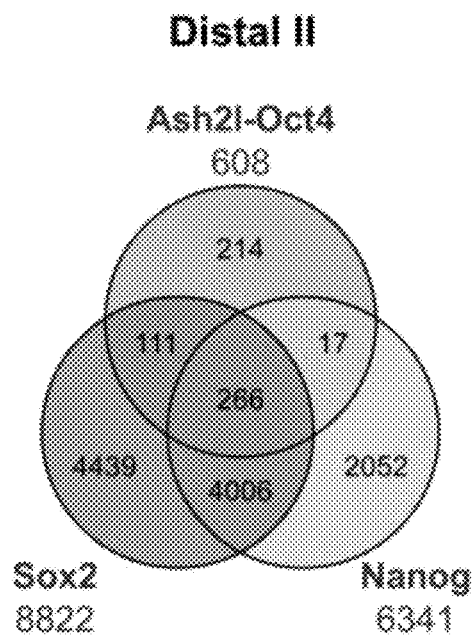
Figure 11A:
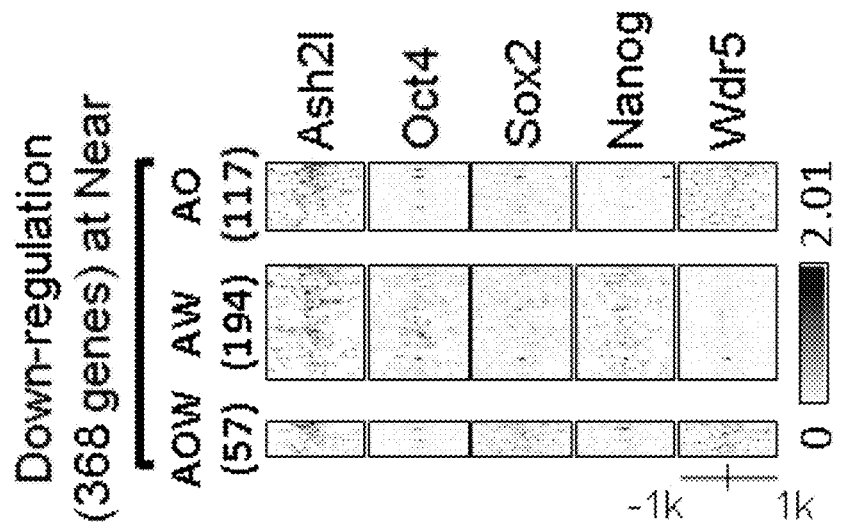
Figure 11B:
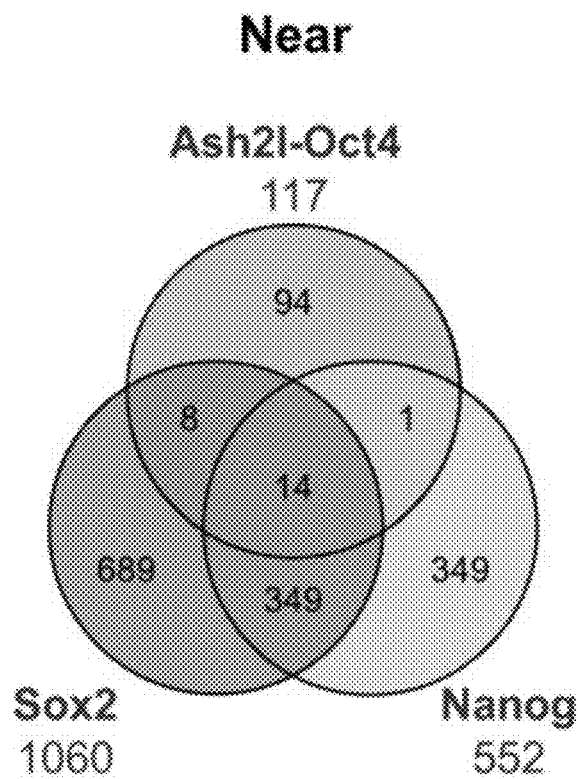

Ash2l-a/OSN Complex Locates on the Super-Enhancers to Regulate Enhancer Activation Super-enhancer activity was reported to control pluripotency and reprogramming, as well as to regulate genes critical for cell identity (10,29). Given that our genome-wide analysis showed the colocalization of Ash2l-a and OSN at Distal II elements, we hypothesized that Ash2l-a might cooperate with the master transcription factors at Distal II elements to regulate genes involving in pluripotency and cell fate determination. To verify this hypothesis, we first overlapped ChIP-seq data of Ash2l-a-binding genes with microarray data and RNA-seq data from Ash2l-a knockdown cells to identify the downstream genes that were bound by Ash2l-a at Distal II elements with expression affected by Ash2l-a (FIG. 4A). Overall, the expression of a total of 805 super-enhancer-driven genes was affected by Ash2l-a depletion (FIGS. 4A and 4B). Among these 805 genes, we found 698 Ash2l-a-targeting gene loci down-regulated upon Ash2l-a knockdown at Distal II elements (FIG. 4A). We then categorized these 698 gene loci into binding targets of Ash2l-a-Oct4 (AO), Ash2l-a-Wdr5 (AW) and Ash2l-a-Oct4-Wdr5 (AOW) and found 608 AO-targeted gene loci at Distal II elements (FIG. 4C; See also Table 1). Among the total 608 AO-targeted gene loci, 266 gene loci were co-bound by Ash2l-a/OSN at Distal II elements (FIG. 4D). We also performed the same analysis and categorized the ChIP-seq data of Near elements into Ash2l-a-Oct4 (AO), Ash2l-a-Wdr5 (AW) and Ash2l-a-Oct4-Wdr5 (AOW) (FIG. 11A). The number of overlapping peaks are shown in FIG. 11A (left). Among the total 117 AO-targeted gene loci at Near elements, 14 gene loci were co-bound by Ash2l-a/OSN (FIG. 11B).

Figure 4E:
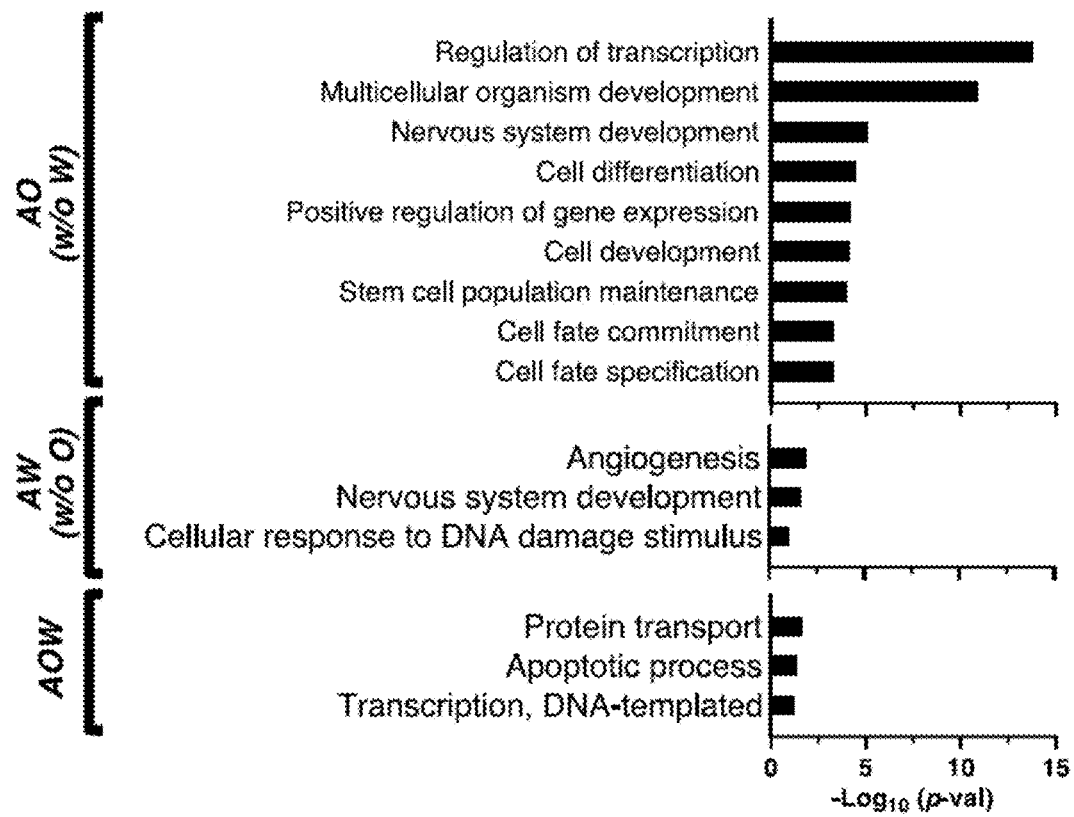
Figure 4F:
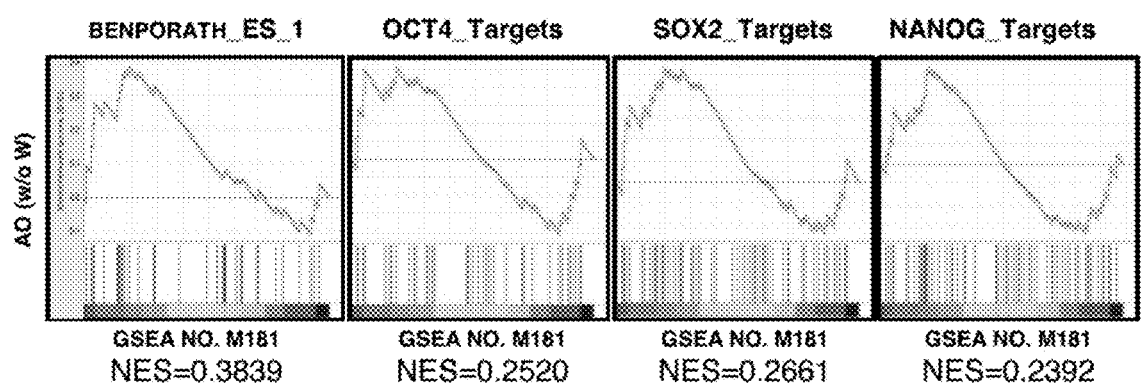
Figure 11C:
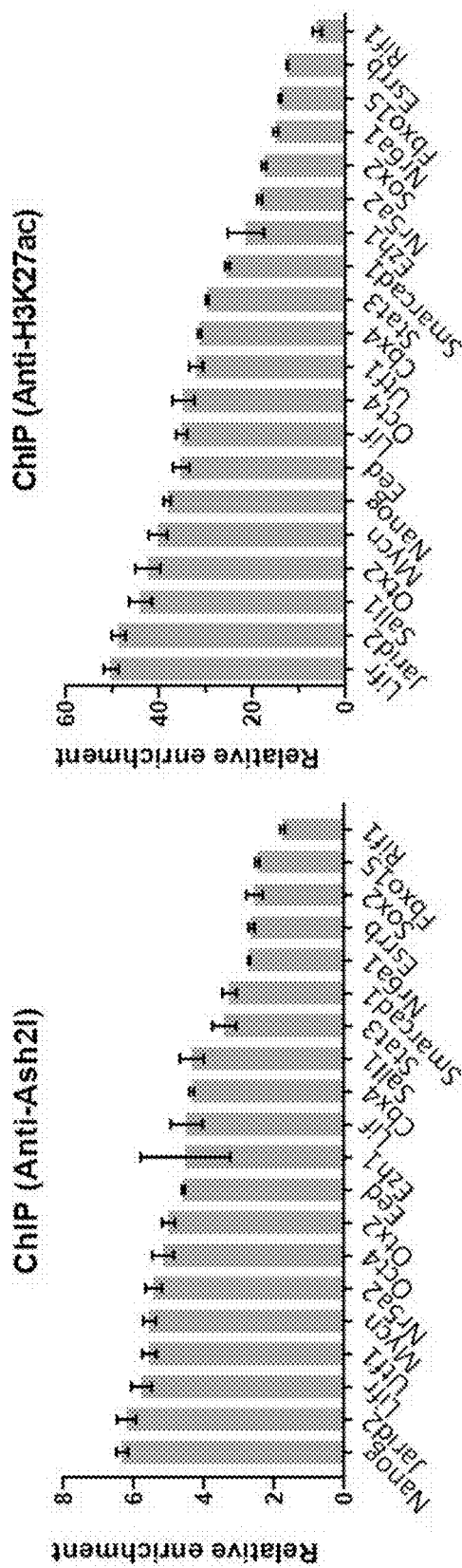
Figure 11D:
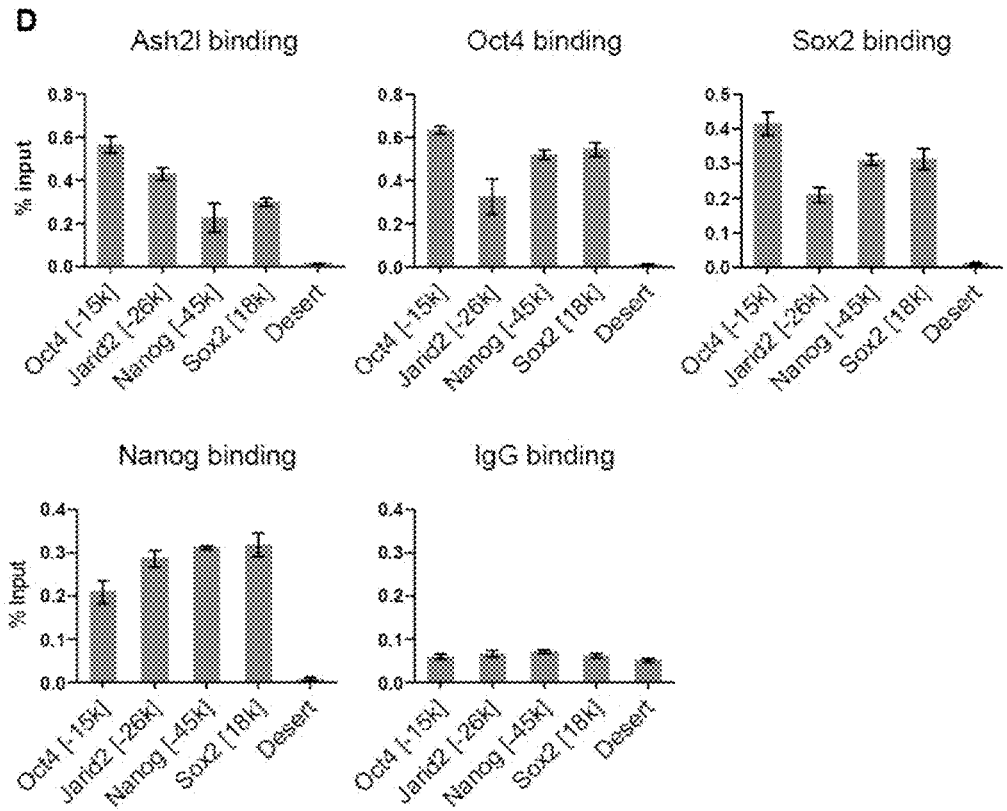

The Gene Ontology analysis revealed that these 608 AO-binding gene loci were responsible for genes important for regulation of transcription, multicellular organism development, and cell differentiation, etc., while AW- and AOW-binding loci carried relatively poor biological relevance (FIG. 4E). By gene set enrichment analysis (GSEA), we also observed that the genes enriched for AO binding at Distal II elements and downregulated by shAsh2l, are primarily those genes that are upregulated in ESCs and the downstream genes targeted by Oct4, Sox2, and Nanog (FIG. 4F). We performed ChIP followed by quantitative PCR (ChIP-qPCR) to evaluate the binding ability of Ash2l-a and the enrichment of H3K27ac, the histone mark that identifies active enhancer, at these Ash2l-a-regulated genes. We observed that the enhancers of Jarid2 and Nanog genes had strong enrichment for Ash2l-a and H3K27ac, while Oct4 and Sox2 genes were moderately bound by Ash2l-a and enriched for H3K27ac (FIG. 11C). Using ChIP-qPCR, we next showed that Ash2l-a, Oct4, Sox2, and Nanog were individually bound to the enhancers of Oct4, Jarid2, Nanog, and Sox2 (FIG. 11D).

Figure 4G:
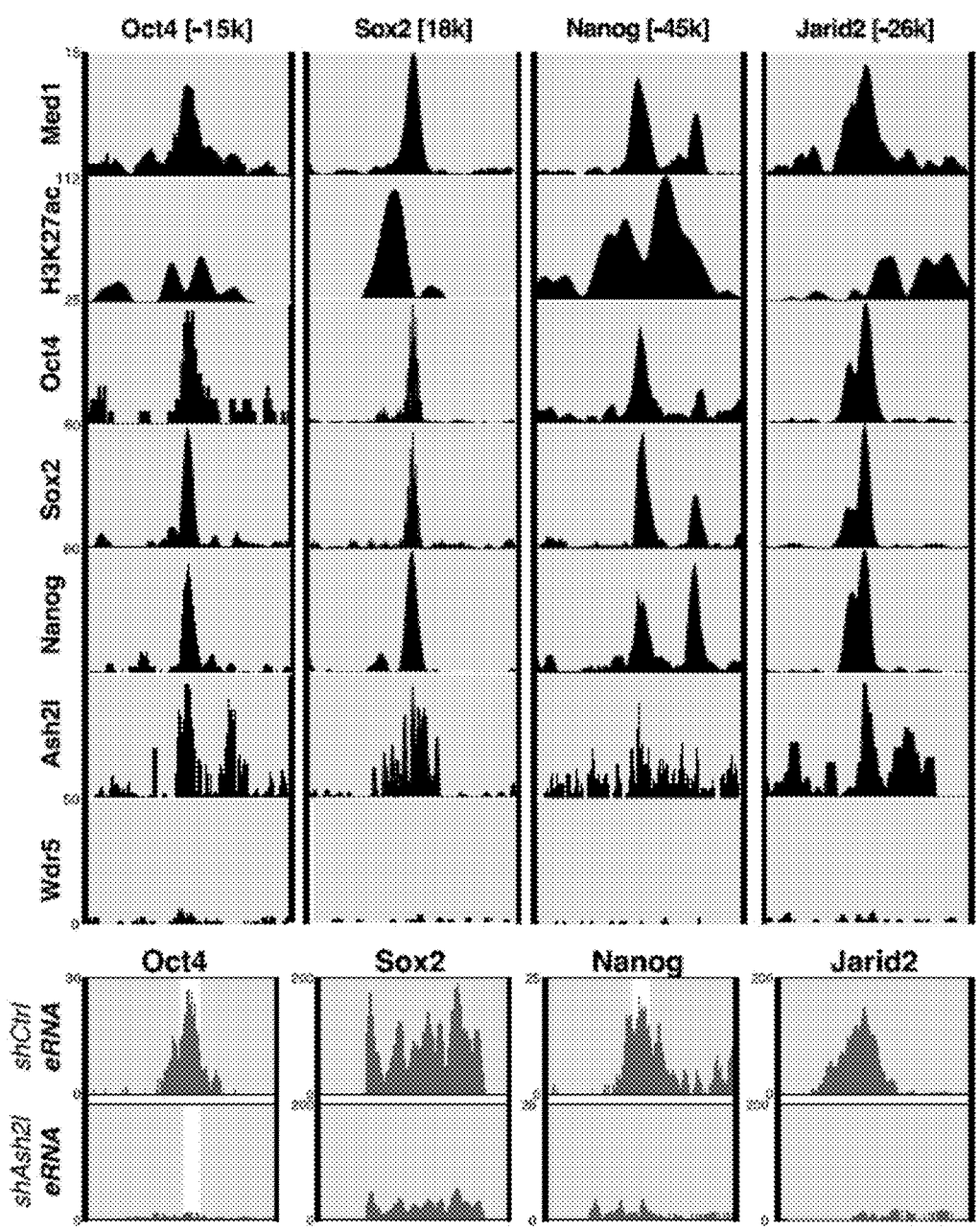
Figure 4H:
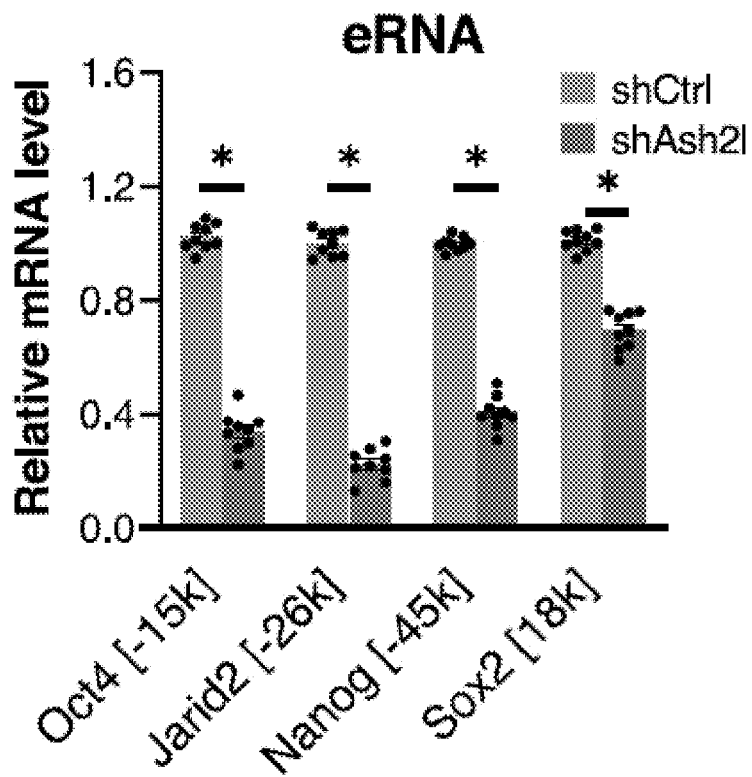
Figure 4I:
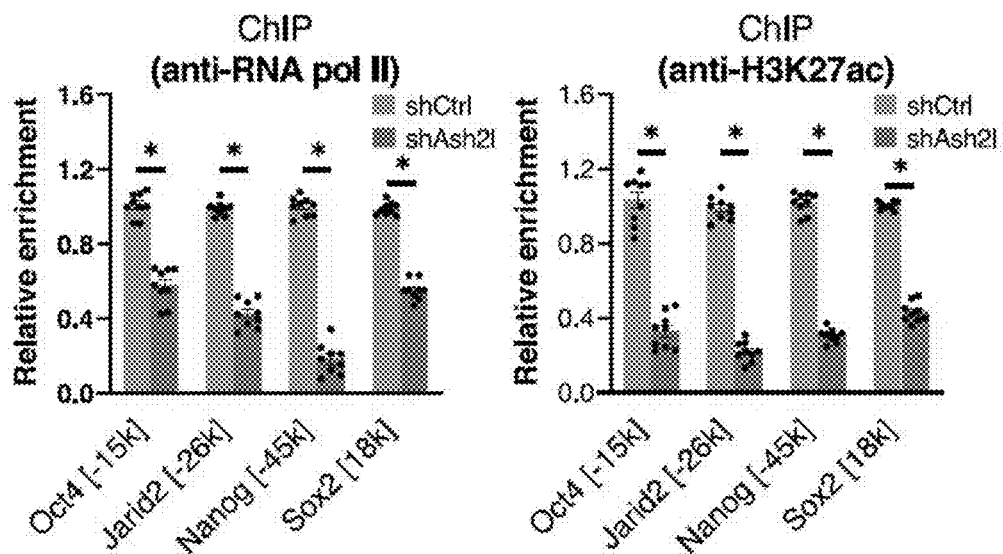
Figure 4J:
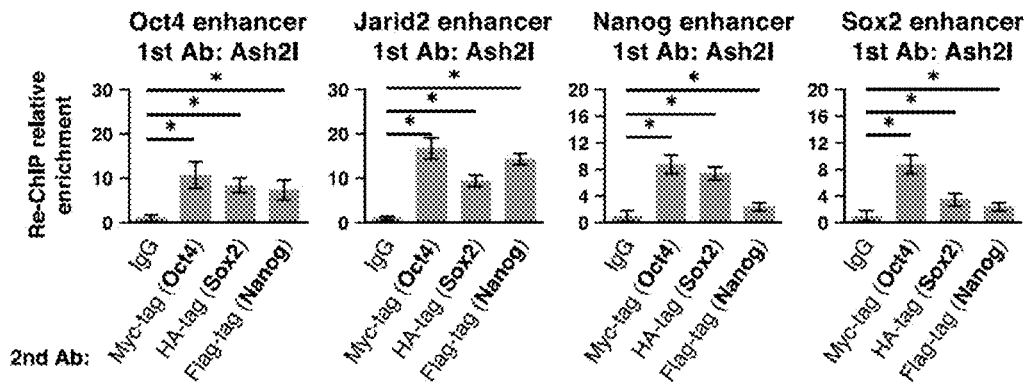
Figure 4K:
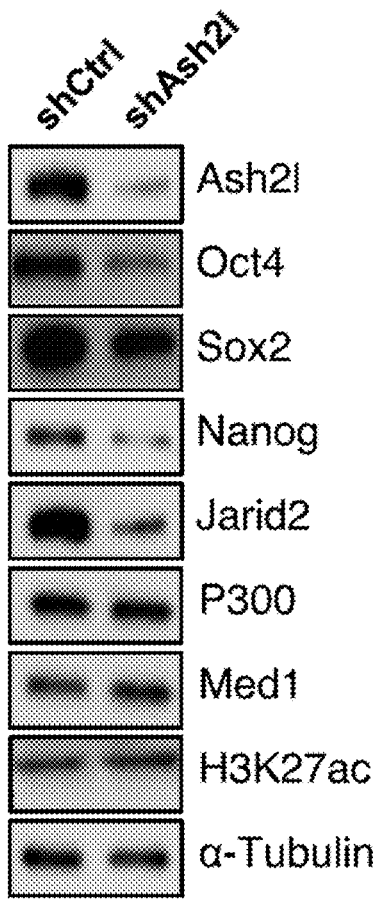
Figure 11E:
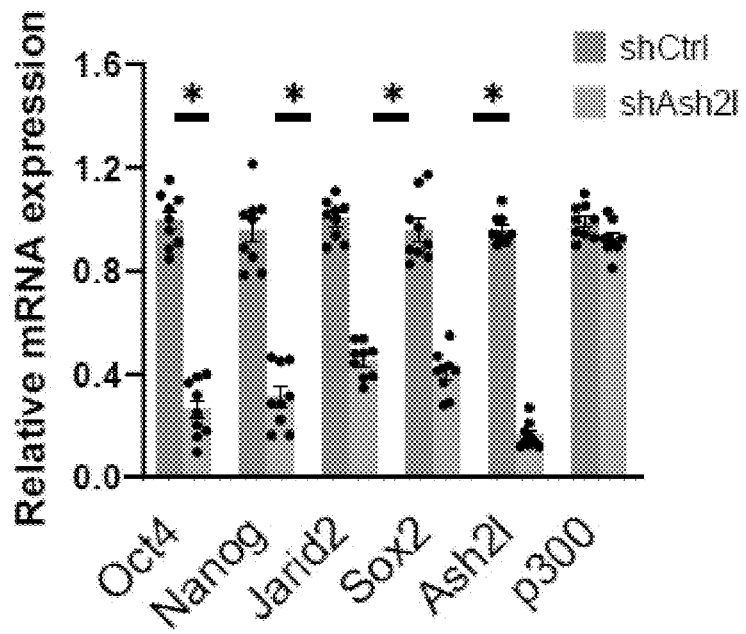

Subsequently, we used ChIP-seq and RNA-seq to examine whether these four Ash2l-a-bound enhancers (i.e. Jarid2, Oct4, Sox2, and Nanog enhancers) carry enhancer-specific characteristics. First, we added the genome browser tracks to show the ChIP-seq results of Med1, H3K27ac, Oct4, Sox2, Nanog, Ash2l-a, and Wdr5 from the existing ChIP-seq database (FIG. 4G, upper). In the ChIP-seq results, Ash2l-a, Oct4, Sox2, and Nanog, but not Wdr5, did bind to aforementioned enhancer regions that are enriched for enhancer marks H3K27ac and co-activator Med1 (FIG. 4G, upper). RNA-seq also detected that the regions producing enhancer RNA (eRNA) colocalized with these Ash2l-a-bound enhancers (FIG. 4G, lower). Notably, as examined by qPCR and ChIP-qPCR, Ash2l-a knockdown reduced eRNA production, RNA polymerase II, and H3K27ac histone mark enrichment, indicating that Ash2l-a drove the activation of these enhancers (FIGS. 4H and 4I). Super-enhancers are transcriptional regulatory regions distant from TSS, known to be enriched for OSN and to recruit various enhancer-binding proteins to catalyze H3K27 acetylation (8-10). Based on the enhancer features of these Ash2l-a-bound regions and the binding of Oct4, Sox2, and Nanog at distal elements distant from the TSS (>10 k), our findings indicated that these Ash2l-a-bound regions on Oct4, Jarid2, Nanog, and Sox2 genes are super-enhancers. To validate the existence of Ash2l-a/OSN complex at the super-enhancers of Jarid2, Oct4, Sox2, and Nanog, we further used Re-ChIP assay to examine the co-binding of Ash2l-a and Oct4, Sox2, and Nanog at these sites. Ash2l-a did form the aforementioned Ash2l-a/OSN complex at these super-enhancers (FIG. 4J). Furthermore, we analyzed the effects of Ash2l-a knockdown on the expression of stemness-associated genes in ESCs and showed that Ash2l-a depletion led to the decrease in mRNA and protein levels of Jarid2, Oct4, Sox2, and Nanog (FIG. 11E and FIG. 4K). Ash2l-a knockdown did not affect p300 mRNA expression (FIG. 11E) and the protein amount of p300, Med1, and H3K27ac (FIG. 4K). These data revealed an Ash2l-a-mediated regulation on the protein expression levels of Jarid2, Oct4, Sox2, and Nanog. Ash2l-a bound to the super-enhancers at the distal elements of stemness-associated genes to regulate genes expression through enhancer activation.

Disruption of Ash2l-a-Binding Motifs at Super-Enhancers Abrogated OSN Enrichment and Enhancer Activation.

Figure 12:
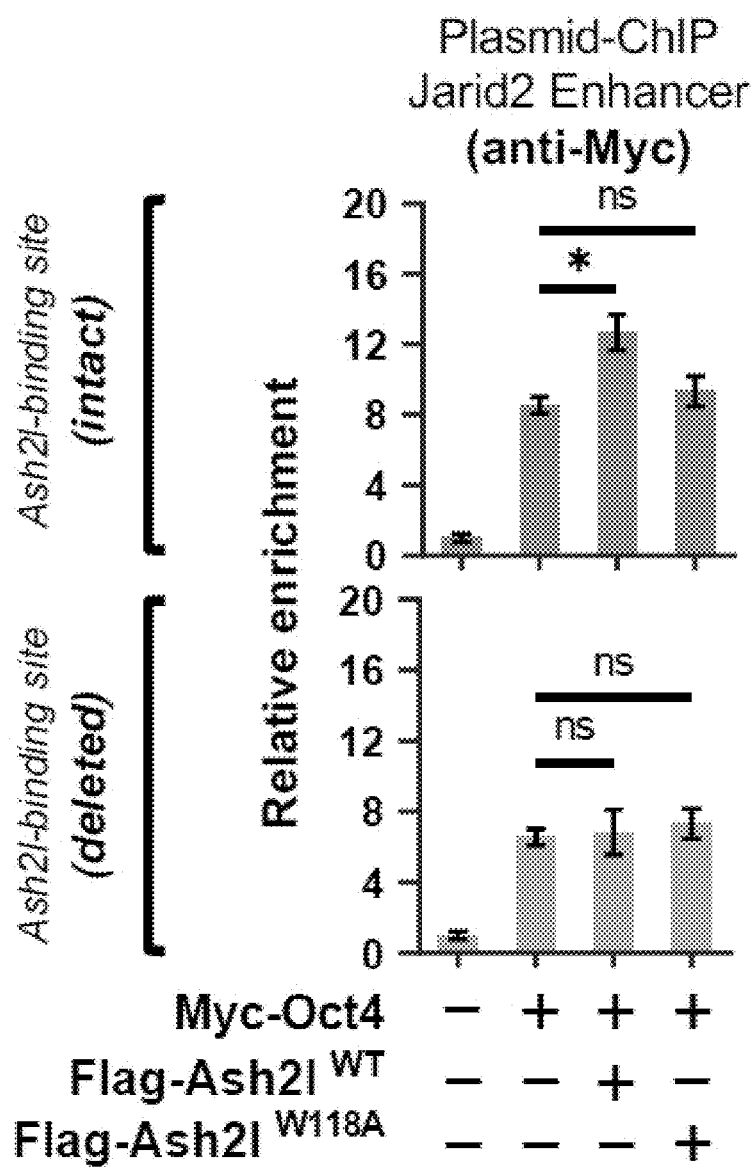
Figure 12D:
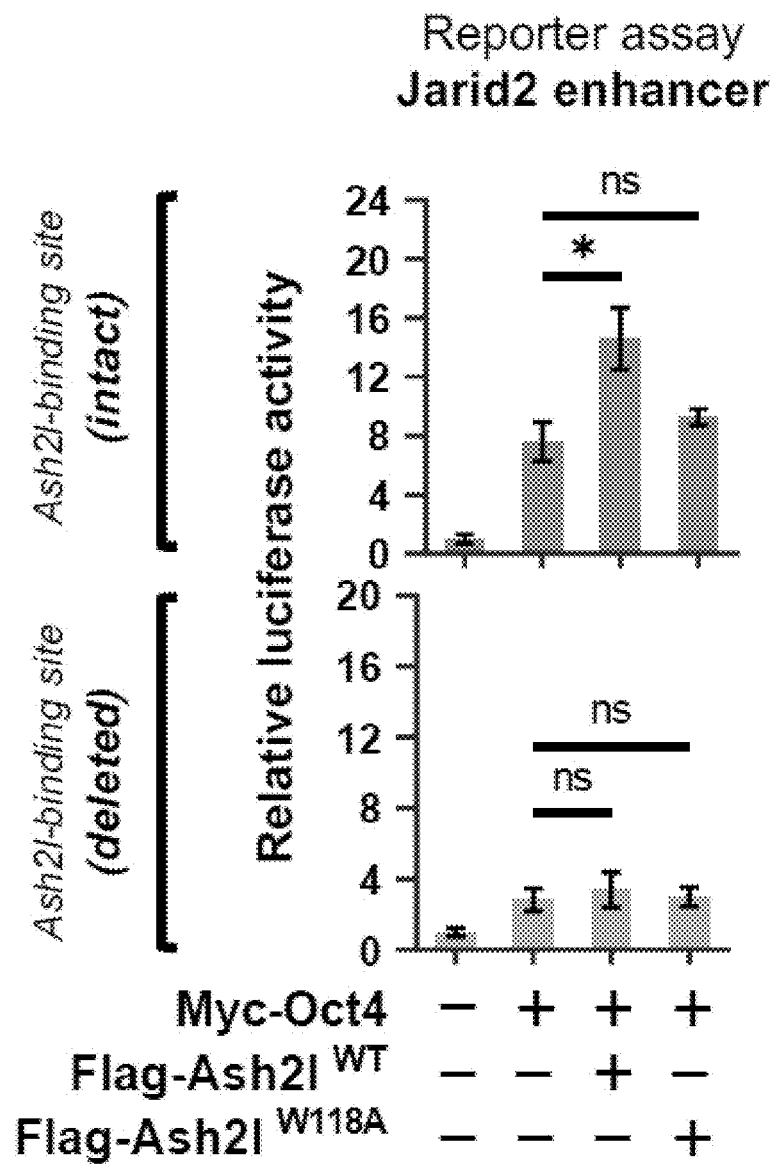
Figure 12E:
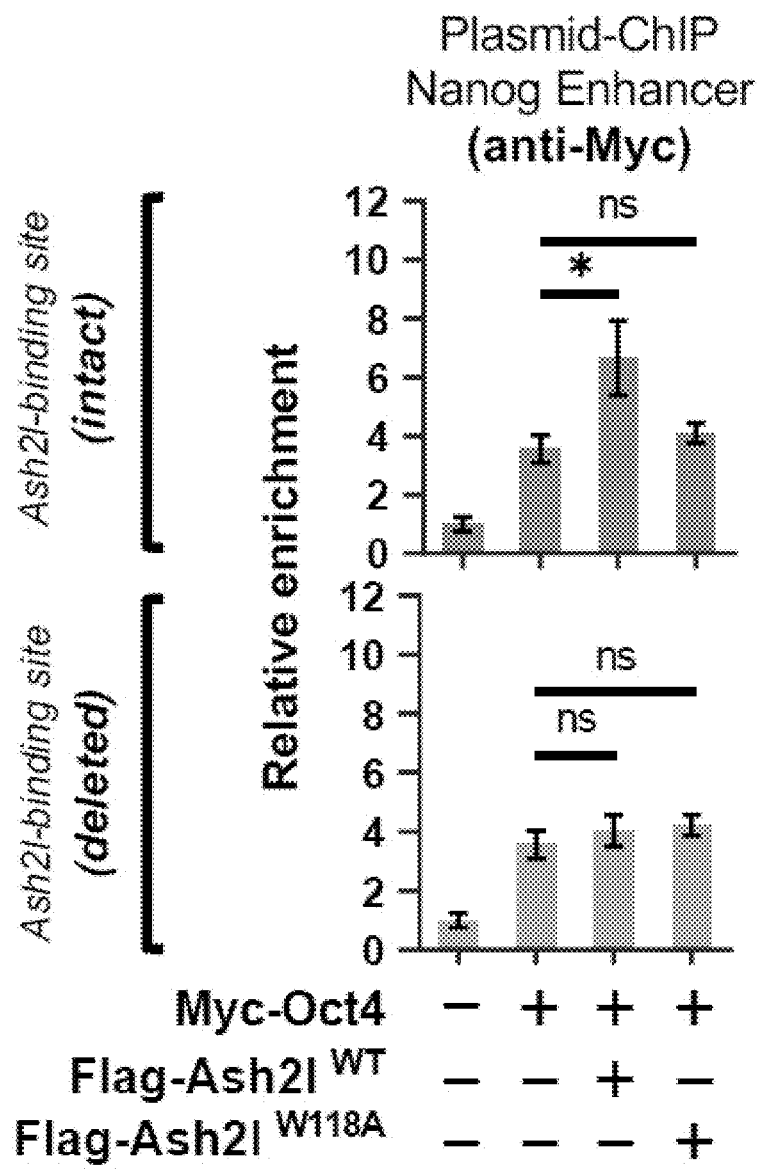
Figure 12:
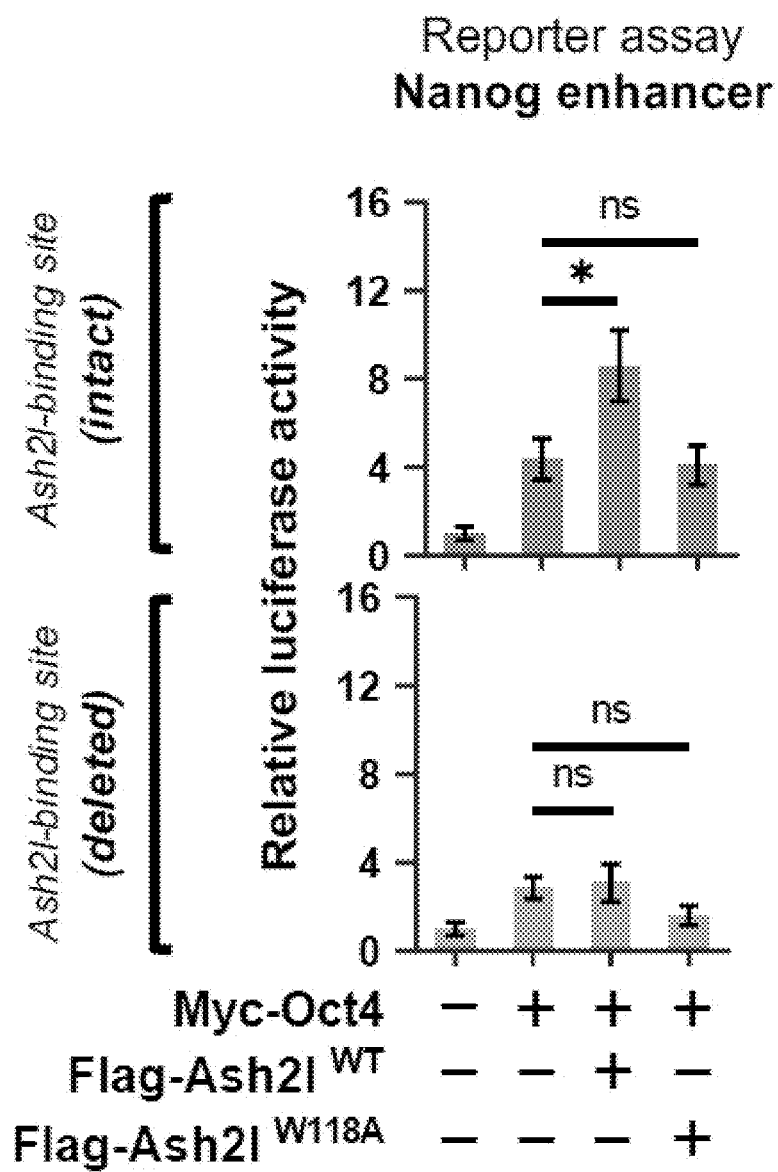
Figure 12G:
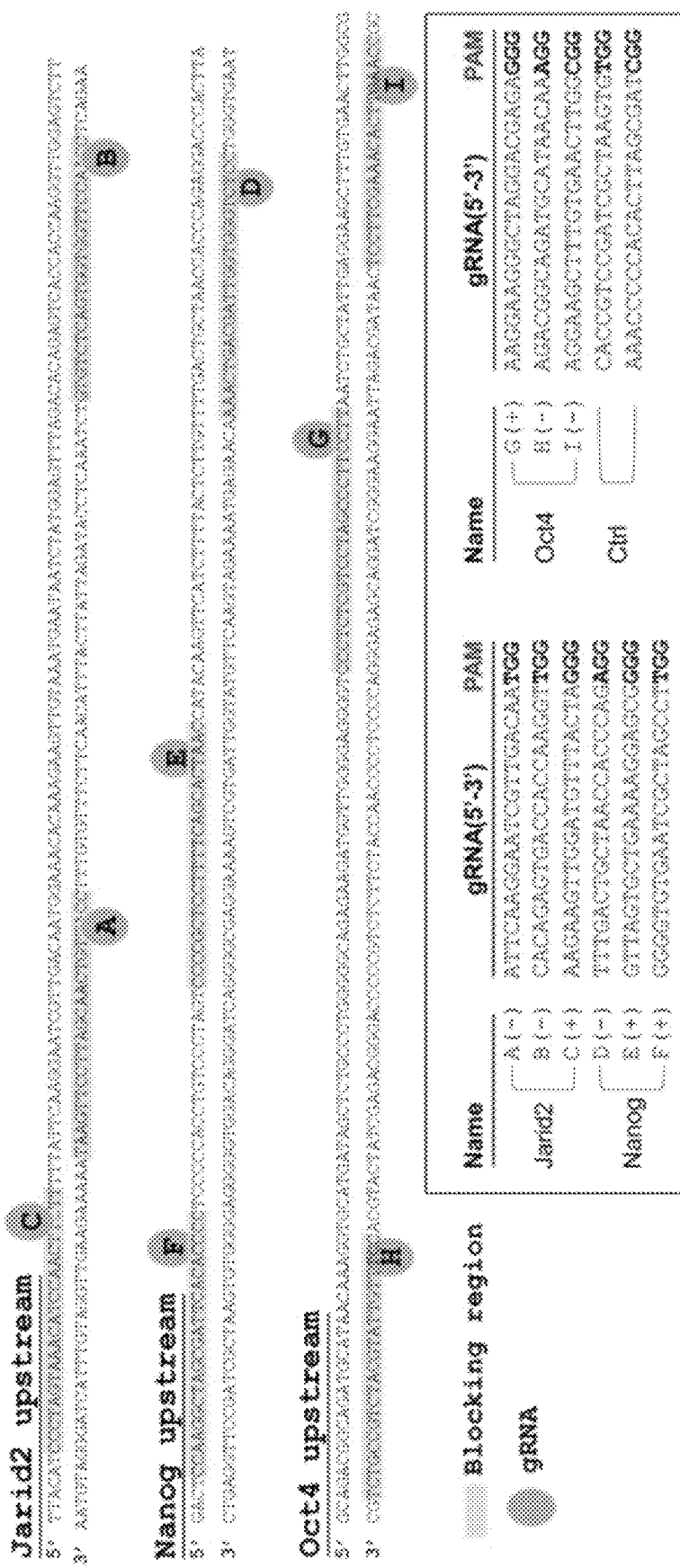
Figure 13:
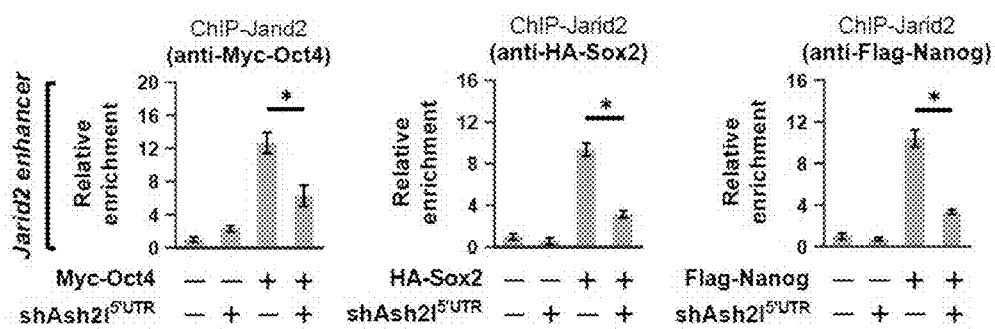
Figure 13B:
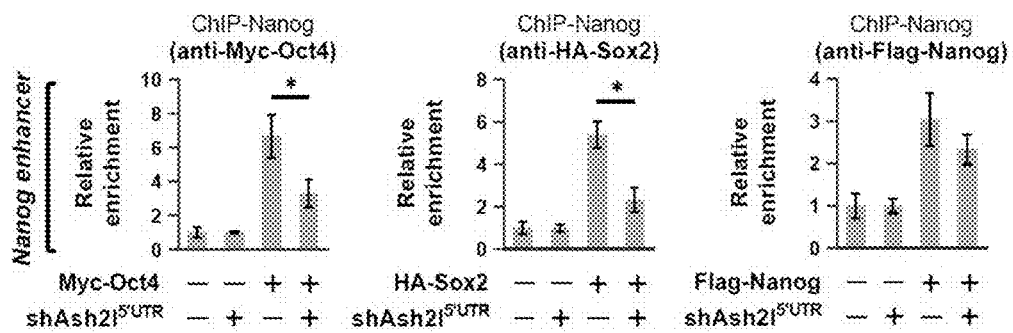
Figure 13C:
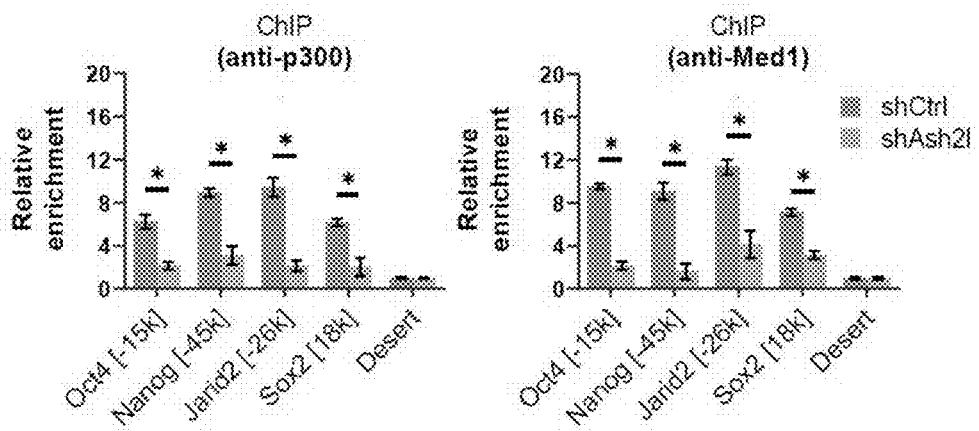
Figure 13D:
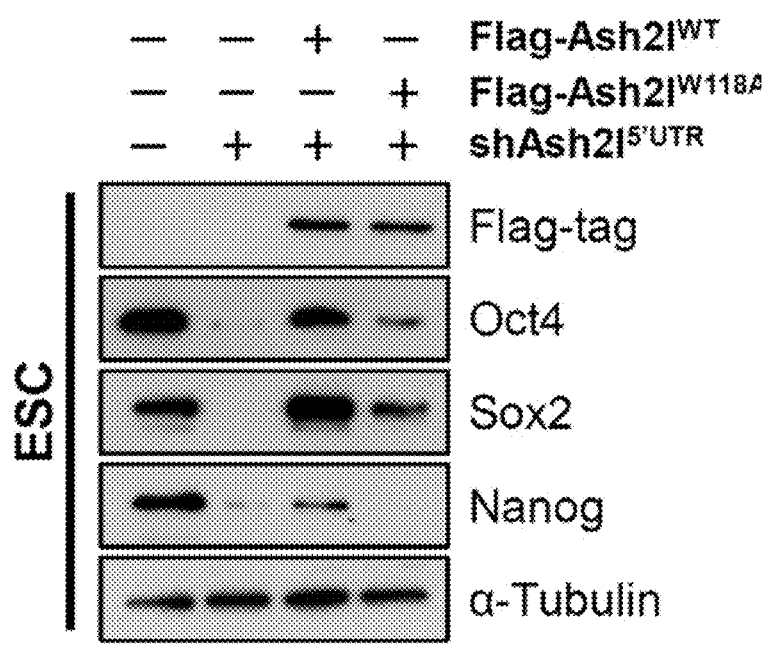
Figure 13E:
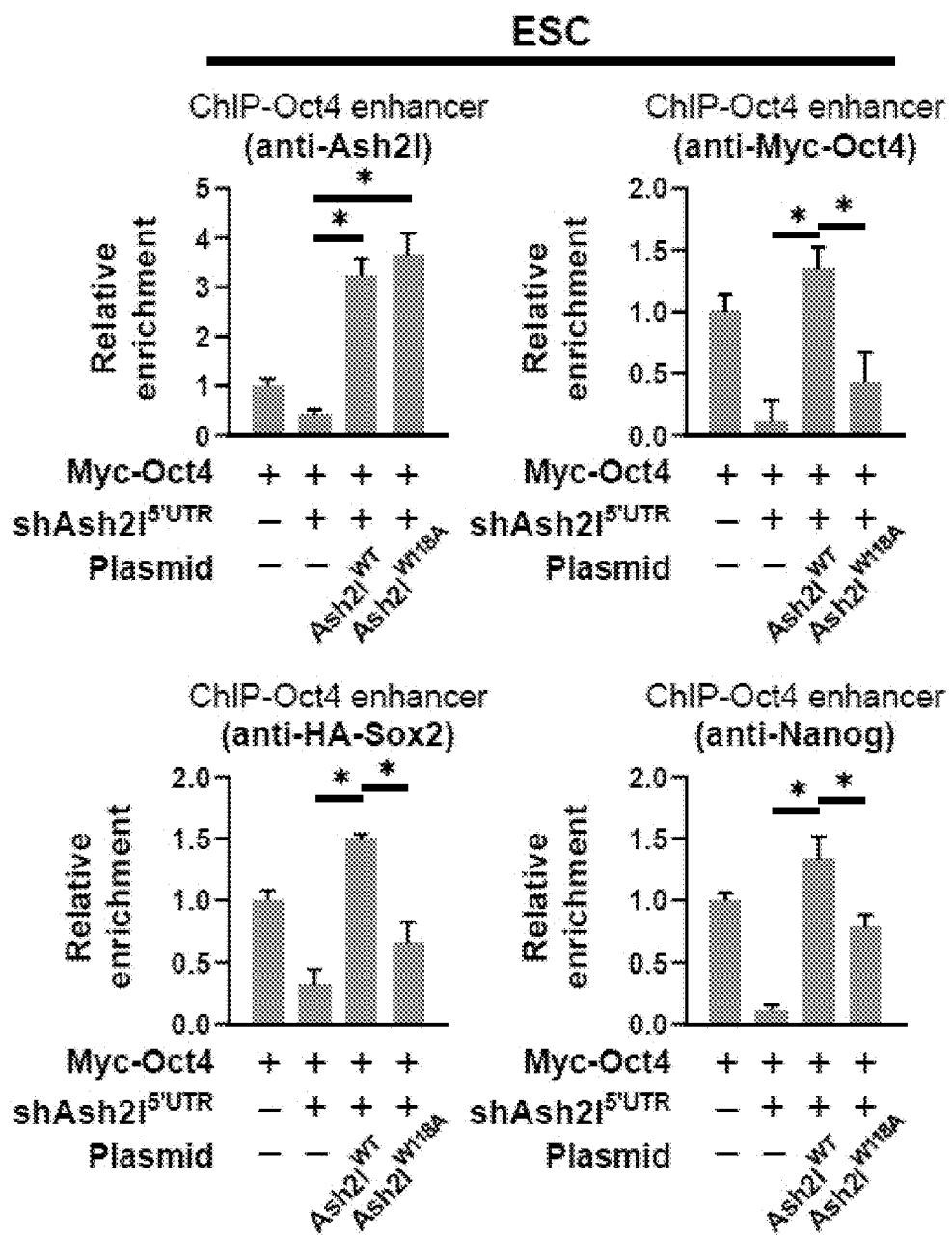
Figure 13F:
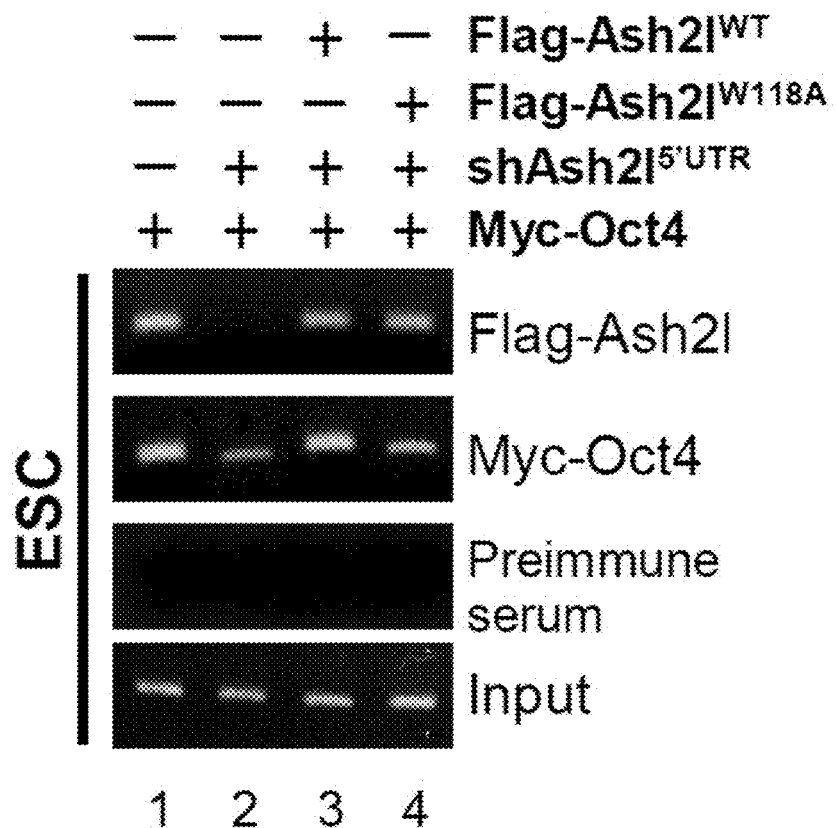

Considering the crucial role of Ash2l-a in pluripotency maintenance and the enrichment of Ash2l-a at the super-enhancers of Jarid2, Nanog, and Oct4, we sought to further examine the effects of Ash2l-a binding on OSN recruitment to super-enhancers and on the regulation of pluripotency genes. Ash2l-a-binding motifs were deleted to interrupt Ash2l-a binding to Jarid2 and Nanog enhancers. First, we used HEK293T cells and introduced reporter plasmids containing either wild-type Jarid2 or Nanog enhancer, or the same enhancers with deleted Ash2l-a-binding motifs (FIGS. 12A and 12B). HEK293T cells per se did not express endogenous Oct4 and provided an excellent platform for the investigation of the interaction between Ash2l-a and Oct4. These cells were subsequently subjected to ChIP-qPCR experiments and luciferase reporter assays (FIG. 12C-12F). For the ChIP-qPCR experiments, we found that overexpression of Flag-tagged Ash2l-WT enhanced the binding of Myc-tagged Oct4 to both Jarid2 and Nanog enhancers (FIGS. 12C and 12E, upper). Overexpression of Flag-tagged Ash2l-a with W118 point mutation (Flag-tagged Ash2l-W118A) abrogated the Ash2l-a-mediated enhancement effect on Myc-tagged Oct4 binding (FIGS. 12C and 12E, upper). In addition, deletion of the Ash2l-a-binding sites on Jarid2 and Nanog super-enhancers also abolished this Ash2l-a-mediated enhancement effect on Myc-tagged Oct4 binding (FIGS. 12C and 12E, lower). For the reporter assay conducted in the same cells, we observed that either Flag-tagged Ash2l-a or Myc-tagged Oct4 alone were capable of direct activation of Jarid2 and Nanog expression (FIGS. 12D and 12F, upper). Co-expression of Flag-tagged Ash2l-a and Myc-tagged Oct4 led to a synergistic effect on the enhancer activity of Jarid2 (FIG. 12D, upper) and Nanog (FIG. 12F, upper), while deletion of Ash2l-a-binding site and overexpression of Flag-tagged Ash2l-W118A abrogated this synergistic effect (FIG. 12D, upper and lower; FIG. 13F, upper and lower). These findings indicated that the Ash2l-a-binding motifs are required for the enhanced Oct4 recruitment at Jarid2 and Nanog super-enhancers, and for the activation of Jarid2 and Nanog enhancers. The Ash2l-a-Oct4 interaction via Ash2l-a W118 residue is critical for mediating this Ash2l-a effect.

Figure 5A:
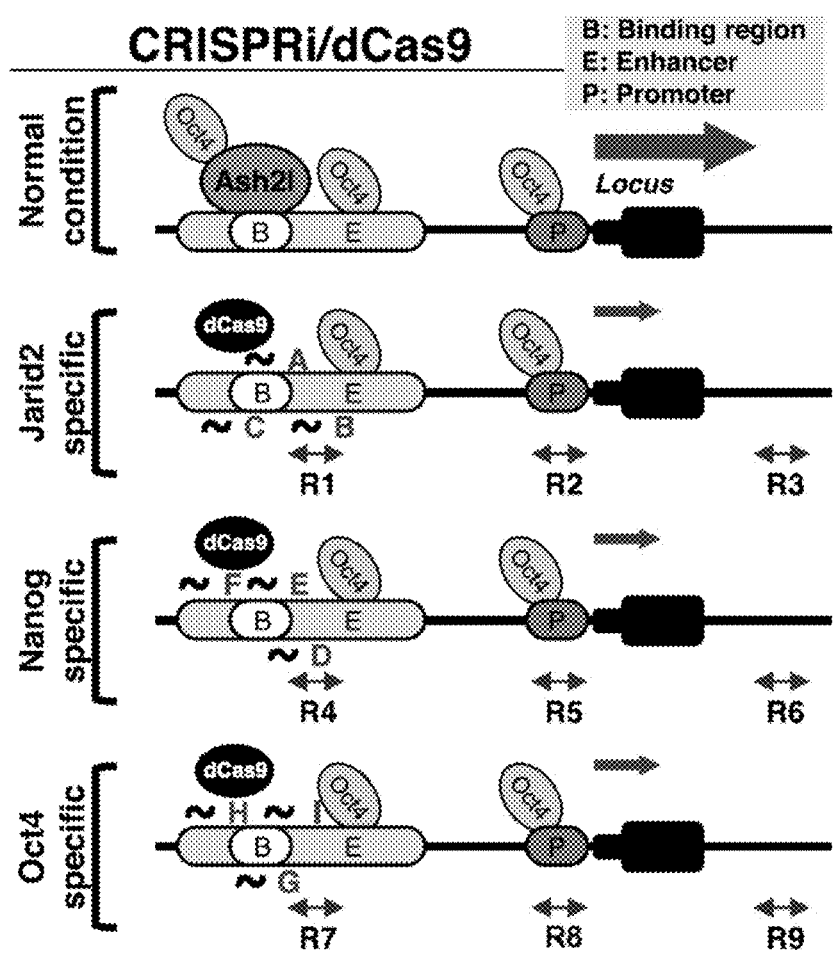
Figure 5B:
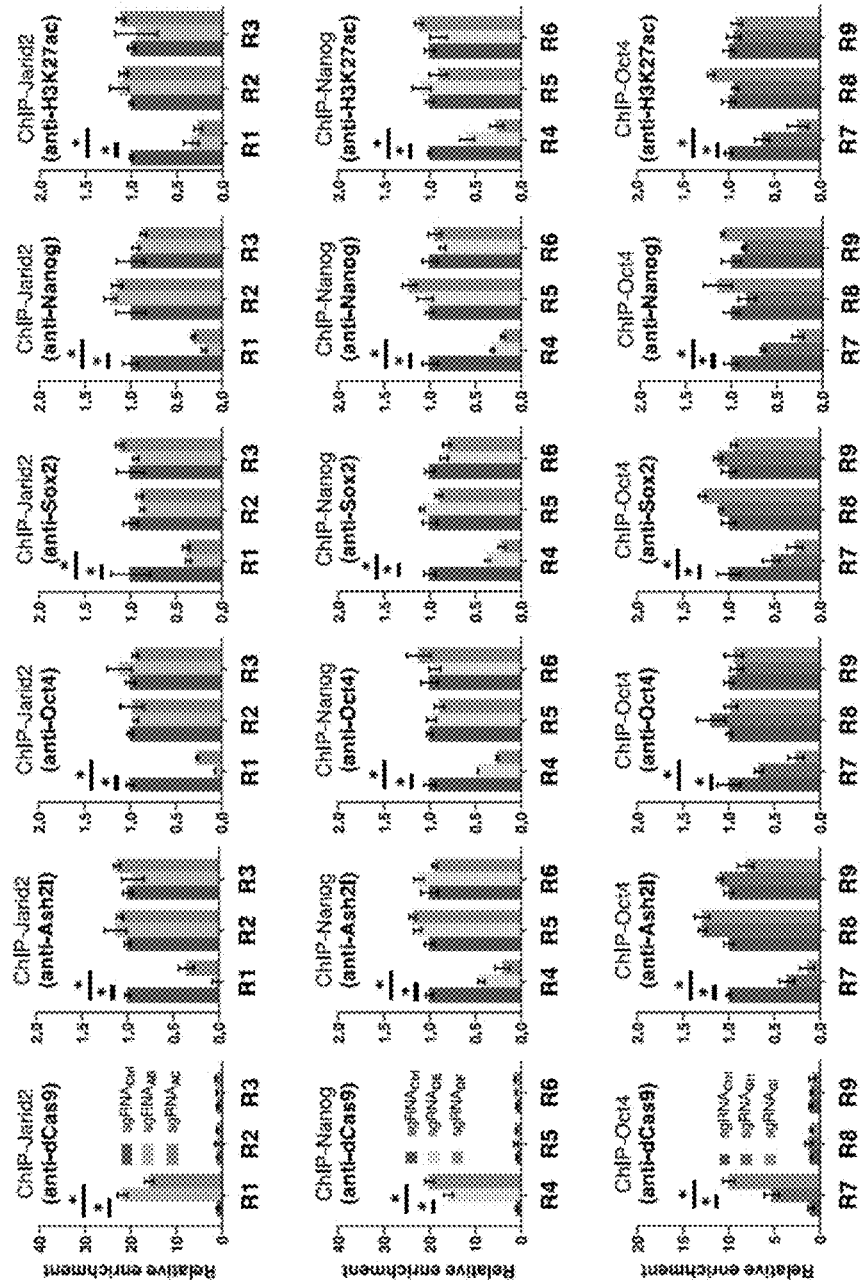
Figure 12H:
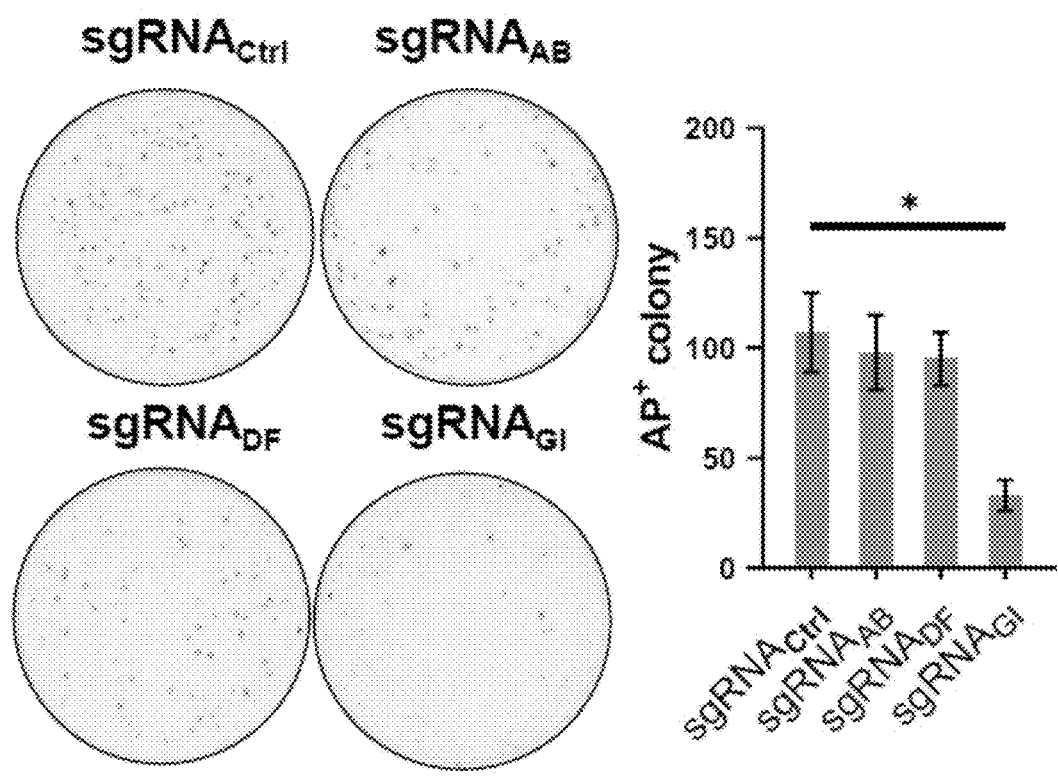
Figure 12I:
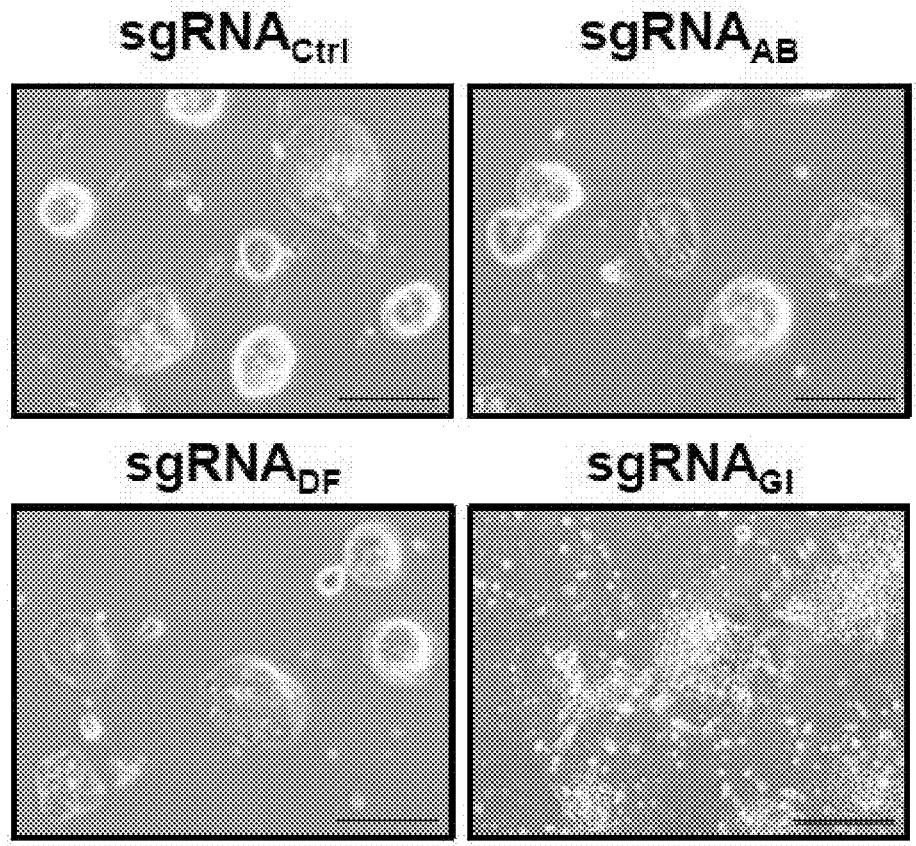

To further validate the effects of Ash2l-a binding to Jarid2 and Nanog super-enhancers in pluripotent stem cells, we applied CRISPRi/dCas9 genomic editing technology to block the accessibility of Ash2l-a-binding sites on Jarid2, Nanog, and Oct4 super-enhancers in ESCs. We designed three sets of sequence-specific short guide RNAs (sgRNAs) for each gene to recognize the Ash2l-a-binding motifs at Jarid2, Nanog, or Oct4 enhancer (FIG. 12G) through either monoallelic silencing (labeled as sgRNA$_{AB}$) or biallelic silencing (labeled as sgRNA$_{AC}$, sgRNA$_{DE}$, sgRNA$_{DF}$, sgRNA$_{GH}$, and sgRNA$_{GI}$) (FIG. 5A). Stably infected clones were selected by antibiotics. After the transfection and selection, infected ESCs were cultivated onto inactivated MEFs for two weeks. Infected ESCs with sgRNAs guiding to the Ash2l-a-binding motifs at Jarid2 or Nanog super-enhancers gradually regained the self-renewal/stemness signature (FIG. 12H), and ESC-specific morphology (FIG. 12I). However, ESCs infected with sgRNAs guiding to Oct4 super-enhancer did not regain the stemness/self-renewal properties (FIG. 12H-I). CRISPRi/dCas9 system can drive the expression of dCas9 protein and directs it to the designed regions. Therefore, the appearance of dCas9 protein and decreased Ash2l-a binding at all given regions in the genome was examined to confirm a successful CRISPRi/dCas9-mediated blocking at indicated sites in the genome. ChIP-qPCR results showed that the three distinct sets of sgRNAs specifically increased dCas9 protein and interfered with Ash2l-a binding at the R1, R4, and R7 regions of Jarid2, Nanog, and Oct4 super-enhancers, respectively (FIG. 5B). These sgRNAs also simultaneously blocked the binding of Ash2l-a to these motifs, and hindered the recruitment of Oct4, Sox2, and Nanog to the enhancer regions (R1, R4, and R7), but not the promoter regions (R2, R5, and R8) and Ash2l-a non-binding regions (R3, R6 and R9) (FIG. 5B). A decrease of H3K27ac histone mark at enhancer regions (R1, R4, and R7), but not promoter regions (R2, R5, and R8) and Ash2l-a non-binding regions (R3, R6 and R9), was also observed upon CRISPR/dCas9-mediated blocking on Jarid2, Nanog, and Oct4 super-enhancers (FIG. 5B).

Figure 5C:
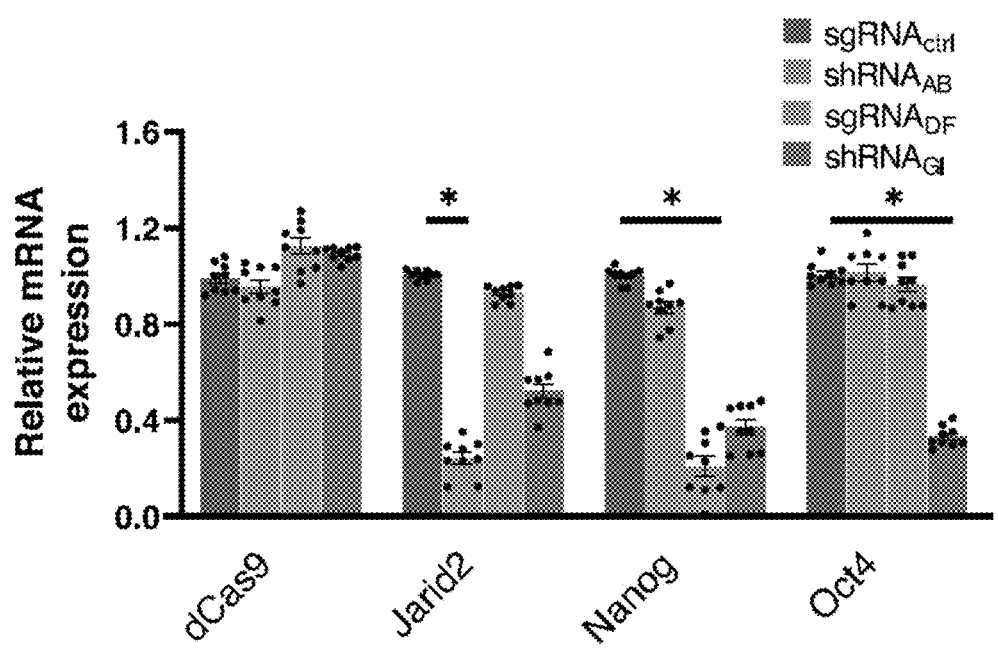
Figure 5D:
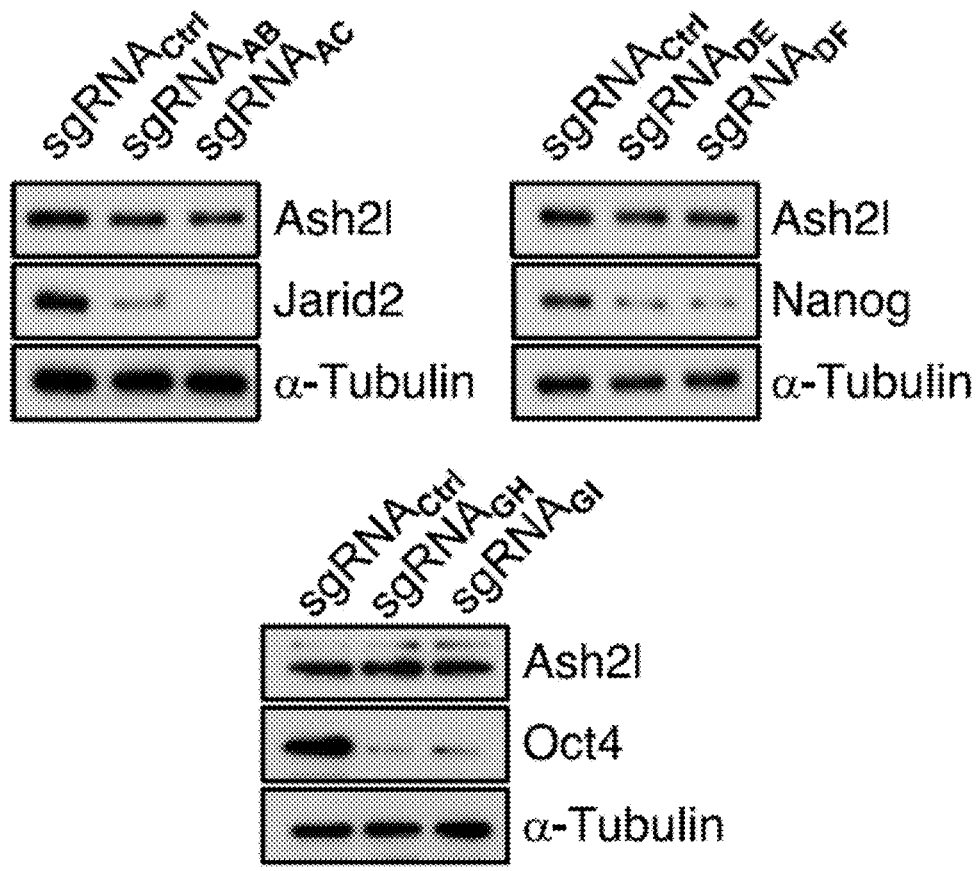

Among the distinct sets of designed sgRNAs, CRISPR/dCas9-mediated blocking by sgRNA$_{AB}$, sgRNA$_{DF}$, and sgRNA$_{GI}$ led to the maximal inhibition on Ash2l-a binding to Jarid2, Nanog, and Oct4 super-enhancers (FIG. 5B). Therefore, sgRNA$_{AB}$, sgRNA$_{DF}$, and sgRNA$_{GI}$ were used in the residual experiments for CRISPR/dCas9-mediated blocking of the Ash2l-a binding. qPCR indicated that CRISPRi/dCas9-mediated blocking with sgRNA$_{AB}$, sgRNA$_{DF}$, and sgRNA$_{GI}$ led to the expected inhibition of Jarid2, Nanog, and Oct4 expression (FIG. 5C). This blocking of Ash2l-a-binding motifs at Jarid2, Nanog, and Oct4 super-enhancers also abrogated Jarid2, Nanog, and Oct4 protein without affecting Ash2l-a levels (FIG. 5D). Similar results of Western blot were also obtained by blocking the binding motifs with sgRNA$_{AC}$, sgRNA$_D$E, and sgRNA$_{GH}$ (FIG. 5D).

Figure 5E:
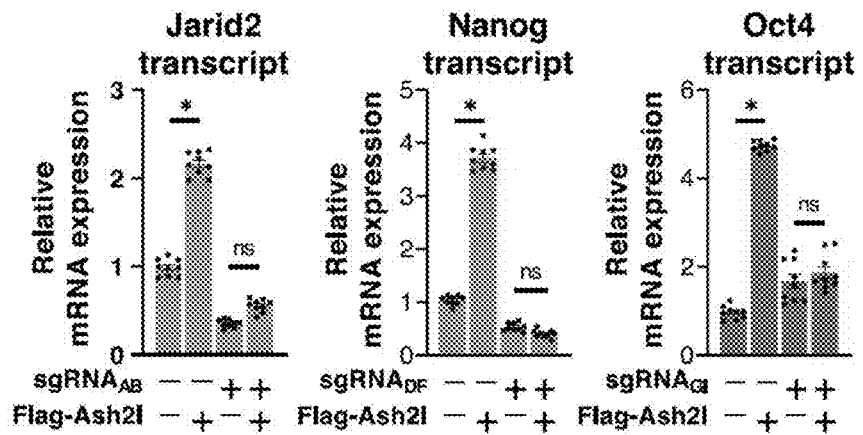
Figure 5F:
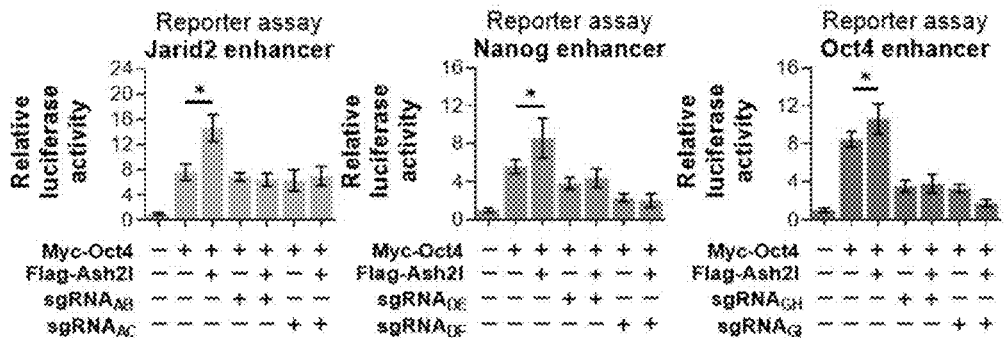

As shown by qPCR, Jarid2, Nanog, and Oct4 transcripts were upregulated by overexpression of Flag-Ash2l-a in ESCs (FIG. 5E). The CRISPRi/dCas9-mediated blocking of the Ash2l-a-binding motif at each enhancer abrogated this upregulation of Jarid2, Nanog, and Oct4 transcripts (FIG. 5E). Furthermore, the effects of CRISPRi/dCas9-mediated blocking on Ash2l-a-binding motifs were also tested in a luciferase reporter assay of the Jarid2, Nanog, or Oct4 super-enhancers. Overexpression of Flag-tagged Ash2l-a synergistically enhanced the Myc-tagged Oct4-induced enhancer activity in Jarid2, Nanog, or Oct4 enhancer (FIG. 5F), and this enhancement can be abolished by the CRISPRi/dCas9-mediated blocking on corresponding Ash2l-a-binding motifs at Jarid2, Nanog, or Oct4 super-enhancer, respectively (FIG. 5F). Taken together, these data indicated that Ash2l-a-binding motifs are essential for Ash2l-a binding to super-enhancers, for the subsequent recruitment of OSN, and for the activation of corresponding enhancer.

Ash2l-a Enhances OSN Recruitment to the Oct4 Super-Enhancer in ESCs.

Figure 6A:
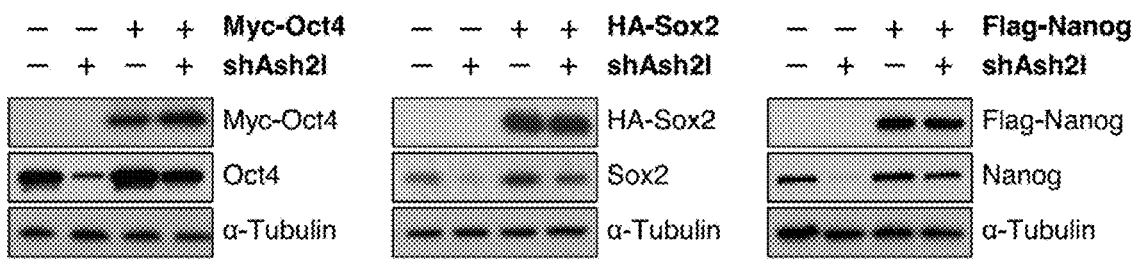
Figure 6B:
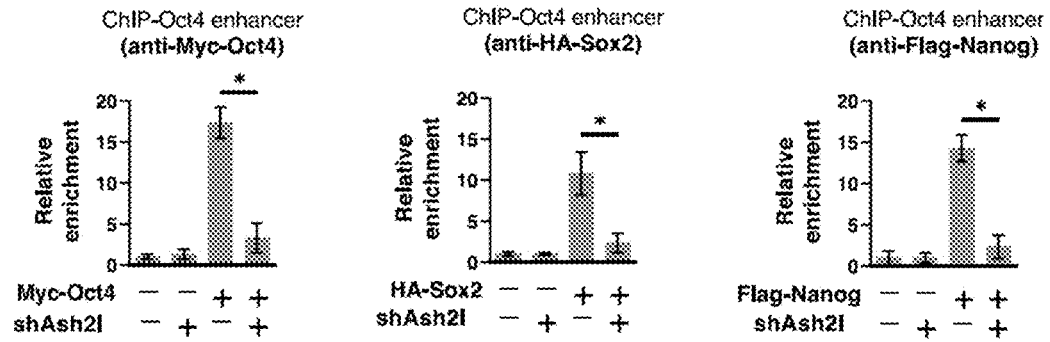

In addition to Jarid2 and Nanog enhancer, we also observed a moderate enrichment of Ash2l-a and OSN at Oct4 super-enhancer. Oct4 has been extensively accepted to be the master pluripotent factor whereas the regulation of Oct4 remained not fully understood. In addition to the CRISPRi/dCas9-mediated interference experiments at Oct4 super-enhancer (FIG. 5), we conducted further experiments to validate whether Ash2l-a could also recruit OSN and form Ash2l-a/OSN complex at Oct4 super-enhancer to increase Oct4 enhancer activity. We evaluated and compared the OSN recruitment to Oct4 super-enhancer in ESCs with or without Ash2l-a knockdown. As Ash2l-a is also an upstream regulator of Oct4, Sox2, and Nanog (FIG. 4K), exogenously expressed Myc-tagged Oct4, HA-tagged Sox2, and Flag-tagged Nanog were employed to carry out the experiments without the confounding by down-regulation of endogenous OSN. Ash2l-a depletion had no effect on the protein levels of exogenous Myc-tagged Oct4, HA-tagged Sox2, and Flag-tagged Nanog (FIG. 6A) but reduced their binding ability to Oct4 super-enhancer (FIG. 6B). The similar effect of Ash2l-a depletion on OSN recruitment was observed at Jarid2 and Nanog super-enhancers (FIG. 13A-B). Moreover, Ash2l-a depletion reduced the recruitment of p300 and Med1 to these super-enhancers (FIG. 13C) without affecting the p300 and Med1 protein amounts (FIG. 4K). Remarkably, transfection of recombinant wild-type Ash2l-a (Flag-Ash2l$^{WT}$), but not recombinant Ash2l-a with W118A mutation (Flag-Ash2l$^{W118}$), rescued the decreased OSN recruitment in Ash2l-a depleted cells (FIG. 13D-13E). These findings supported that Ash2l-a recruited OSN to Oct4, Jarid2, and Nanog super-enhancers, and that Ash2l-a-Oct4 interaction is crucial for OSN recruitment at super-enhancers.

Figure 2I:
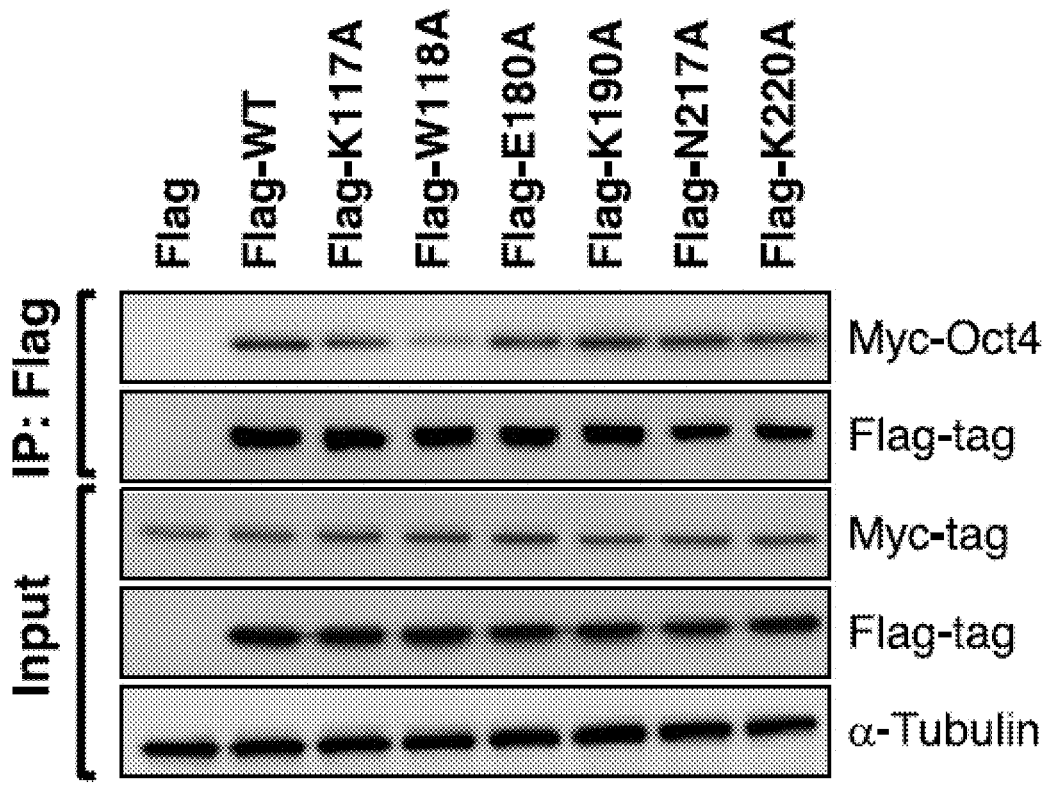
Figure 2J:
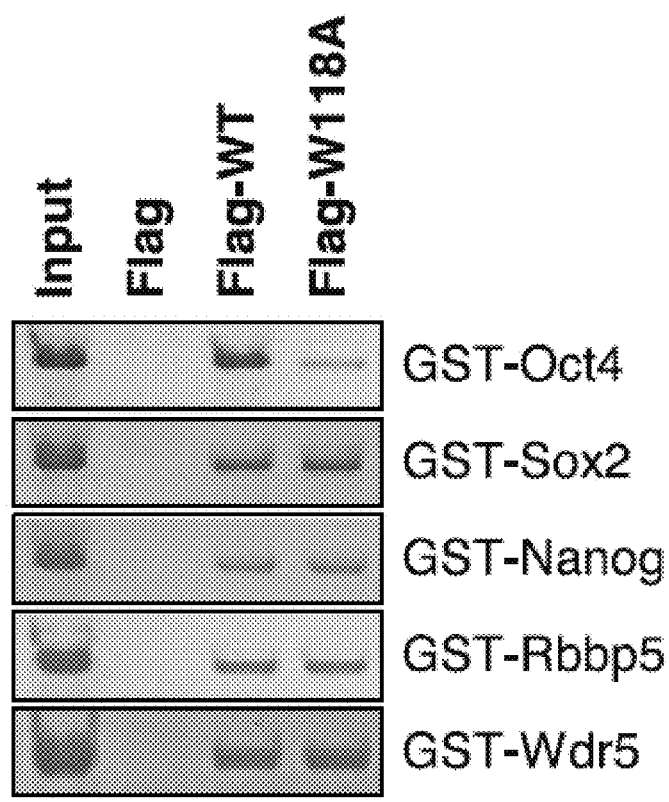
Figure 6F:
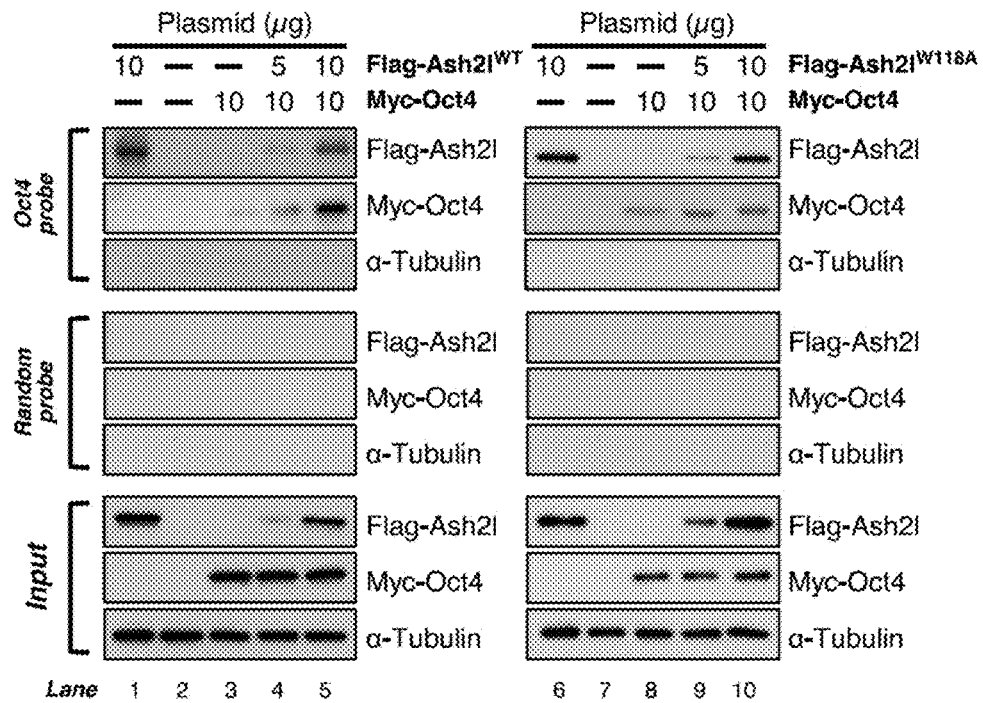
Figure 6G:
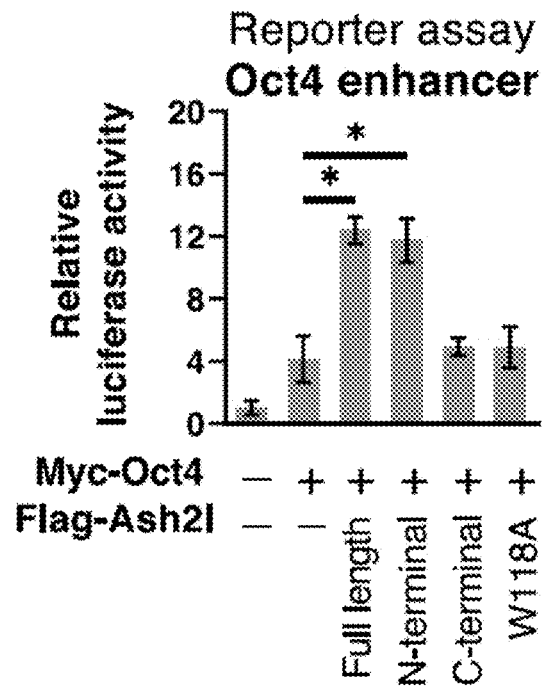
Figure 6H:
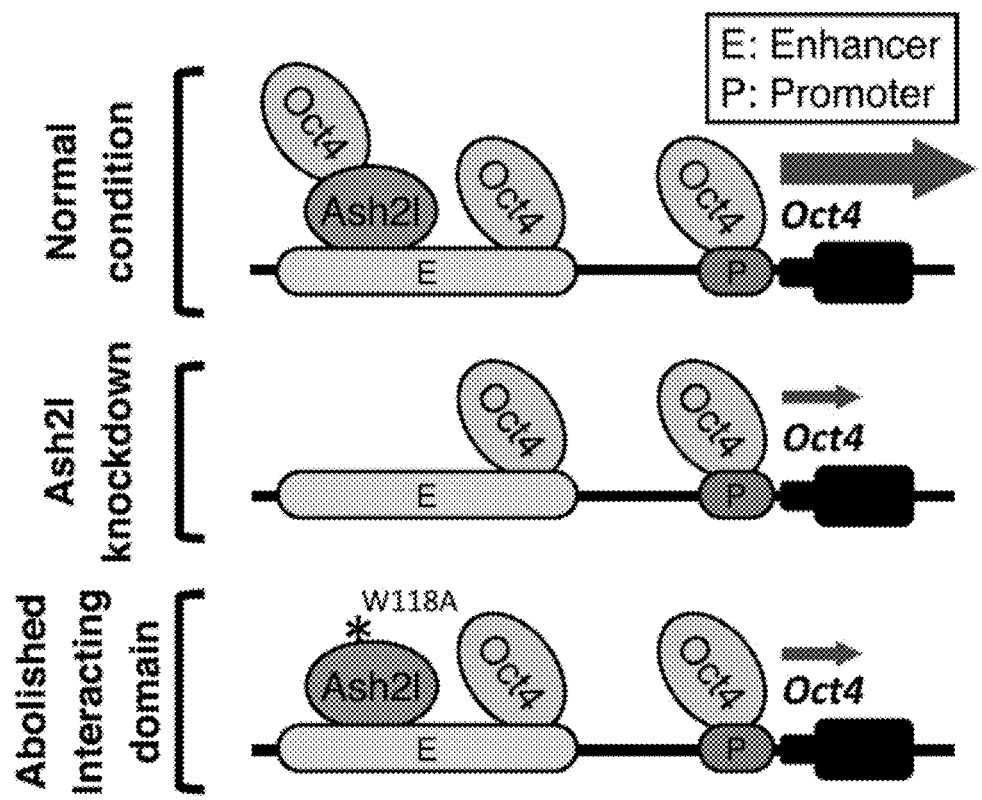
Figure 13G:
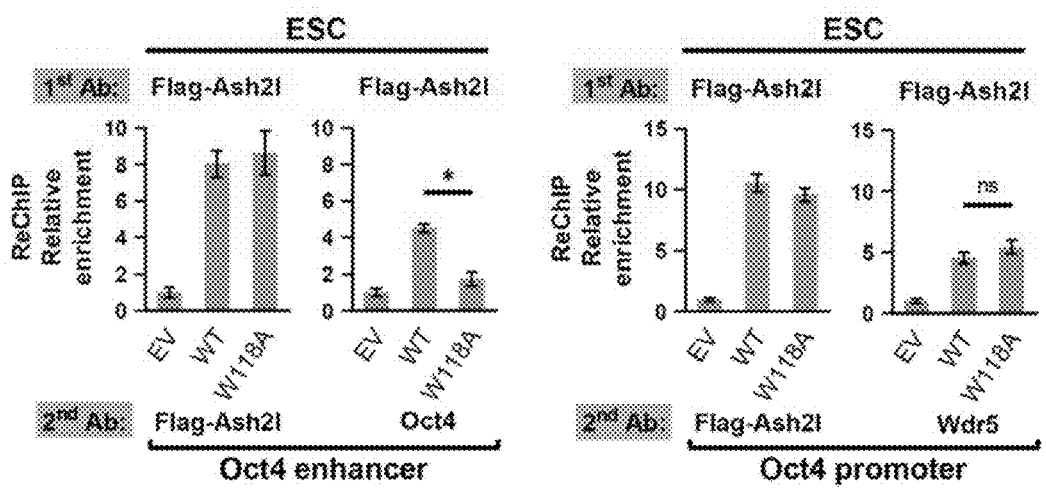

We next attempted to elucidate in detail how Ash2l-a regulated Oct4 expression in ESCs through the cis-regulatory elements. We found that Ash2l-a knockdown only reduced Oct4 recruitment to its own enhancer but not promoter and Desert (FIG. 6C). To confirm the importance of Ash2l-a on Oct4 binding to its own super-enhancer, we transfected a plasmid containing the Oct4 enhancer sequence into HEK293T cells and assessed the binding capacity of Flag-tagged Ash2l-a and Myc-tagged Oct4 to this sequence. ChIP-reverse transcription-PCR (ChIP-RT-PCR) experiments showed that Ash2l-a enhanced the binding of Myc-tagged Oct4 to its own enhancer (FIG. 6D, comparing lane 5 with lane 3), but not at the Oct4 promoter (FIG. 6D, comparing lane 10 with lane 8). We further validated that recombinant Ash2l-a with W118A mutation (Flag-Ash2l$^{W118}$) failed to recruit Oct4 to enhancer (FIG. 6D, comparing lane 20 with lane 18). Similar results were obtained in ESCs (FIG. 13F). We further performed an in vitro DNA-affinity pull-down assay (DAPA) by incubating an oligonucleotide probe containing the Oct4 enhancer sequence with Ash2l-a and Oct4 recombinant proteins (FIG. 6E). Without recombinant Oct4 protein, recombinant Ash2l-a per se directly bound the Oct4 probe (FIG. 6F, lane 1). Increasing the amount of recombinant Ash2l-a protein enhanced the binding of recombinant Oct4 protein to Oct4 probe in a dose-dependent manner (FIG. 6F, lane 4 and 5). Flag-Ash2l$^{W118}$ also bound the Oct4 probe (FIG. 6F, lane 6), but failed to recruit recombinant Oct4 protein to Oct4 probe (FIG. 6F, lane 10 compared with lane 8). Moreover, we sought to demonstrate whether Ash2l-a-recruited Oct4 indeed has the function to stimulate Oct4 enhancer activity. A reporter plasmid containing the Oct4 enhancer was transfected into HEK293T cells with Oct4 and full-length Ash2l-a, truncated Ash2l-a (Ash2l-N terminus or Ash2l-C terminus), or Flag-Ash2l$^{W118}$ expression vectors; the luciferase activity representing the activity of Oct4 enhancer was then quantified. We observed that full-length Ash2l-a or Ash2l-N terminus indeed enhanced Oct4-stimulated luciferase activity, while Ash2l-C terminus or Ash2l-a with W118A mutation had no effect on Oct4-stimulated luciferase activity (FIG. 6G). These observations were consistent with the capability of each Ash2l-a variant to recruit Oct4 as we previously showed (FIG. 2E-F, 2I). Furthermore, Re-ChIP assay revealed that W118 mutation of Ash2l-a specifically interfered with Ash2l-a binding to Oct4 at Oct4 enhancer but did not affect its binding to Wdr5 at Oct4 promoter (FIG. 13G). Collectively, our findings demonstrated that Ash2l-a acts as an upstream regulator of Oct4 expression in a pluripotent state, predominantly by enhancing OSN recruitment to the Oct4 super-enhancer via its N-terminus. Upon Ash2l-a knockdown or disruption of Ash2l-a-Oct4 interaction by W118 point mutation, Oct4 is neither recruited nor bound to its own super-enhancer, and therefore the Oct4 super-enhancer was not activated (FIG. 6H).

Ash2l-a-Oct4 Interaction Via W118 Residue is Crucial for the Ash2l-a-Mediated Pluripotent Network.

Figure 7A:
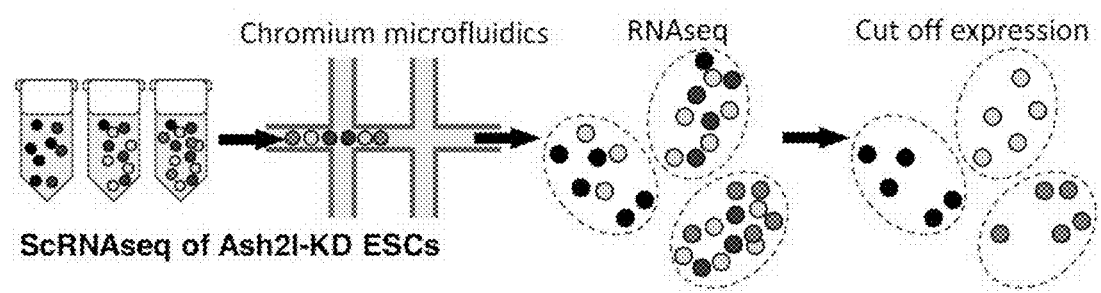
Figure 7B:
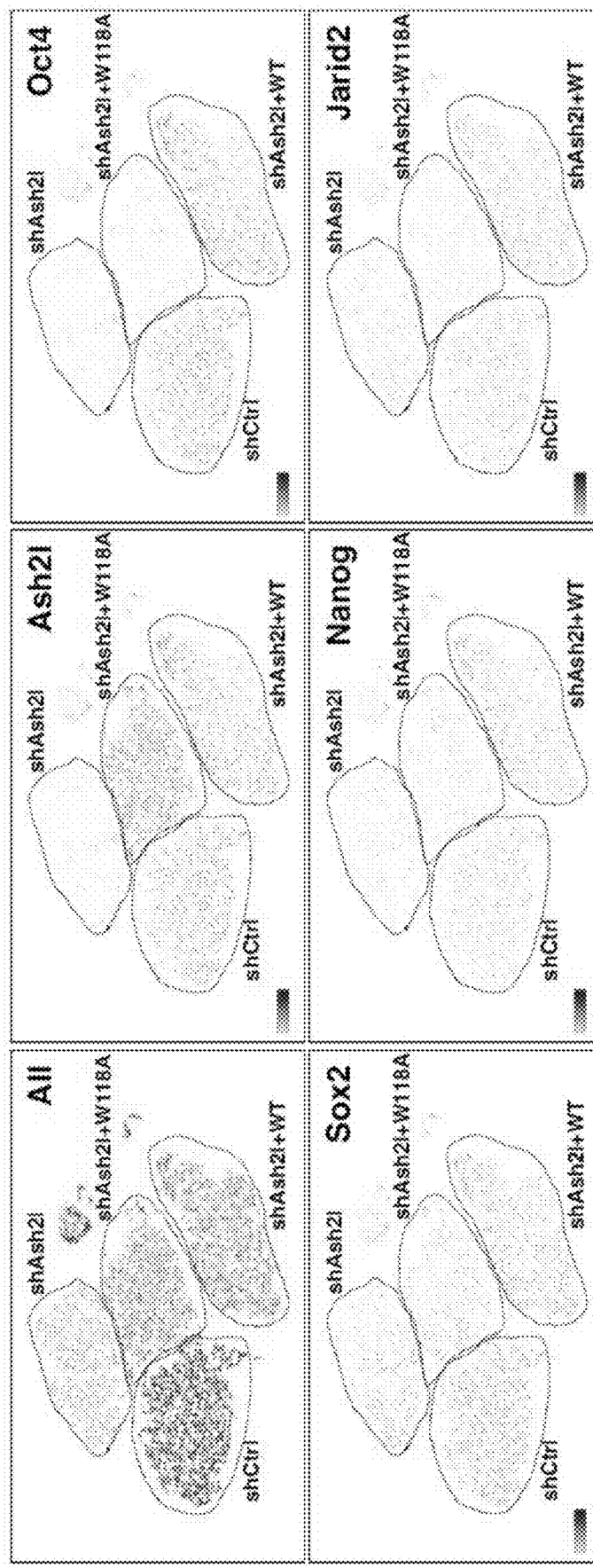
Figure 7C:
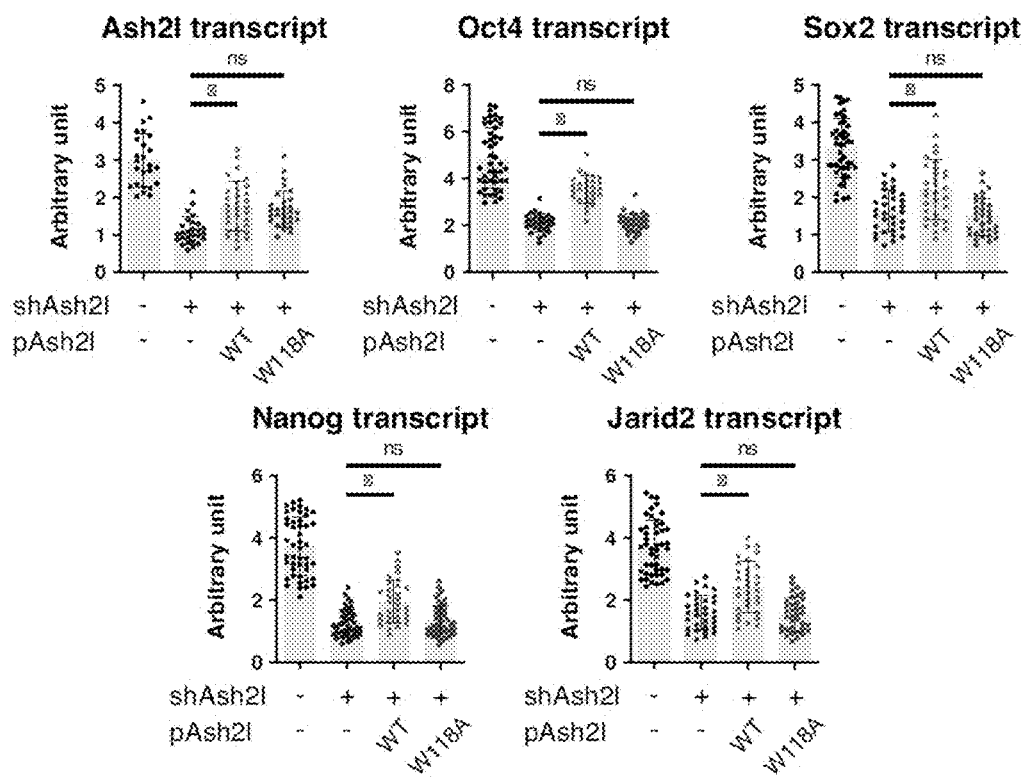
Figure 7D:
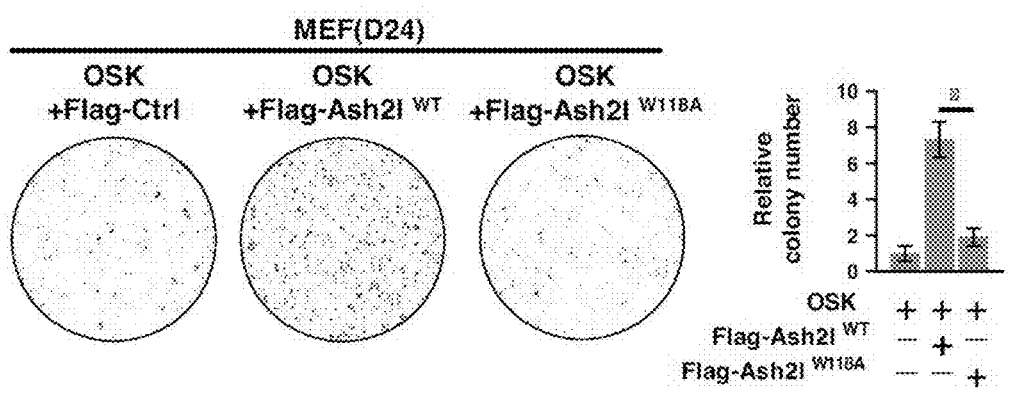

Based on the data of molecular docking simulation and point mutation studies, we identified that W118 is the crucial residue responsible for the Ash2l-a-Oct4 interaction and the Ash2l-a-mediated enhancement of Oct4 binding at the super-enhancers for stimulating the activity of enhancers of Oct4, Jarid2, and Nanog genes (FIG. 6D-G; FIGS. 12C-12F, 13D-13G). These results suggested that Ash2l-a-recruited enhancer-bound Oct4 is crucial for Ash2l-a-mediated stemness circuitry and pluripotency maintenance. To illustrate the role of Ash2l-a-Oct4 interaction in pluripotency, we next investigated the functional consequences of disrupting Ash2l-a-Oct4 interaction in the whole picture of Ash2l-a-mediated pluripotency network. Single cell RNA-seq is a powerful tool for the measurement of gene expression at individual cell level and the study of cellular heterogeneity. To elucidate the transcriptional networks among Jarid2, Nanog, and stemness factors, ESCs with Ash2l-a knockdown and concomitant overexpression of Flag-Ash2l$^{WT}$ or Flag-Ash2l$^{W118A}$ were subjected to single cell-seq analysis (scRNA-seq; FIG. 7A). We analyzed transcriptomes from 3000 ESCs with various treatments, and t-distributed stochastic neighbor embedding (t-SNE) was used to reduce dimension for clustering and visualization. Ash2l-a knockdown decreased the transcripts of Oct4, Sox2, Nanog, and Jarid2 (FIG. 7B-C). Comparing with scRNA-seq profiles in ESCs with Ash2l-a knockdown, we observed that only Flag-Ash2l$^{WT}$ but not Flag-Ash2l$^{W118A}$ could rescue the expression of Ash2l-a, Oct4, Sox2, Jarid2 and Nanog transcripts (FIGS. 7B and 7C). These data indicated that Ash2l-a-Oct4 interaction is crucial for the upregulation of Oct4, Sox2, Jarid2, and Nanog in pluripotent state. To further validate the functions of Ash2l-a-Oct4 interaction in pluripotency, Flag-Ash2l$^{WT}$ or Flag-Ash2l$^{W118A}$ was overexpressed in MEFs and these cells were then subjected to OSK-mediated reprogramming (FIG. 7D). At day 24 post-reprogramming, overexpression of Flag-Ash2l$^{WT}$ but not Flag-Ash2l$^{W118A}$, enhanced the reprogramming efficiency, compared with MEFs infected with Oct4/Sox2/Klf4 only (FIG. 7D). Collectively, these data demonstrated that Ash2l-a-Oct4 interaction through Ash2l-a W118 residue governs the recruitment of Oct4 to the super-enhancers of downstream target genes, the subsequent activation of downstream genes and pluripotent network.

CONCLUSION

Figure 7E:
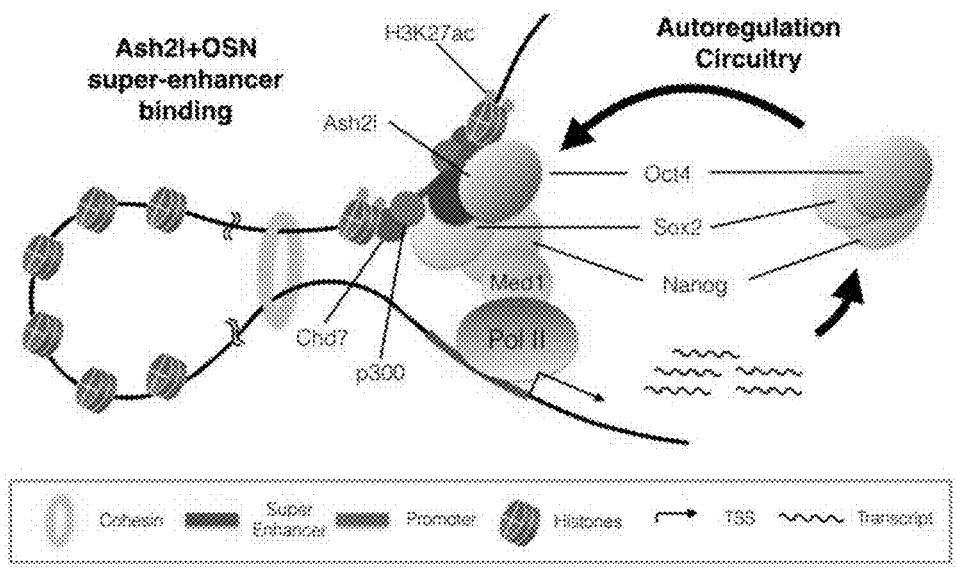

Super-enhancers are the genomic region that contains multiple putative enhancers to drive gene expression and control cell identity, as well as regulate stem cell-specific phenotypes in pluripotent cells. Pluripotent transcription factors are reported to functionally pre-mark and activate the cell-type-restricted enhancers (28). A dynamic interplay of enhancer elements plays crucial roles in the maintenance of pluripotent state via regulating the expression of stemness factors such as Klf4 (30). It has been shown that super-enhancers are enriched for Oct4, Sox2, and Nanog (OSN), which can subsequently form an OSN complex. However, the mechanisms for the enrichment of OSN on the super-enhancers and the role of this complex were not fully understood. In the present study, we demonstrated that Ash2l-a recruited OSN to the super-enhancers and formed an Ash2l-a/OSN complex to regulate pluripotency. This Ash2l-a/OSN complex at super-enhancers is distinct from the well-known Wdr5/Ash2l-a/Rbbp5/Dpy30 (WARD) complex, which localizes near the TSS. The physical interaction between Ash2l-a and Oct4 in this complex predominantly depends on the W118 residue at N-terminus of Ash2l-a. After forming the Ash2l-a/OSN complex, several downstream stemness-associated genes were activated, including Jarid2, Nanog and Oct4. Ash2l-a knockdown, disruption of Ash2l-a-binding motifs, and the CRISPRi/dCas9-mediated blocking of the binding motifs showed the crucial role of Ash2l-a in forming the complex and in regulating downstream pluripotency gene expression. Together, our data demonstrate that Ash2l-a forms a novel complex with master pluripotent transcription factors OSN to regulate Oct4-associated stemness circuitry and control the pluripotency network (FIG. 7E). The protein members of WARD complex have been reported to physically and functionally interact with key stemness-related transcription factors to promote cellular pluripotency (14). Apart from the well-defined interaction between Wdr5 and Oct4 (16), Ash2l has been shown to interact with Sox2 and Klf4, evidenced by protein co-immunoprecipitation in 293T cells (31). In the human osteosarcoma U2OS cell line, Ash2l could form a complex with Myc to mediate gene transcription efficiency through their promoters (32). These reports regarding the interaction between WARD complex and stemness factors mostly focused on their regulatory role at gene promoters. Ash2l as a member of WARD complex has been previously demonstrated to maintain chromatin opening and pluripotency via its binding to promoter and the induction of H3K4 tri-methylation (15,17). In the WARD complex, Ash2l mediates and enhances the H3K4 trimethylation activity, while Wdr5 maintains the integrity of WARD (15). In this study, we found that Ash2l-a recruited OSN and formed a stable complex at super-enhancers without the involvement of Wdr5. This discrepancy revealed that the functional roles of Ash2l-a in the WARD complex and Ash2l-a/OSN complex were diverse. Further experiments are required to identify the differences in the binding specificity of Ash2l-a in the two Ash2l-a-associated complexes in different gene loci.

Figure 9D:
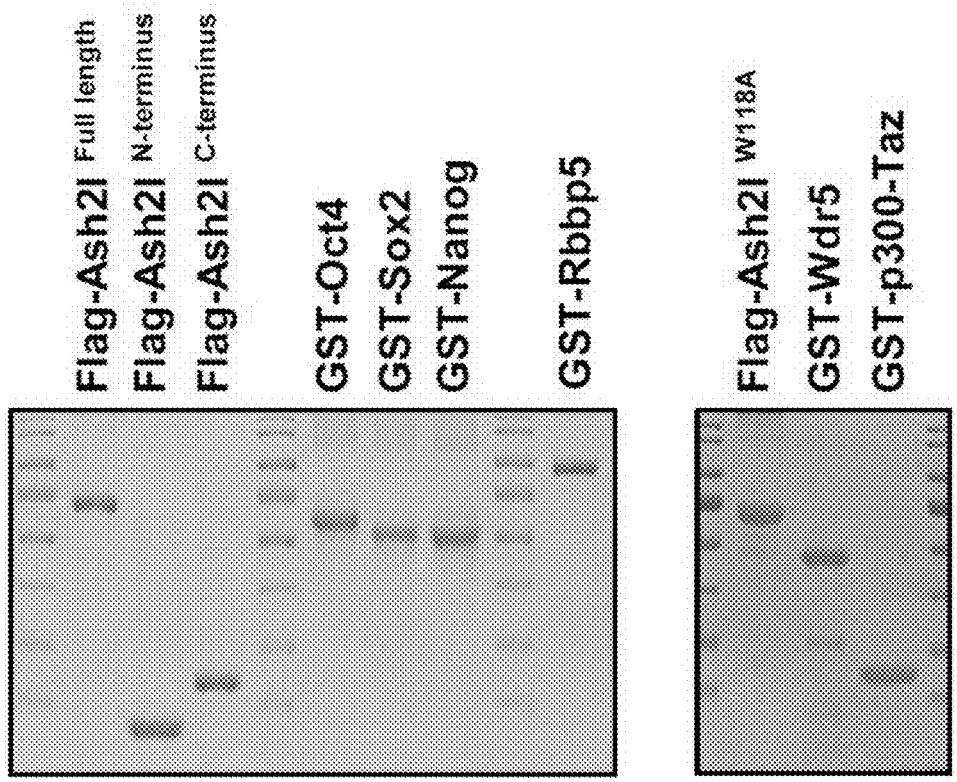

Among all stemness factors, Oct4 is known to be the most pivotal factor. However, the mechanisms by which regulates Oct4 expression is still not fully understood. We observed that Ash2l-a directly binds to and recruits OSN to Oct4 super-enhancer in order to stimulate Oct4 expression (FIG. 7), indicating that Ash2l-a is the direct upstream activator of Oct4. Oct4 protein amount was largely diminished in Ash2l-a-knockdown ESCs (FIGS. 1H and 4K) also supporting this point. In addition, we found that the interaction between Ash2l-a and Oct4 plays a crucial role in Ash2l-a-mediated Oct4 activation. The Ash2l-a/Oct4 interaction was first demonstrated in ESCs (6). In the present study, molecular docking simulation and point mutation study revealed that the W118 residue of Ash2l-a is essential for the Ash2l-a/Oct4 interaction (FIG. 2H-J; FIG. 9C-9D), as it is responsible for ~79.2% Ash2l-a/Oct4 binding (FIG. 2I). Through the protein interaction of Ash2l-a with Oct4, the binding of Ash2l-a to super-enhancers recruit and enhance Oct4 binding to the same region, leading to augmented enhancer activation (FIG. 5F and FIG. 6G). The ChIP-seq data and the aggregation profiles revealed this region co-bound by OA at the Distal II elements were enriched for OSN, H3K27 acetylation, and several enhancer-binding proteins (Med1, p300, and Chd7, etc.; FIG. 3). This Ash2l-a binding allows these enhancer-binding proteins to localize to the same region and catalyze histone H3K27 acetylation to create an open chromatin structure and activate transcription. Mutation of Ash2l-a W118 residue largely hampered the Ash2l-a-Oct4 interaction, and hindered the Oct4 recruitment to super-enhancers for activating the stemness genes and maintaining pluripotency. These findings indicated that Ash2l-a drives stemness circuitry and pluripotency maintenance predominantly via its physical interaction with Oct4. Interestingly, Ash2l-a protein was detected in all given fractions of ESC nuclear extracts (FIG. 2B), implying the existence of other unknown Ash2l-a-associated complexes that remain to be explored. In conclusion, we unraveled an Ash2l-a/OSN-driven circuitry that enhances the expression of core pluripotent genes and promotes cellular reprogramming through epigenetically activating the super-enhancer activity of downstream stemness genes. In addition to Oct4, Sox2 and Nanog are also partner proteins in the Ash2l-a/OSN complex. Whether the Ash2l-a-Sox2 and/or Ash2l-a-Nanog interaction are equally crucial for the pluripotency regulation remains not clear. Future works will be needed to elucidate the roles of Ash2l-a-Sox2 and Ash2l-a-Nanog interaction in the Ash2l-a-mediated pluripotent network.

REFERENCES

1. Ivanova, N. Dobrin, R., Lu, R., Kotenko, I., Levorse, J., DeCoste, C., Schafer, X., Lun, Y and Lemischka, I. R. (2006) Dissecting self-renewal in stem cells with RNA interference. *Nature*, 442, 533-538.
2. Tam, W. L. and Lim, B. (2008), StemBook, Cambridge (MA).
3. Kim, J. B., Zaehres, H., Wu, G., Gentile, L., Ko, K., Sebastiano, V, Arauzo-Bravo, M. J., Ruau, D., Han, D. W., Zenke, M. et al. (2008) Pluripotent stem cells induced from adult neural stem cells by reprogramming with two factors. *Nature*, 454, 646-650.
4. Huangfu, D., Osafune, K., Maehr, R., Guo, W., Eijkelenboom, A., Chen, S., Muhlestein, W. and Melton, D. A. (2008) Induction of pluripotent stem cells from primary human fibroblasts with only Oct4 and Sox2. *Nat Biotechnol*, 26, 1269-1275.
5. Adachi, K., Kopp, W., Wu, G., Heising, S., Greber, B., Stehling, M., Arauzo-Bravo, M. J., Boerno, S. T., Timmermann, B., Vingron, M. et al. (2018) Esrrb Unlocks Silenced Enhancers for Reprogramming to Naive Pluripotency. *Cell Stem Cell*, 23, 266-275.e266.
6. Ding, J., Xu, H., Faiola, F., Ma'ayan, A. and Wang, J. (2012) Oct4 links multiple epigenetic pathways to the pluripotency network. *Cell Res*, 22, 155-167.
7. Hnisz, D., Abraham, B. J., Lee, T. I., Lau, A., Saint-Andre, V, Sigova, A. A., Hoke, H. A. and Young, R. A. (2013) Super-enhancers in the control of cell identity and disease. *Cell*, 155, 934-947.
8. Whyte, W. A., Orlando, D. A., Hnisz, D., Abraham, B. J., Lin, C. Y, Kagey, M. H., Rahl, P. B., Lee, T. I. and Young, R. A. (2013) Master transcription factors and mediator establish super-enhancers at key cell identity genes. *Cell*, 153, 307-319.
9. Tsankov, A. M., Gu, H., Akopian, V, Ziller, M. J., Donaghey, J., Amit, I., Gnirke, A. and Meissner, A. (2015) Transcription factor binding dynamics during human ES cell differentiation. *Nature*, 518, 344-349.
10. Ding, J., Huang, X., Shao, N., Zhou, H., Lee, D. F., Faiola, F., Fidalgo, M., Guallar, D., Saunders, A., Shliaha, P. V. et al. (2015) Tex10 Coordinates Epigenetic Control of Super-Enhancer Activity in Pluripotency and Reprogramming. *Cell Stem Cell*, 16, 653-668.
11. Choi, H. W., Joo, J. Y, Hong, Y J., Kim, J. S., Song, H., Lee, J. W., Wu, G., Scholer, H. R. and Do, J. T. (2016) Distinct Enhancer Activity of Oct4 in Naive and Primed Mouse Pluripotency. *Stem cell reports*, 7, 911-926.
12. Liu, P., Chen, M., Liu, Y, Qi, L. S. and Ding, S. (2018) CRISPR-Based Chromatin Remodeling of the Endogenous Oct4 or Sox2 Locus Enables Reprogramming to Pluripotency. *Cell Stem Cell*, 22, 252-261.e254.
13. Takahashi, Y H., Westfield, G. H., Oleskie, A. N., Trievel, R. C., Shilatifard, A. and Skiniotis, G. (2011) Structural analysis of the core COMPASS family of histone H3K4 methylases from yeast to human. *Proc Natl Acad Sci USA*, 108, 20526-20531.
14. Ernst, P. and Vakoc, C. R. (2012) WRAD: enabler of the SET1-family of H3K4 methyltransferases. *Brief Funct Genomics*, 11, 217-226.
15. Steward, M. M., Lee, J. S., O'Donovan, A., Wyatt, M., Bernstein, B. E. and Shilatifard, A. (2006) Molecular regulation of H3K4 trimethylation by ASH2L, a shared subunit of MLL complexes. *Nature structural & molecular biology*, 13, 852-854.
16. Ang, Y S., Tsai, S. Y, Lee, D. F., Monk, J., Su, J., Ratnakumar, K., Ding, J., Ge, Y, Darr, H., Chang, B. et al. (2011) Wdr5 mediates self-renewal and reprogramming via the embryonic stem cell core transcriptional network. *Cell*, 145, 183-197.
17. Wan, M., Liang, J., Xiong, Y, Shi, F., Zhang, Y, Lu, W., He, Q., Yang, D., Chen, R., Liu, D. et al. (2013) The trithorax group protein Ash2l is essential for pluripotency and maintaining open chromatin in embryonic stem cells. *J Biol Chem*, 288, 5039-5048.
18. Dou, Y, Milne, T. A., Ruthenburg, A. J., Lee, S., Lee, J. W., Verdine, G. L., Allis, C. D. and Roeder, R. G. (2006) Regulation of MLL1 H3K4 methyltransferase activity by its core components. *Nat Struct Mol Biol*, 13, 713-719.
19. Chiou, S. H., Jiang, B. H., Yu, Y L., Chou, S. J., Tsai, P. H., Chang, W. C., Chen, L. K., Chen, L. H., Chien, Y and Chiou, G. Y (2013) Poly(ADP-ribose) polymerase 1 regulates nuclear reprogramming and promotes iPSC generation without c-Myc. *J Exp Med*, 210, 85-98.
20. Sung, L. Y, Gao, S., Shen, H., Yu, H., Song, Y, Smith, S. L., Chang, C. C., Inoue, K., Kuo, L., Lian, J. et al. (2006) Differentiated cells are more efficient than adult stem cells for cloning by somatic cell nuclear transfer. *Nat Genet*, 38, 1323-1328.
21. Chen, P. B., Hung, J. H., Hickman, T. L., Coles, A. H., Carey, J. F., Weng, Z., Chu, F. and Fazzio, T. G. (2013) Hdac6 regulates Tip60-p400 function in stem cells. *Elife*, 2, e01557.
22. Grant, C. E., Bailey, T. L. and Noble, W. S. (2011) FIMO: scanning for occurrences of a given motif. *Bioinformatics*, 27, 1017-1018.

23. Mi, H., Muruganujan, A., Casagrande, J. T. and Thomas, P. D. (2013) Large-scale gene function analysis with the PANTHER classification system. *Nat Protoc,* 8, 1551-1566.
24. Core, L. J., Waterfall, J. J. and Lis, J. T. (2008) Nascent RNA sequencing reveals widespread pausing and divergent initiation at human promoters. *Science,* 322, 1845-1848.
25. Hah, N., Danko, C. G., Core, L., Waterfall, J. J., Siepel, A., Lis, J. T. and Kraus, W. L. (2011) A rapid, extensive, and transient transcriptional response to estrogen signaling in breast cancer cells. *Cell,* 145, 622-634.
26. Chen, Y, Cao, F., Wan, B., Dou, Y and Lei, M. (2012) Structure of the SPRY domain of human Ash2L and its interactions with RbBP5 and DPY30. *Cell Res,* 22, 598-602.
27. Boyer, L. A., Lee, T. I., Cole, M. F., Johnstone, SE., Levine, S. S., Zucker, J. P., Guenther, M. G., Kumar, R. M., Murray, H. L., Jenner, R. G. et al. (2005) Core transcriptional regulatory circuitry in human embryonic stem cells. *Cell,* 122, 947-956.
28. Kim, H. S., Tan, Y, Ma, W., Merkurjev, D., Destici, E., Ma, Q., Suter, T., Ohgi, K., Friedman, M., Skowronska-Krawczyk, D. et al. (2018) Pluripotency factors functionally premark cell-type-restricted enhancers in ES cells. *Nature,* 556, 510-514.
29. Blinka, S., Reimer, M. H., Jr., Pulakanti, K. and Rao, S. (2016) Super-Enhancers at the Nanog Locus Differentially Regulate Neighboring Pluripotency-Associated Genes. *Cell Rep,* 17, 19-28.
30. Xie, L., Torigoe, SE., Xiao, J., Mai, D. H., Li, L., Davis, F. P., Dong, P., Marie-Nelly, H., Grimm, J., Lavis, L. et al. (2017) A dynamic interplay of enhancer elements regulates Klf4 expression in naive pluripotency. *Genes Dev,* 31, 1795-1808.
31. Yang, Z., Augustin, J., Hu, J. and Jiang, H. (2015) Physical Interactions and Functional Coordination between the Core Subunits of Set1/Mll Complexes and the Reprogramming Factors. *PLoS One,* 10, e0145336.
32. Ullius, A., Luscher-Firzlaff, J., Costa, I. G., Walsemann, G., Forst, A. H., Gusmao, E. G., Kapelle, K., Kleine, H., Kremmer, E., Vervoorts, J. et al. (2014) The interaction of MYC with the trithorax protein ASH2L promotes gene transcription by regulating H3K27 modification. *Nucleic acids research,* 42, 6901-6920.

We claim:

1. A method for preparing induced pluripotent stem cells (iPSCs) from somatic cells, comprising:
    (a) transfecting or transducing into isolated somatic cells (i) Ash21-a and (ii) Klf4, Sox2, and Oct4; and
    (b) culturing the isolated somatic cells as obtained in step (a) under appropriate conditions, thereby converting the somatic cells into iPSCs and maintaining pluripotency and self-renewal ability.

2. The method of claim 1, wherein Ash21-a or a complex including Ash21-a_binds to super-enhancers of Jarid2, Nanog and Oct4.

3. The method of claim 1, wherein the isolated somatic cells are transfected or transduced with one or more plasmid or vector comprising Ash21-a, Klf4, Sox2, or Oct4, operably linked to a promoter.

4. The method of claim 3, wherein the vector is a viral vector.

5. The method of claim 1, wherein the isolated somatic cells are transfected by electroporation.

6. The method of claim 5, wherein the isolated somatic cells are fibroblasts, nerve cells, amniotic fluid cells, bone marrow cells, blood cells, myocardial cells, dermal or epidermal cells, connective tissue cells, chondrocytes, rod and cone cells, retinal pigment epithelia, or pancreatic cells.

7. The method of claim 6, wherein the fibroblast is dermal fibroblast.

8. The method of claim 6, wherein the blood cell is peripheral blood mononuclear cell.

9. The method of claim 1, wherein the iPSCs can differentiate to nervous system, teeth, hair, exocrine glands, epithelium, or mesenchyme from ectoderm.

10. The method of claim 1, wherein the iPSCs can differentiate to the muscle of smooth, cardiac and skeletal, the muscles of the tongue, the pharyngeal arches muscle, connective tissue, dermis and subcutaneous layer of the skin, bone and cartilage, dura mater, endothelium of blood vessels, red blood cells, white blood cells, microglia and Kupffer cells, the kidneys and the adrenal cortex cartilage, gonads, or keratinocytes from mesoderm.

11. The method of claim 1, wherein the iPSCs can differentiate to lung cells, thyroid cells, pancreatic cells, liver cells, retinal pigment epithelium, or eyes from endoderm.

12. An iPSC(s) obtained by the method of claim 1.

* * * * *